(12) United States Patent
Su et al.

(10) Patent No.: US 10,111,875 B2
(45) Date of Patent: Oct. 30, 2018

(54) PYRROLOPYRIMIDINE COMPOUNDS AND USES THEREOF

(71) Applicant: HUTCHISON MEDIPHARMA LIMITED, Shanghai (CN)

(72) Inventors: Wei-Guo Su, Shanghai (CN); Wei Deng, Shanghai (CN); Jinshui Li, Shanghai (CN); Jianguo Ji, Shanghai (CN)

(73) Assignee: HUTCHINSON MEDIPHARMA LIMITED, Shanghai (CN)

( * ) Notice: Subject to any disclaimer, the term of this patent is extended or adjusted under 35 U.S.C. 154(b) by 0 days.

(21) Appl. No.: 15/134,223

(22) Filed: Apr. 20, 2016

(65) Prior Publication Data

US 2016/0228443 A1 Aug. 11, 2016

Related U.S. Application Data

(62) Division of application No. 13/817,802, filed as application No. PCT/CN2011/078575 on Aug. 18, 2011, now Pat. No. 9,346,810.

(30) Foreign Application Priority Data

Aug. 20, 2010 (CN) .......................... 2010 1 0257786
Aug. 20, 2010 (WO) ................. PCT/CN2010/076187

(51) Int. Cl.
*A61K 31/519* (2006.01)
*A61K 31/5377* (2006.01)
*A61K 45/06* (2006.01)
*C07D 471/04* (2006.01)
*C07D 487/04* (2006.01)

(52) U.S. Cl.
CPC ........ *A61K 31/519* (2013.01); *A61K 31/5377* (2013.01); *A61K 45/06* (2013.01); *C07D 471/04* (2013.01); *C07D 487/04* (2013.01); *C07B 2200/07* (2013.01)

(58) Field of Classification Search
CPC .. C07D 471/04; C07D 487/04; A61K 31/519; A61K 31/5377; A61K 45/06; C07B 2200/07
See application file for complete search history.

(56) References Cited

U.S. PATENT DOCUMENTS

2007/0135461 A1    6/2007   Rodgers et al.

FOREIGN PATENT DOCUMENTS

| WO | 1999065909 A1 | 12/1999 |
|---|---|---|
| WO | 2002000661 A1 | 1/2002 |
| WO | 2008117796 A1 | 10/2008 |
| WO | 2008119792 A1 | 10/2008 |
| WO | 2009140320 A1 | 11/2009 |
| WO | 2011029043 A1 | 3/2011 |
| WO | 2011029046 A1 | 3/2011 |

OTHER PUBLICATIONS

Cook et. al., Journal of Medicinal Chemistry, 2010, American Chemical Society, vol. 53. pp. 4615-4622.*
International Search Report dated Aug. 20, 2010.

* cited by examiner

*Primary Examiner* — Sarah Pihonak
(74) *Attorney, Agent, or Firm* — Gorman IP Law, APC

(57) ABSTRACT

The present disclosure provides pyrrolopyrimidine compounds and methods of use therefor. For example, the disclosure provides certain pyrrolopyrimidine compounds capable of inhibiting JAK kinases. The disclosure further provides the pharmaceutical compositions containing these pyrrolopyrimidine compounds, and use of these pyrrolopyrimidine compounds in the treatment of disorders or diseases, such as inflammatory diseases and cancer.

23 Claims, No Drawings

PYRROLOPYRIMIDINE COMPOUNDS AND USES THEREOF

This application is a Divisional Application of U.S. Ser. No. 13/817,802, filed Apr. 25, 2013, which was the National Phase Under 35 USC § 371 of PCT International Application No. PCT/CN2011/078575 which has an International filing date of Aug. 18, 2011, which claims priority under 35 U.S.C. § 119 on Patent Application No. 201010257786.7 filed in China on Aug. 20, 2010, and to International Patent Application PCT/CN2010/076187 filed in China on Aug. 20, 2010, the entire contents of each of which are hereby incorporated by reference.

TECHNICAL FIELD

The present disclosure relates to the pharmaceutical field. For example, the present disclosure relates to certain pyrrolopyrimidine compounds, a composition containing said compound, and the use thereof. These pyrrolopyrimidine compounds can effectively inhibit the activity of JAK kinases.

TECHNICAL BACKGROUND

The Janus kinase (JAK) family is one of the well recognized families of non-receptor tyrosine kinases. The JAK family may be activated by the binding of a cytokine to a cell surface receptor. Activated Jak may then initiate intracellular signaling cascades. The Jak family and Signal Transducers and Activators of Transcription (STATs) are involved in the signaling pathways of a wide range of cytokines.

The JAK/STAT pathway has been shown to play a role in inflammatory diseases, such as, inflammatory diseases of the respiratory tract, multiple sclerosis, rheumatoid arthritis, asthma, inflammatory bowel disease, allergies, autoimmune diseases and other immune reactions. The JAK/STAT pathway, for example, JAK3/STAT, may also play a role in cancers.

Inhibitors of the Jak family are widely sought after and published for treatment or prevention of inflammatory diseases or cancers.

The Janus kinase family of protein tyrosine kinases (JAKs) may play a role in the cytokine-dependent regulation of proliferation and function of cells involved in immune response. Four mammalian JAK family members have been reported: JAK1 (also known as Janus kinase-1), JAK2 (also known as Janus kinase-2), JAK3 (also known as Janus kinase, leukocyte; JAKL; L-JAK and Janus kinase-3) and TYK2 (also known as protein-tyrosine kinase 2). The JAK proteins may range in size from 120 to 140 kDa and comprise seven conserved JAK homology (JH) domains; one of those can be a functional catalytic kinase domain, and another can be a pseudokinase domain potentially serving a regulatory function and/or serving as a docking site for STATs (Scott, Godshall et al. *Clin. Diagn. Lab. Immunol*, 9 (6): 1153-1159, 2002). While JAK1, JAK2 and TYK2 can be ubiquitously expressed, JAK3 is reported to be expressed, for example, in natural killer (NK) cells and not resting T cells, suggesting a role in lymphoid activation (Kawamura, M., D. W. McVicar, et al. "Molecular cloning of L-JAK, a Janus family protein-tyrosine kinase expressed in natural killer cells and activated leukocytes." *Proc Natl Acad Sci USA* 91(14): 6374-8, 1994).

The JAK/STAT pathway reportedly plays a role in the pathogenesis of the asthmatic response, chronic obstructive pulmonary disease, bronchitis, and other related inflammatory diseases of the lower respiratory tract. ("JAK-STAT signaling in asthma." *J Clin Invest* 109(10): 1279-83, 2002 The JAK/STAT pathway has also been implicated to play a role in inflammatory diseases/conditions of the eye including, but not limited to, iritis, uveitis, scleritis, conjunctivitis, as well as chronic allergic responses. Therefore, inhibition of JAK kinases may have a beneficial role in the therapeutic treatment of those diseases.

Inhibition of the JAK kinases can be also envisioned to have therapeutic benefits in patients suffering from skin immune disorders such as psoriasis, and skin sensitization. In psoriasis vulgaris, the most common form of psoriasis, it may have been generally accepted that activated T lymphocytes can be important for the maintenance of the disease and its associated psoriatic plaques (Gottlieb, A. B., et al, *Nat Rev Drug Disc.*, 4:19-34, 2005). Psoriatic plaques may contain a significant immune infiltrate, including leukocytes and monocytes, as well as multiple epidermal layers with increased keratinocyte proliferation. While the initial activation of immune cells in psoriasis may occur by an ill defined mechanism, the maintenance has been reported to be dependent on a number of inflammatory cytokines, in addition to various chemokines and growth factors (JCI, 113: 1664-1675, 2004). Many of those, including interleukins-2, -4, -6, -7, -12, -15, -18, and -23 as well as GM-CSF and IFNg, may signal through the Janus (JAK) kinases (*Adv Pharmacol*. 47: 113-74, 2000). As such, blocking signal transduction at the level of JAK kinases may result in therapeutic benefits in patients suffering from psoriasis or other immune disorders of the skin.

Blocking signal transduction at the level of the JAK kinases may also hold promise for developing treatments for human cancers. Cytokines of the interleukin 6 (IL-6) family, which may activate the signal transducer gp130, may be major survival and growth factors for human multiple myeloma (MM) cells. The signal transduction of gp130 is believed to involve JAK1, JAK2 and TYK2 and the downstream effectors STAT3 and the mitogen-activated protein kinase (MAPK) pathways. In IL-6-dependent MM cell lines treated with the JAK2 inhibitor tyrphostin AG490, JAK2 kinase activity and ERK2 and STAT3 phosphorylation may be inhibited. Furthermore, cell proliferation may be suppressed and apoptosis may be induced (De Vos, J., M. Jourdan, et al. "JAK2 tyrosine kinase inhibitor tyrphostin AG490 downregulates the mitogen-activated protein kinase (MAPK) and signal transducer and activator of transcription (STAT) pathways and induces apoptosis in myeloma cells." *Br J Haematol* 109(4): 823-8, 2000). However, in some cases, AG490 can induce dormancy of tumor cells and can then protect them from death.

It has been suggested that inhibition of JAK2 tyrosine kinase can be beneficial for patients with myeloproliferative disorder. (Levin, et al., *Cancer Cell*, vol. 7: 387-397, 2005). Myeloproliferative disorder (MPD) may include polycythemia vera (PV), essential thrombocythemia (ET), myeloid metaplasia with myelofibrosis (MMM), chronic myelogenous leukemia (CML), chronic myelomonocytic leukemia (CMML), hypereosinophilic syndrome (HES), and systemic mast cell disease (SMCD). Although the myeloproliferative disorders (such as PV, ET and MMM) are thought to be caused by acquired somatic mutation in hematopoietic progenitors, the genetic basis for these diseases has not been known. However, it has been reported that hematopoietic cells from a majority of patients with PV and a significant number of patients with ET and MMM possessed a recurrent somatic activating mutation in the JAK2 tyrosine kinase. It has also been reported that inhibition of the JAK2V617F kinase with a small molecule inhibitor led to inhibition of proliferation of hematopoietic cells, suggesting that the JAK2 tyrosine kinase can be a potential target for pharmacologic inhibition in patients with PV, ET and MMM.

SUMMARY

Provided is at least one compound of formula (1):

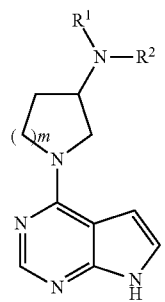

(I)

and/or at least one pharmaceutically acceptable salt thereof wherein $R^1$ is chosen from hydrogen, alkyl, cycloalkyl and heterocycle, $R^2$ is chosen from aryl, heterocycle, heteroaryl, —C(O)$NR^cR^d$, —S(O)$_n R^f$, and —S(O)$_n NR^cR^d$, or $R^1$ and $R^2$, together with the N atom to which they are attached, form an optionally substituted 3- to 7-membered ring, which optionally comprises one or two additional heteroatoms and which is further optionally fused to an optionally substituted heteroaryl or optionally substituted aryl ring;

and each of above said alkyl, aryl, cycloalkyl, heterocycle, heteroaryl in $R^1$ and $R^2$ is optionally substituted with one or more groups chosen from optionally substituted lower alkyl, optionally substituted aryl, optionally substituted alkenyl, optionally substituted alkynyl, optionally substituted cycloalkyl, —C(O)$R^a$, —C(O)$OR^b$, —CN, —C(O)$NR^cR^d$, halo, optionally substituted haloalkyl, optionally substituted heterocycle, optionally substituted heteroaryl, —$NR^cR^d$, —$NR^eC(O)R^a$, —$NR^eC(O)OR^b$, —$NR^eC(O)NR^cR^d$, —$NR^eS(O)_nR^f$, —$NR^eS(O)_nNR^cR^d$, —NO$_2$, —OR$^b$, —S(O)$_n R^f$, and —S(O)$_n NR^cR^d$;

m and n are independently chosen from 0, 1, and 2;

for each occurrence, $R^a$, $R^b$, $R^c$, $R^d$, $R^e$ and $R^r$ are each independently chosen from hydrogen, optionally substituted alkyl, optionally substituted alkenyl, optionally substituted alkynyl, optionally substituted cycloalkyl, optionally substituted aryl, optionally substituted haloalkyl, optionally substituted heteroaryl and optionally substituted heterocycle, or $R^c$ and $R^d$, with the nitrogen to which they are attached, combine to form a heterocycle ring, which is optionally substituted with one or more groups chosen from halo, lower alkyl, hydroxy, and lower alkoxy, wherein the heterocycle ring further optionally comprises one or two additional heteroatoms chosen from N, O and S;

wherein each optionally substituted group above can be unsubstituted or independently substituted with one or more, such as one, two, or three, substituents independently chosen from $C_1$-$C_4$ alkyl, cycloalkyl, aryl, heterocycle, heteroaryl, aryl-$C_1$-$C_4$ alkyl-, heteroaryl-$C_1$-$C_4$ alkyl-, $C_1$-$C_4$ haloalkyl-, —O$C_1$-$C_4$ alkyl, —O$C_1$-$C_4$ alkylphenyl, —$C_1$-$C_4$ alkyl-OH, —$C_1$-$C_4$ alkyl-O—$C_1$-$C_4$ alkyl, —O$C_1$-$C_4$ haloalkyl, halo, —OH, —NH$_2$, —$C_1$-$C_4$ alkyl-NH$_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo, —CO$_2$H, —C(O)O$C_1$-$C_4$ alkyl, —CON($C_1$-$C_4$ alkyl)($C_1$-$C_4$ alkyl), —CONH($C_1$-$C_4$ alkyl), —CONH$_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —SO$_2$($C_1$-$C_4$ alkyl), —SO$_2$(phenyl), —SO$_2$($C_1$-$C_4$ haloalkyl), —SO$_2$NH$_2$, —SO$_2$NH($C_1$-$C_4$ alkyl), —SO$_2$NH(phenyl), —NHSO$_2$($C_1$-$C_4$ alkyl), —NHSO$_2$(phenyl), and —NHSO$_2$($C_1$-$C_4$ haloalkyl), in which each of phenyl, aryl, heterocycle, and heteroaryl is optionally substituted by one or more groups chosen from halo, cycloalkyl, heterocycle, $C_1$-$C_4$ alkyl, $C_1$-$C_4$ haloalkyl-, —O$C_1$-$C_4$ alkyl, $C_1$-$C_4$ alkyl-OH, —$C_1$-$C_4$ alkyl-O—$C_1$-$C_4$ alkyl, —O$C_1$-$C_4$ haloalkyl, cyano, nitro, —NH$_2$, —CO$_2$H, —C(O)O$C_1$-$C_4$ alkyl, —CON($C_1$-$C_4$ alkyl)($C_1$-$C_4$ alkyl), —CONH($C_1$-$C_4$ alkyl), —CONH$_2$, —NHC(O)($C_1$-$C_4$ alkyl), —N($C_1$-$C_4$ alkyl)C(O)($C_1$-$C_4$ alkyl), —SO$_2$($C_1$-$C_4$ alkyl), —SO$_2$(phenyl), —SO$_2$($C_1$-$C_4$ haloalkyl), —SO$_2$NH$_2$, —SO$_2$NH($C_1$-$C_4$ alkyl), —SO$_2$NH(phenyl), —NHSO$_2$($C_1$-$C_4$ alkyl), —NHSO$_2$(phenyl), and —NHSO$_2$($C_1$-$C_4$ haloalkyl).

Also provided is a composition comprising at least one compound and/or at least one pharmaceutically acceptable salt described herein and at least one pharmaceutically acceptable carrier.

Also provided is a method of inhibiting the activity of at least one kinase chosen from JAK1, JAK2, JAK3 and TYK2 comprising contacting at least one kinase with an effective amount of at least one compound and/or at least one pharmaceutically acceptable salt described herein.

Also provided is a method of treating in a subject an inflammatory disease responsive to inhibition of at least one kinase chosen from JAK1, JAK2, JAK3 and TYK2 comprising administering to the subject in need thereof an effective amount of at least one compound and/or at least one pharmaceutically acceptable salt described herein.

Also provided is a method of treating in a subject cancer responsive to inhibition of at least one kinase chosen from JAK1, JAK2, JAK3 and TYK2 comprising administering to the subject in need thereof an effective amount of at least one compound and/or at least one pharmaceutically acceptable salt described herein.

Also provided is a use of at least one compound and/or at least one pharmaceutically acceptable salt described herein, in the preparation of a medication for treating an inflammatory disease or cancer responsive to inhibition of at least one kinase chosen from JAK1, JAK2, JAK3 and TYK2.

Also provided is a medication or pharmaceutical composition for treating an inflammatory disease or cancer responsive to inhibition of at least one kinase chosen from JAK1, JAK2, JAK3 and TYK2, which comprises at least one compound and/or at least one pharmaceutically acceptable salt described herein and at least one pharmaceutically acceptable carrier.

DETAILED DESCRIPTION

As used in the present specification, the following words, phrases and symbols are generally intended to have the meanings as set forth below, except to the extent that the context in which they are used indicates otherwise. The following abbreviations and terms have the indicated meanings throughout:

A dash ("-") that is not between two letters or symbols is used to indicate a point of attachment for a substituent. For example, —CONH$_2$ is attached through the carbon atom.

The term "alkyl" herein refers to a straight or branched hydrocarbon, containing 1-10 carbon atoms, such as 1-6 carbon atoms, further such as 1-4 carbon atoms. Examples of alkyl groups include, but are not limited to, methyl, ethyl, n-propyl, i-propyl, n-butyl, i-butyl, and t-butyl. "Lower alkyl" refers to a straight or branched hydrocarbon, containing 1-4 carbon atoms.

By "alkoxy" is meant a straight or branched alkyl group of the indicated number of carbon atoms attached through an oxygen bridge such as, for example, methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. Alkoxy groups will usually have from 1 to 6 carbon atoms attached through the oxygen bridge. "Lower alkoxy" refers to a straight or branched alkoxy, wherein the alkyl portion contains 1-4 carbon atoms.

The term "alkenyl" herein refers to a $C_{2-10}$ straight or branched hydrocarbon, containing one or more C=C double bonds. For example, "alkenyl" refers to a $C_{2-6}$alkenyl. Examples of alkenyl groups include, but are not limited to, vinyl, 2-propenyl, and 2-butenyl.

The term "alkynyl" herein refers to a $C_{2-10}$ straight or branched hydrocarbon, containing one or more C≡C triple bonds. For further example, "alkynyl" refers to a $C_{2-6}$ alkynyl. Examples of alkynyl groups include, but are not limited to, ethynyl, 2-propynyl, and 2-butynyl.

The term "cycloalkyl" refers to saturated and partially unsaturated monocyclic, bicyclic, or tricyclic hydrocarbon rings having 3 to 12 carbons, such as having 3 to 8 carbons. Examples of cycloalkyl groups include, but are not limited to, cyclopropyl, cyclobutyl, cyclopentyl, cyclopentenyl, cyclohexyl, cyclohexenyl, cycloheptyl, and cyclooctyl. The ring may be saturated or have one or more double bonds (i.e. partially unsaturated), but not fully conjugated, and not aromatic, as defined herein.

"Aryl" encompasses:

5- and 6-membered carbocyclic aromatic rings, for example, benzene;

bicyclic ring systems wherein at least one ring is carbocyclic and aromatic, for example, naphthalene, indane, and 1,2,3,4-tetrahydroquinoline; and tricyclic ring systems wherein at least one ring is carbocyclic and aromatic, for example, fluorene.

For example, aryl includes 5- and 6-membered carbocyclic aromatic rings fused to a 5- to 7-membered heterocyclic ring containing one or more heteroatoms selected from N, O, and S, provided that the point of attachment is at the carbocyclic aromatic ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap in any way with heteroaryl, separately defined below. Hence, if one or more carbocyclic aromatic rings are fused with a heterocyclic aromatic ring, the resulting ring system is heteroaryl, not aryl, as defined herein.

The term "halo" includes fluoro, chloro, bromo, and iodo, and the term "halogen" includes fluorine, chlorine, bromine, and iodine.

The term "heteroaryl" refers to 5- to 8-membered aromatic, monocyclic rings containing one or more, for example, from 1 to 4, or, in some embodiments, from 1 to 3, heteroatoms selected from N, O, and S, with the remaining ring atoms being carbon;

8- to 12-membered bicyclic rings containing one or more, for example, from 1 to 6, or, in some embodiments, from 1 to 4, or in some embodiments, from 1 to 3, heteroatoms selected from N, O, and S, with the remaining ring atoms being carbon and wherein at least one heteroatom is present in an aromatic ring; and 11- to 14-membered tricyclic rings containing one or more, for example, from 1 to 6, or in some embodiments, from 1 to 4, or in some embodiments, from 1 to 3, heteroatoms selected from N, O, and S, with the remaining ring atoms being carbon and wherein at least one heteroatom is present in an aromatic ring.

For example, heteroaryl includes a 5- to 7-membered heterocyclic aromatic ring fused to a 5- to 7-membered cycloalkyl ring. For such fused, bicyclic heteroaryl ring systems wherein only one of the rings contains one or more heteroatoms, the point of attachment may be at the heteroaromatic ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1.

Examples of heteroaryl groups include, but are not limited to, (as numbered from the linkage position assigned priority 1), 2-pyridyl, 3-pyridyl, 4-pyridyl, 2,3-pyrazinyl, 3,4-pyrazinyl, 2,4-pyrimidinyl, 3,5-pyrimidinyl, 1-pyrazolyl, 2,3-pyrazolyl, 2,4-imidazolinyl, isoxazolyl, oxazolyl, thiazolyl, thiadiazolyl, tetrazolyl, thienyl, benzothienyl, furyl, benzofuryl, benzoimidazolinyl, indolinyl, pyridizinyl, triazolyl, quinolinyl, pyrazolyl, and 5,6,7,8-tetrahydroisoquinoline.

Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. Heteroaryl does not encompass or overlap with aryl as defined above.

Substituted heteroaryl also includes ring systems substituted with one or more oxide (—O$^-$) substituents, such as pyridinyl N-oxides.

By "heterocycle" is a 4- to 12-membered monocyclic, bicyclic or tricyclic saturated or partially unsaturated ring containing at least 2 carbon atoms in addition to 1-3 heteroatoms independently selected from oxygen, sulfur, and nitrogen. "Heterocycle" also refers to 5- to 7-membered heterocyclic ring containing one or more heteroatoms selected from N, O, and S fused with 5- and 6-membered aromatic ring, provided that the point of attachment is at the heterocyclic ring. The rings may be saturated or have one or more double bonds (i.e. partially unsaturated). The heterocycle can be substituted by oxo. The point of the attachment may be carbon or heteroatom in the heterocyclic ring. A heterocycle is not a heteroaryl as defined herein.

Suitable heterocycles include, for example (as numbered from the linkage position assigned priority 1), 1-pyrrolidinyl, 2-pyrrolidinyl, 2,4-imidazolidinyl, 2,3-pyrazolidinyl, 1-piperidinyl, 2-piperidinyl, 3-piperidinyl, 4-piperidinyl, and 2,5-piperazinyl. Morpholinyl groups are also contemplated, including 2-morpholinyl and 3-morpholinyl (numbered wherein the oxygen is assigned priority 1). Substituted heterocycle also includes ring systems substituted with one or more oxo moieties, such as piperidinyl N-oxide, morpholinyl-N-oxide, 1-oxo-1-thiomorpholinyl and 1,1-dioxo-1-thiomorpholinyl.

By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

The term "substituted", as used herein, means that any one or more hydrogens on the designated atom or group is replaced with a selection from the indicated group, provided that the designated atom's normal valence is not exceeded. When a substituent is oxo (i.e., =O) then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility. Unless otherwise specified, substituents are named into the core structure. For example, it is to be understood that when (cycloalkyl)alkyl is listed as a possible substituent, the point of attachment of this substituent to the core structure is in the alkyl portion.

In some embodiments, "substituted with one or more groups" refers to two hydrogens on the designated atom or group being independently replaced with two selections from the indicated group of substituents. In some embodiments, "substituted with one or more groups" refers to three hydrogens on the designated atom or group being independently replaced with three selections from the indicated group of substituents. In some embodiments, "substituted with one or more groups" refers to four hydrogens on the designated atom or group being independently replaced with four selections from the indicated group of substituents.

Compounds described herein include, but are not limited to, when possible, their optical isomers, such as enantiomers and diastereomers, mixtures of enantiomers, including racemates, mixtures of diastereomers, and other mixtures thereof, to the extent they can be made by one of ordinary skill in the art by routine experimentation. In those situations, the single enantiomers or diastereomers, i.e., optically active forms, can be obtained by asymmetric synthesis or by resolution of the racemates or mixtures of diastereomers. Resolution of the racemates or mixtures of diastereomers, if possible, can be accomplished, for example, by conventional methods such as crystallization in the presence of a resolving agent, or chromatography, using, for example a chiral high-pressure liquid chromatography (HPLC) column. In addition, such compounds include Z- and E-forms (or cis- and trans-forms) of compounds with carbon-carbon double bonds. Where compounds described herein exist in various tautomeric forms, the term "compound" is intended to include, to the extent they can be made without undue experimentation, all tautomeric forms of the compound. Such compounds also include crystal forms including polymorphs and clathrates, to the extent they can be made by one of ordinary skill in the art without undue experimentation. Similarly, the term "salt" is intended to include all isomers, racemates, other mixtures, Z- and E-forms, tautomeric forms and crystal forms of the salt of the compound, to the extent they can be made by one of ordinary skill in the art without undue experimentation.

"Pharmaceutically acceptable salts" include, but are not limited to salts with inorganic acids, such as hydrochlorate, phosphate, diphosphate, hydrobromate, sulfate, sulfinate, nitrate, and like salts; as well as salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate, $HOOC-(CH_2)_n-COOH$ where n is 0-4, and like salts. Similarly, pharmaceutically acceptable cations include, but are not limited to sodium, potassium, calcium, aluminum, lithium, and ammonium.

In addition, if a compound described herein is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used without undue experimentation to prepare non-toxic pharmaceutically acceptable addition salts.

A "solvate," such as a "hydrate," is formed by the interaction of a solvent and a compound. The term "compound" is intended to include solvates, including hydrates, of compounds, to the extent they can be made by one of ordinary skill in the art by routine experimentation. Similarly, "salts" includes solvates, such as hydrates, of salts, to the extent they can be made by one of ordinary skill in the art by routine experimentation. Suitable solvates are pharmaceutically acceptable solvates, such as hydrates, including monohydrates and hemi-hydrates, to the extent they can be made by one of ordinary skill in the art by routine experimentation.

A "chelate" is formed by the coordination of a compound to a metal ion at two (or more) points. The term "compound" is intended to include chelates of compounds. Similarly, "salts" includes chelates of salts.

A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding). Such non-covalent complexes are included in the term "compound".

The term "hydrogen bond" refers to a form of association between an electronegative atom (also known as a hydrogen bond acceptor) and a hydrogen atom attached to a second, relatively electronegative atom (also known as a hydrogen bond donor). Suitable hydrogen bond donor and acceptors are well understood in medicinal chemistry (G. C. Pimentel and A. L. McClellan, The Hydrogen Bond, Freeman, San Francisco, 1960; R. Taylor and O. Kennard, "Hydrogen Bond Geometry in Organic Crystals", Accounts of Chemical Research, 17, pp. 320-326 (1984)).

As used herein the terms "group", "radical" or "fragment" are synonymous and are intended to indicate functional groups or fragments of molecules attachable to a bond or other fragments of molecules.

The term "active agent" is used to indicate a chemical substance which has biological activity. In some embodiments, an "active agent" is a chemical substance having pharmaceutical utility.

"Treating," "treat," or "treatment" or "alleviation" refers to administering at least one compound and/or at least one pharmaceutically acceptable salt described herein to a subject that has a disease or disorder, or has a symptom of a disease or disorder, or has a predisposition toward a disease or disorder, with the purpose to cure, heal, alleviate, relieve, alter, remedy, ameliorate, improve, or affect cancer, the symptoms of the disease or disorder, or the predisposition toward the disease or disorder. In some embodiments, the disease or disorder may be cancer. In some embodiments, the disease or disorder may be an inflammatory disease.

The term "effective amount" refers to an amount of at least one compound and/or at least one pharmaceutically acceptable salt described herein effective to "treat", as defined above, a disease or disorder in a subject. The effective amount may cause any of the changes observable or measurable in a subject as described in the definition of "treating," "treat," "treatment" and "alleviation" above. For example, in the case of cancer, the effective amount can reduce the number of cancer or tumor cells; reduce the tumor size; inhibit or stop tumor cell infiltration into peripheral organs including, for example, the spread of tumor into soft tissue and bone; inhibit and stop tumor metastasis; inhibit and stop tumor growth; relieve to some extent one or more of the symptoms associated with the cancer, reduce morbidity and mortality; improve quality of life; or a combination of such effects. An effective amount may be an amount sufficient to decrease the symptoms of a disease responsive to inhibition of at least one kinase chosen from JAK1, JAK2, JAK3 and TYK2. For cancer therapy, efficacy in vivo can, for example, be measured by assessing the duration of survival, time to disease progression (TTP), the response rates (RR), duration of response, and/or quality of life. Effective amounts may vary, as recognized by those skilled in the art, depending on route of administration, excipient usage, and co-usage with other agents. An effective amount may also be an amount sufficient for a pharmaceutical composition comprising at least one compound and/or at least one pharmaceutically acceptable salt to meet regulatory requirements, such as SFDA, USFDA, or European approval, to "treat", as defined above, a disease or disorder in a human patient. An effective amount may also be an amount sufficient for a pharmaceutical composition comprising at least one compound and/or at least one pharmaceutically acceptable salt to show efficacy by a randomized, double blind clinical trial to "treat", as defined above, a disease or disorder in a human.

The term "effective amount" may also refer to an amount of at least one compound and/or at least one pharmaceutically acceptable salt described herein effective to inhibit the activity of at least one kinase chosen from JAK1, JAK2, JAK3 and TYK2.

The term "inhibition" indicates a decrease in the baseline activity of a biological activity or process. "Inhibition of at least one kinase chosen from JAK1, JAK2, JAK3 and TYK2" refers to a decrease in the activity of the at least one kinase chosen from JAK1, JAK2, JAK3 and TYK2 as a direct or indirect response to the presence of at least one compound and/or at least one pharmaceutically acceptable salt described herein, relative to the activity of the at least one kinase chosen from JAK1, JAK2, JAK3 and TYK2 in the absence of the at least one compound and/or the at least one pharmaceutically acceptable salt thereof. The decrease in activity may be due to the direct interaction of the at least one compound and/or at least one pharmaceutically acceptable salt described herein with the at least one kinase chosen from JAK1, JAK2, JAK3 and TYK2, or due to the interaction of the at least one compound and/or at least one pharmaceutically acceptable salt described herein, with one or more other factors that in turn affect the at least one kinase activity. For example, the presence of at least one compound and/or at least one pharmaceutically acceptable salt described herein, may decrease the at least one kinase activity by directly binding to the at least one kinase, by causing (directly or indirectly) another factor to decrease the at least one kinase activity, or by (directly or indirectly) decreasing the amount of the at least one kinase present in the cell or organism.

Provided is at least one compound of formula (I):

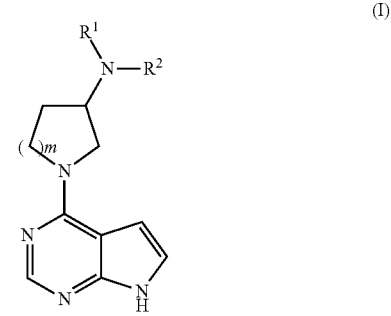

and/or at least one pharmaceutically acceptable salt thereof wherein $R^1$ is chosen from hydrogen, alkyl, cycloalkyl and heterocycle, $R^2$ is chosen from aryl, heterocycle, heteroaryl, —C(O)NR$^c$R$^d$, —S(O)$_n$R$^f$, and —S(O)$_n$NR$^c$R$^d$, or $R^1$ and $R^2$, together with the N atom to which they are attached, form an optionally substituted 3- to 7-membered ring, which optionally comprises one or two additional heteroatoms and which is further optionally fused to an optionally substituted heteroaryl or optionally substituted aryl ring;

and each of above said alkyl, aryl, cycloalkyl, heterocycle, heteroaryl in $R^1$ and $R^2$ is optionally substituted with one or more groups chosen from optionally substituted lower alkyl, optionally substituted aryl, optionally substituted alkenyl, optionally substituted alkynyl, optionally substituted cycloalkyl, —C(O)R$^a$, —C(O)OR$^b$, —CN, —C(O)NR$^c$R$^d$, halo, optionally substituted haloalkyl, optionally substituted heterocycle, optionally substituted heteroaryl, —NR$^c$R$^d$, —NR$^e$C(O)R$^a$, —NR$^e$C(O)OR$^b$, —NR$^e$C(O)NR$^c$R$^d$, —NR$^e$S(O)$_n$R$^f$, —NR$^e$S(O)$_n$NR$^c$R$^d$, —NO$_2$, —OR$^b$, —S(O)$_n$R$^f$, and —S(O)$_n$NR$^c$R$^d$;

m and n are independently chosen from 0, 1, and 2;

for each occurrence, R$^a$, R$^b$, R$^c$, R$^d$, R$^e$ and R$^f$ are each independently chosen from hydrogen, optionally substituted alkyl, optionally substituted alkenyl, optionally substituted alkynyl, optionally substituted cycloalkyl, optionally substituted aryl, optionally substituted haloalkyl, optionally substituted heteroaryl and optionally substituted heterocycle, or R$^c$ and R$^d$, with the nitrogen to which they are attached, combine to form a heterocycle ring, which is optionally substituted with one or more groups chosen from halo, lower alkyl, hydroxy, and lower alkoxy, wherein the heterocycle ring further optionally comprises one or two additional heteroatoms chosen from N, O and S;

wherein each optionally substituted group above can be unsubstituted or independently substituted with one or more, such as one, two, or three, substituents independently chosen from $C_1$-$C_4$ alkyl, cycloalkyl, aryl, heterocycle, heteroaryl, aryl-$C_1$-$C_4$ alkyl-, heteroaryl-$C_1$-$C_4$ alkyl-, $C_1$-$C_4$ haloalkyl-, —O$C_1$-$C_4$ alkyl, —O$C_1$-$C_4$ alkylphenyl, —$C_1$-$C_4$ alkyl-OH, —$C_1$-$C_4$ alkyl-O—$C_1$-$C_4$ alkyl, —O$C_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo, —$CO_2$H, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2$NH($C_1$-$C_4$ alkyl), —$SO_2$NH(phenyl), —$NHSO_2$($C_1$-$C_4$ alkyl), —$NHSO_2$(phenyl), and —$NHSO_2$($C_1$-$C_4$ haloalkyl), in which each of phenyl, aryl, heterocycle, and heteroaryl is optionally substituted by one or more groups chosen from halo, cycloalkyl, heterocycle, $C_1$-$C_4$ alkyl, $C_1$-$C_4$ haloalkyl-, —O$C_1$-$C_4$ alkyl, $C_1$-$C_4$ alkyl-OH, —$C_1$-$C_4$ alkyl-O—$C_1$-$C_4$ alkyl, —O$C_1$-$C_4$ haloalkyl, cyano, nitro, —$NH_2$, —$CO_2$H, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —N($C_1$-$C_4$ alkyl)C(O)($C_1$-$C_4$ alkyl), —$SO_2$($C_1$-$C_4$ alkyl), —$SO_2$(phenyl), —$SO_2$($C_1$-$C_4$ haloalkyl), —$SO_2NH_2$, —$SO_2$NH($C_1$-$C_4$ alkyl), —$SO_2$NH(phenyl), —$NHSO_2$($C_1$-$C_4$ alkyl), —$NHSO_2$(phenyl), and —$NHSO_2$($C_1$-$C_4$ haloalkyl).

In some embodiments, m is 1.

In some embodiments, $R^1$ is chosen from alkyl and cycloalkyl, each of which is optionally substituted with one or more groups chosen from optionally substituted lower alkyl, optionally substituted aryl, optionally substituted alkenyl, optionally substituted alkynyl, optionally substituted cycloalkyl, —C(O)$R^a$, —C(O)O$R^b$, —CN, —C(O)N$R^cR^d$, halo, optionally substituted haloalkyl, optionally substituted heterocycle, optionally substituted heteroaryl, —N$R^cR^d$, —N$R^e$C(O)$R^a$, —N$R^e$C(O)O$R^b$, —N$R^e$C(O)N$R^cR^d$, —N$R^e$S(O)$_nR^f$, —N$R^e$S(O)$_n$N$R^cR^d$, —$NO_2$, —O$R^b$, —S(O)$_nR^f$, and —S(O)$_n$N$R^cR^d$.

In some embodiments, $R^1$ is alkyl optionally substituted by alkenyl, alkynyl or cycloalkyl.

In some embodiments, $R^1$ is cycloalkyl.

In some embodiments, $R^2$ is aryl or heteroaryl, each of which is optionally substituted with one or more groups chosen from optionally substituted lower alkyl, optionally substituted aryl, optionally substituted alkenyl, optionally substituted alkynyl, optionally substituted cycloalkyl, —C(O)$R^a$, —C(O)O$R^b$, —CN, —C(O)N$R^cR^d$, halo, optionally substituted haloalkyl, optionally substituted heterocycle, optionally substituted heteroaryl, —N$R^cR^d$, —N$R^e$C(O)$R^a$, —N$R^e$C(O)O$R^b$, —NR C(O)N$R^cR^d$, —N$R^e$S(O)$_nR^f$, —N$R^e$S(O)$_n$N$R^cR^d$, —$NO_2$, —O$R^b$, —S(O)$_nR^f$, and —S(O)$_n$N$R^cR^d$.

In some embodiments, $R^2$ is —C(O)N$R^cR^d$, or —S(O)$_n$N$R^cR^d$, wherein $R^a$, $R^c$, and $R^d$ are each independently chosen from hydrogen, optionally substituted alkyl, optionally substituted alkenyl, optionally substituted alkynyl, optionally substituted cycloalkyl, optionally substituted aryl, optionally substituted haloalkyl, optionally substituted heteroaryl and optionally substituted heterocycle, or $R^c$ and $R^d$, with the nitrogen to which they are attached, combine to form a heterocycle ring, which is optionally substituted with one or more groups chosen from halo, lower alkyl, hydroxy, and lower alkoxy, wherein the heterocycle ring further optionally comprises one or two additional heteroatoms chosen from N, O and S.

In some embodiments, $R^2$ is —C(O)N$R^cR^d$, wherein $R^c$ and $R^d$ are each independently chosen from alkyl; phenyl optionally substituted by CN, halo, alkyl and haloalkyl; indanyl substituted by OH; and tetrahydropyranyl.

In some embodiments, $R^2$ is —S(O)$_n$N$R^cR^d$, wherein n is 2, $R^c$ and $R^d$ are each independently chosen from H and alkyl, or $R^c$ and $R^d$, with the nitrogen to which they are attached, form pyrrolidinyl.

In some embodiments, $R^2$ is —S(O)$_n$R, wherein n is 2, $R^f$ is alkyl; or phenyl optionally substituted by one or more groups chosen from halo, —CN, —$NO_2$ and O$R^b$, wherein $R^b$ is —H or alkyl; or cycloalkyl.

In some embodiments, $R^1$ and $R^2$, together with the N atom to which they are attached, form indolinyl, or imidazolonyl fused to pyridine, wherein said indolinyl and pyridine are optionally substituted by —CN.

In some embodiments, $R^2$ is aryl or heteroaryl chosen from

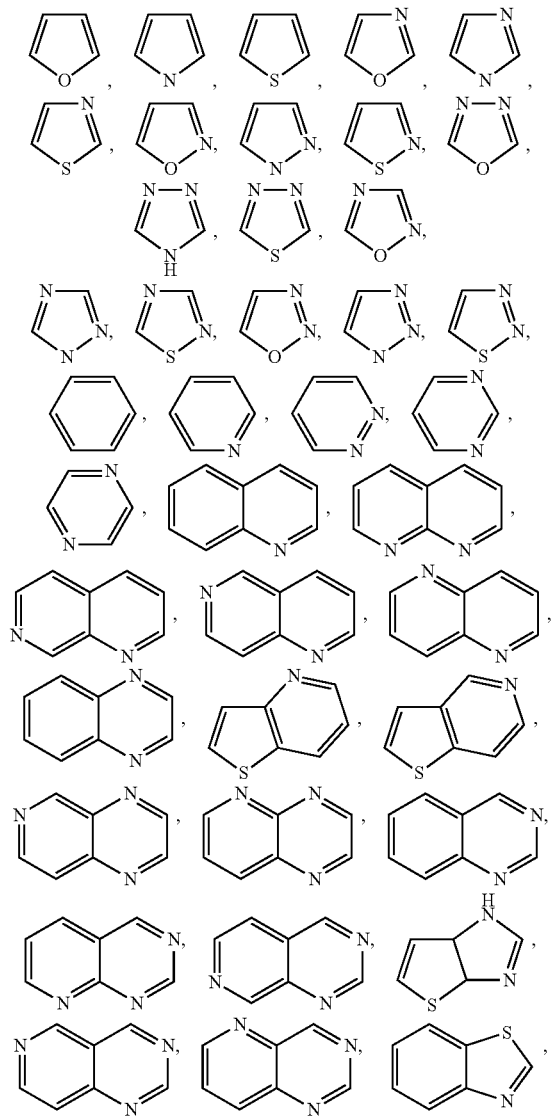

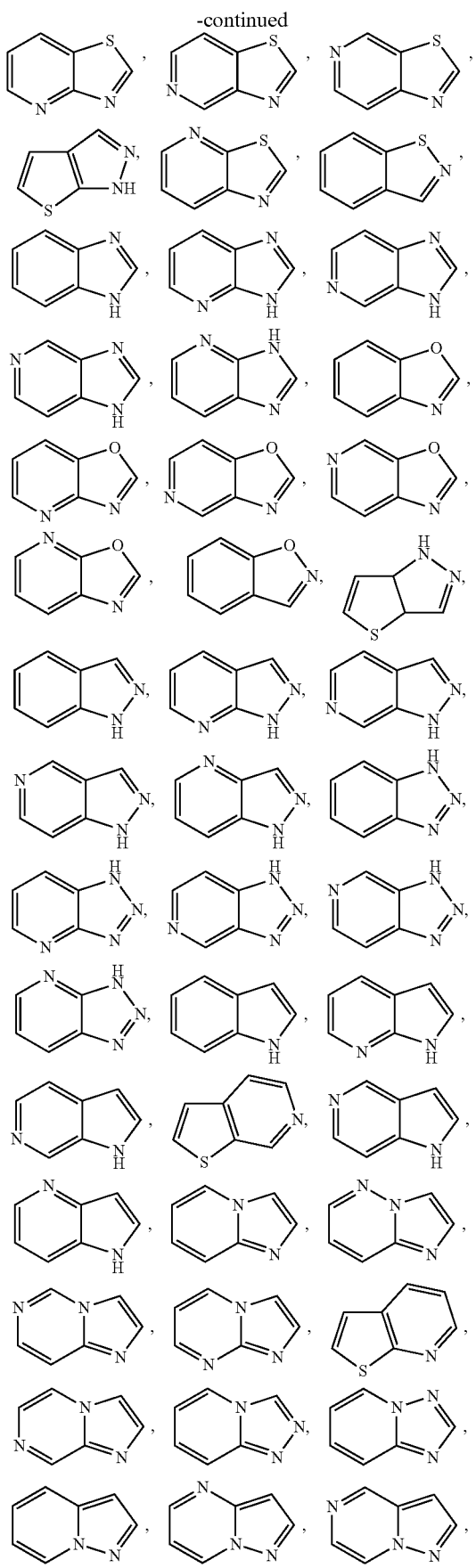

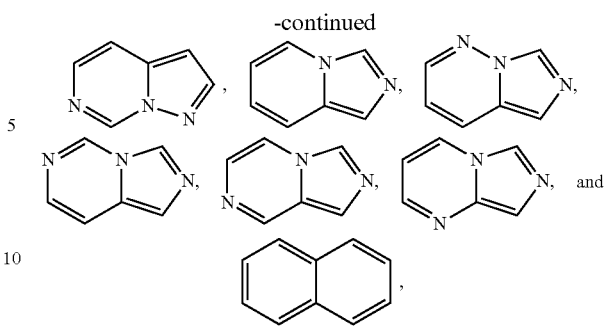

each of which is optionally substituted with one or more groups chosen from optionally substituted alkyl, optionally substituted alkenyl, optionally substituted alkynyl, optionally substituted aryl, optionally substituted cycloalkyl, optionally substituted haloalkyl, —C(O)R$^a$, —C(O)OR$^b$, —CN, —C(O)NR$^c$R$^d$, halo, optionally substituted heterocycle, optionally substituted heteroaryl, —NR$^c$R$^d$, —NR$^c$C(O)R$^a$, —NR$^e$C(O)OR$^b$, —NR$^e$C(O)NR$^c$R$^d$, —NR$^e$S(O)$_n$R$^f$, —NR$^e$S(O)$_n$NR$^c$R$^d$, —NO$_2$, —OR$^b$, —S(O)$_n$R$^f$, and —S(O)$_n$NR$^c$R$^d$.

In some embodiments, R$^2$ is aryl or heteroaryl chosen from

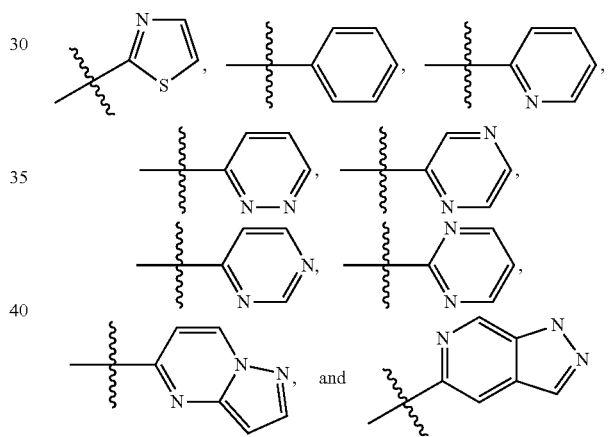

each of which is optionally substituted with one or more groups chosen from optionally substituted alkyl, optionally substituted alkenyl, optionally substituted alkynyl, optionally substituted aryl, optionally substituted cycloalkyl, optionally substituted haloalkyl, —C(O)R$^a$, —C(O)OR$^b$, —CN, —C(O)NR$^c$R$^d$, halo, optionally substituted heterocycle, optionally substituted heteroaryl, —NR$^c$R$^d$, —NR$^c$C(O)R$^a$, —NR$^e$C(O)OR$^b$, —NR$^e$C(O)NR$^c$R$^d$, —NR$^e$S(O)$_n$R$^f$, —NR$^e$S(O)$_n$NR$^c$R$^d$, —NO$_2$, —OR$^b$, —S(O)$_n$R, and —S(O)$_n$NR$^c$R$^d$.

In some embodiments, R$^2$ is

which is optionally substituted with one or more groups chosen from optionally substituted alkyl, optionally substituted alkenyl, optionally substituted alkynyl, optionally substituted aryl, optionally substituted cycloalkyl, optionally substituted haloalkyl, —C(O)$R^a$, —C(O)$OR^b$, —CN, —C(O)$NR^cR^d$, halo, optionally substituted heterocycle, optionally substituted heteroaryl, —$NR^cR^d$, —$NR^cC(O)R^a$, —$NR^eC(O)OR^b$, —$NR^eC(O)NR^cR^d$, —$NR^eS(O)_nR^f$, —$NR^eS(O)^nNR^cR^d$, —$NO_2$, —$OR^b$, —$S(O)_nR^f$, and —$S(O)_nNR^cR^d$.

In some embodiments, $R^2$ is

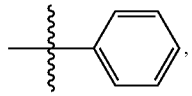

which is optionally substituted with one or more groups chosen from:
—CN;
halo;
haloalkyl;
—$NO_2$;
amino;
—$S(O)_nR^f$, wherein n is 2 and $R^f$ is alkyl or haloalkyl;
phenyl optionally substituted by one or more groups chosen from —CN, alkyloxy and halo;
indanyl optionally substituted by —OH; tetrazolyl; and
—C(O)$NR^cR^d$, wherein $R^c$ and $R^d$ are each independently chosen from —H; alkyl optionally substituted by —OH; alkoxy; phenyl optionally substituted by halo; and indanyl optionally substituted by —OH.

In some embodiments, $R^2$ is

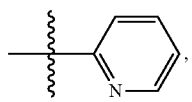

which is optionally substituted with one or more groups chosen from optionally substituted alkyl, optionally substituted alkenyl, optionally substituted alkynyl, optionally substituted aryl, optionally substituted cycloalkyl, optionally substituted haloalkyl, —C(O)$R^a$, —C(O)$OR^b$, —CN, —C(O)$NR^cR^d$, halo, optionally substituted heterocycle, optionally substituted heteroaryl, —$NR^cR^d$, —$NR^cC(O)R^a$, —$NR^eC(O)OR^b$, —$NR^eC(O)NR^cR^d$, —$NR^eS(O)_nR^f$, —$NR^eS(O)_nNR^cR^d$, —$NO_2$, —$OR^b$, —$S(O)_nR^f$, and —$S(O)_nNR^cR^d$.

In some embodiments, $R^2$ is

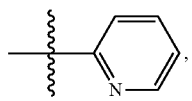

which is optionally substituted with one or more groups chosen from:
—CN;
alkynyl;
halo;
—$NO_2$;
alkyl;
amino;
haloalkyl;
phenyl optionally substituted by —CN;

heteroaryl selected from tetrazolyl, thienyl, pyridinyl and pyrazolyl, said heteroaryl is optionally substituted by alkyl;
—$OR^b$, wherein $R^b$ is —H or alkyl;
—$S(O)_nR^f$ wherein n is 2 and $R^f$ is alkyl;
$COOR^b$ wherein $R^b$ is —H or alkyl;
—C(O)$NR^cR^d$, wherein $R^c$ and $R^d$ are each independently chosen from —H; cycloalkyl optionally substituted by OH; alkyl optionally substituted by one or more groups chosen from —OH and phenyl; phenyl optionally substituted by one or more groups chosen from alkyl, alkoxy and halo; pyridinyl; and thiazolyl;
$NR^cS(O)_nR^f$, wherein n is 2, $R^e$ is —H, $R^f$ is alkyl; cycloalkyl; benzyl optionally substituted by one or more groups chosen from halo and alkyl; phenyl optionally substituted by halo; thienyl; or pyridinyl;
—$NR^eC(O)R^a$, wherein $R^e$ is —H, $R^a$ is cycloalkyl; phenyl optionally substituted by halo; or alkyl substituted by $OR^b$, wherein $R^b$ is alkyl;
$NR^cR^d$, wherein $R^c$ and $R^d$ are benzyl each optionally substituted by halo; and
—$S(O)_nNR^cR^d$, wherein n is 2, $R^c$ and $R^d$ are each independently chosen from —H; alkyl optionally substituted by one or more groups chosen from alkynyl, cycloalkyl, tetrahydrofuranyl, and phenyl optionally substituted by one or more groups chosen from halo and —$OR^b$, wherein $R^b$ is —H or alkyl; cycloalkyl optionally substituted by —OH; indanyl optionally substituted by —OH; tetrahydropyranyl; tetrahydrofuranyl; oxetanyl; pyrazolyl optionally substituted by alkyl; and phenyl optionally substituted by halo; or $R^c$ and $R^d$, with the nitrogen to which they are attached, form a heterocycle ring selected from pyrrolidinyl, piperazinyl and morpholinyl.

In some embodiments, $R^2$ is pyrazinyl optionally substituted with one or more groups chosen from: —CN, alkoxy, morpholino, pyrazolyl, imidazolyl, and —$NR^cR^d$, wherein $R^c$ and $R^d$ are each independently chosen from cycloalkyl and alkyl, each optionally substituted by —OH.

In some embodiments, $R^2$ is pyridazinyl optionally substituted with one or more groups chosen from —CN, halo, and haloalkyl.

In some embodiments, $R^2$ is pyrimidinyl optionally substituted with one or more groups chosen from —CN, halo, —$NO_2$, —$OR^b$, and —$NR^cR^d$, wherein $R^b$, $R^c$ and $R^d$ are each independently chosen from —H and alkyl.

In some embodiments, $R^1$ is chosen from $C_{1-3}$ alkyl, allyl, propargyl, and cyclopropyl, each of which is optionally substituted with one or more groups chosen from optionally substituted lower alkyl, optionally substituted aryl, optionally substituted alkenyl, optionally substituted alkynyl, optionally substituted cycloalkyl, —C(O)$R^a$, —C(O)$OR^b$, —CN, —C(O)$NR^cR^d$, halo, optionally substituted haloalkyl, optionally substituted heterocycle, optionally substituted heteroaryl, —$NR^cR^d$, —$NR^cC(O)R^a$, —$NR^eC(O)OR^b$, —$NR^eC(O)NR^cR^d$, —$NR^eS(O)_nR^f$, —$NR^eS(O)_nNR^cR^d$, —$NO_2$, —$OR^b$, —$S(O)_nR^f$, and —$S(O)_nNR^cR^d$.

In some embodiments, $R^1$ is methyl.

In some embodiments, the absolute stereocenter bearing the —N($R^1$)($R^2$) group is the R-isomer.

Also provided is at least one compound chosen from compounds 1 to 260 and/or at least one pharmaceutically acceptable salt thereof.

The compounds described herein, and/or the pharmaceutically acceptable salts thereof, can be synthesized from commercially available starting materials by methods well known in the art, taken together with the disclosure in this patent application. The following schemes illustrate methods for preparation of most of the compounds disclosed herein.

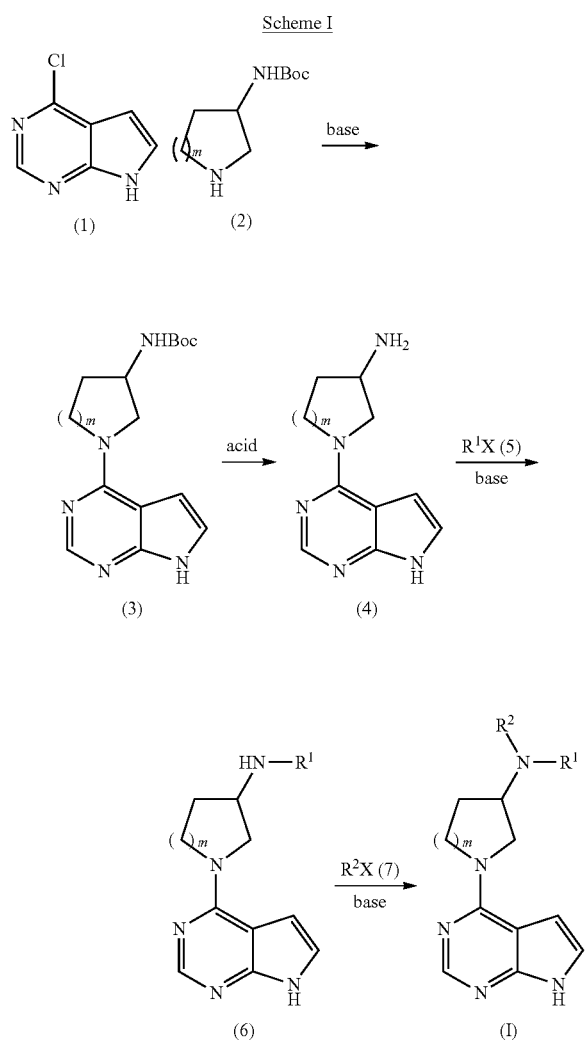

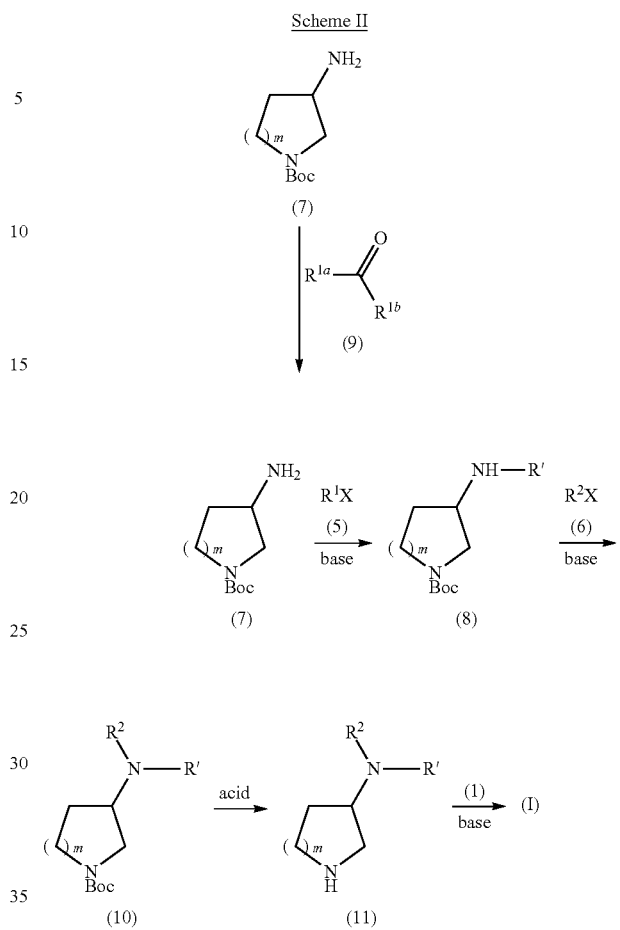

As shown in Scheme I, compounds of formula (1), can react with compounds of formula (2), wherein m is as defined herein, in the presence of a base, such as but not limited to $K_2CO_3$, $Na_2CO_3$, NaH, $Et_3N$ or diisopropylethylamine (DIPEA), to give compounds of formula (3). In the presence of an acid, such as but not limited to HCl or $CF_3CO_2H$, N-Boc group in compound of formula (3) can be deprotected to give the compound of formula (4) that can subsequently react with $R^1X$ and $R^2X$, wherein X is Cl, Br or I, $R^1$ and $R^2$ are as defined herein, in the presence of a base, such as but not limited to $K_2CO_3$, $Na_2CO_3$, $Cs_2CO_3$, NaH, t-BuONa, t-BuOK, $Et_3N$, or diisopropylethylamine (DIPEA), to give the compound of formula (I). When $R^1$ or $R^2$ is an aryl or heteroaryl, a palladium reagent, such as but not limited to $PdCl_2$, $Pd(OAc)_2 Pd_2(dba)_3$ or $Pd(PPh_3)_4$, and a ligand, such as but not limited to $Ph_3P$, $^tBu_3P$, 2,2'-bis(diphenylphosphino)-1,1'-binaphthalene (BINAP), 1,1'-bis(diphenylphosphino)ferrocene (dppf) or 1,3-bis(2,6-dipropylphenyl)-1H-imidazol-3-ium chloride, can be used as a catalyst to improve the reaction efficiency.

As shown in Scheme II, compound of formula (7), wherein m is as defined herein, can react with compound of formula (5) under the conditions described in Scheme I to give compound of formula (8). Alternatively, compound of formula (8) can also be prepared by the reactions of compound of formula (7) with compound of formula (9), wherein $R^{1a}$ and $R^{1b}$ are selected from H, alkyl, cycloalkyl, aryl heteroaryl, or $R^{1a}$ and $R^{1b}$ together with the attached carbon atom to form a cycloalkyl or heterocycloalkyl ring. Compound of formula (8) can react with compound of formula (6) under the conditions described in Scheme I to give compound of formula (10). In the presence of an acid, such as but not limited to HCl or $CF_3CO_2H$, N-Boc group in compound of formula (10) can be deprotected to give compound of formula (11) that can further react with compound of formula (1) in the presence a base, such as but not limited to $K_2CO_3$, $Na_2CO_3$, $Cs_2CO_3$, NaH, t-BuONa, t-BuOK, $Et_3N$, or diisopropylethylamine (DIPEA), to give the compound of formula (1). If it is necessary, for example, when $R^1$ or $R^2$ is an aryl or heteroaryl, a palladium reagent, such as but not limited to $PdCl_2$, $Pd(OAc)_2$ $Pd_2(dba)_3$ or $Pd(PPh_3)_4$, and a ligand, such as but not limited to $Ph_3P$, $^tBu_3P$, 2,2'-bis(diphenylphosphino)-1,1'-binaphthalene (BINAP), 9,9-Dimethyl-4,5-bis(diphenylphosphino)xanthene (Xantphos), 1,1'-bis(diphenylphosphino)ferrocene (dppf) or 1,3-bis(2,6-dipropylphenyl)-1H-imidazol-3-ium chloride, can be used as a catalyst to improve the reaction efficiency.

Scheme III

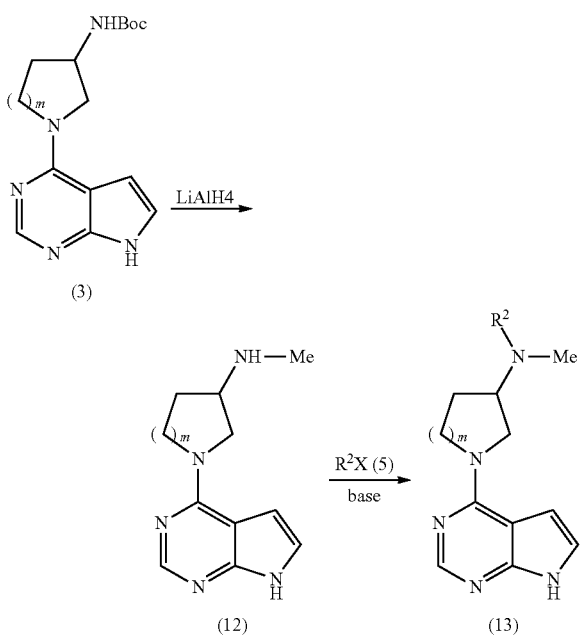

Scheme III shows that compound of formula (3) can react with LiAlH₄ to give compound of (12) that can further react with compound of formula (5) under similar conditions as described in Scheme I to give compound of formula (13).

The compounds thus obtained can be further modified at their peripheral positions to provide the desired compounds. Synthetic chemistry transformations are described, for example, in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

Before use, the at least one compound and/or at least one pharmaceutically acceptable salt described herein, can be purified by column chromatography, high performance liquid chromatography, crystallization, or other suitable methods.

Also provided is a composition comprising at least one compound and/or at least one pharmaceutically acceptable salt described herein, and at least one pharmaceutically acceptable carrier.

A composition comprising at least one compound and/or at least one pharmaceutically acceptable salt described herein, can be administered in various known manners, such as orally, parenterally, by inhalation spray, or via an implanted reservoir. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

An oral composition can be any orally acceptable dosage form including, but not limited to, tablets, capsules, emulsions, and aqueous suspensions, dispersions and solutions. Commonly used carriers for tablets include lactose and corn starch. Lubricating agents, such as magnesium stearate, are also typically added to tablets. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A sterile injectable composition (e.g., aqueous or oleaginous suspension) can be formulated according to techniques known in the art using suitable dispersing or wetting agents (such as, for example, Tween 80) and suspending agents. The sterile injectable Intermediate can also be a sterile injectable solution or suspension in a non-toxic parenterally acceptable diluent or solvent, for example, as a solution in 1,3-butanediol. Among the pharmaceutically acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or di-glycerides). Fatty acids, such as oleic acid and its glyceride derivatives are useful in the Intermediate of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents.

An inhalation composition can be prepared according to techniques well known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art.

A topical composition can be formulated in form of oil, cream, lotion, ointment and the like. Suitable carriers for the composition include vegetable or mineral oils, white petrolatum (white soft paraffin), branched chain fats or oils, animal fats and high molecular weight alcohols (greater than C12). In some embodiments, the pharmaceutically acceptable carrier is one in which the active ingredient is soluble. Emulsifiers, stabilizers, humectants and antioxidants may also be included as well as agents imparting color or fragrance, if desired. Additionally, transdermal penetration enhancers may be employed in those topical formulations. Examples of such enhancers can be found in U.S. Pat. Nos. 3,989,816 and 4,444,762.

Creams may be formulated from a mixture of mineral oil, self-emulsifying beeswax and water in which mixture the active ingredient, dissolved in a small amount of an oil, such as almond oil, is admixed. An example of such a cream is one which includes about 40 parts water, about 20 parts beeswax, about 40 parts mineral oil and about 1 part almond oil. Ointments may be formulated by mixing a solution of the active ingredient in a vegetable oil, such as almond oil, with warm soft paraffin and allowing the mixture to cool. An example of such an ointment is one which includes about 30% by weight almond oil and about 70% by weight white soft paraffin.

A pharmaceutically acceptable carrier refers to a carrier that is compatible with active ingredients of the composition (and in some embodiments, capable of stabilizing the active ingredients) and not deleterious to the subject to be treated. For example, solubilizing agents, such as cyclodextrins (which form specific, more soluble complexes with the at least one compound and/or at least one pharmaceutically acceptable salt described herein), can be utilized as pharmaceutical excipients for delivery of the active ingredients. Examples of other carriers include colloidal silicon dioxide, magnesium stearate, cellulose, sodium lauryl sulfate, and pigments such as D&C Yellow #10.

Suitable in vitro assays can be used to preliminarily evaluate the efficacy of the at least one compound and/or at least one pharmaceutically acceptable salt described herein, in inhibiting the activity of at least one kinase chosen from JAK1, JAK2, JAK3 and TYK2. The at least one compound and/or at least one pharmaceutically acceptable salt described herein, can further be examined for efficacy in treating cancer or inflammatory disease by in vivo assays. For example, the compounds described herein, and/or the pharmaceutically acceptable salts thereof, can be administered to an animal (e.g., a mouse model) having cancer or inflammatory disease and its therapeutic effects can be accessed. Based on the results, an appropriate dosage range and administration route for animals, such as humans, can also be determined.

Also provided is a method of inhibiting the activity of at least one kinase chosen from JAK1, JAK2, JAK3 and TYK2. The method comprises contacting the at least one kinase with an amount of at least one compound and/or at least one pharmaceutically acceptable salt described herein effective to inhibit the activity of the at least one kinase chosen from JAK1, JAK2, JAK3 and TYK2.

The at least one compound and/or at least one pharmaceutically acceptable salt described herein can be used to achieve a beneficial therapeutic or prophylactic effect, for example, in subjects with cancer. As used herein, the term "cancer" refers to a cellular disorder characterized by uncontrolled or disregulated cell proliferation, decreased cellular differentiation, inappropriate ability to invade surrounding tissue, and/or ability to establish new growth at ectopic sites. The term "cancer" includes, but is not limited to, solid tumors and bloodborne tumors. The term "cancer" encompasses diseases of skin, tissues, organs, bone, cartilage, blood, and vessels. The term "cancer" further encompasses primary and metastatic cancers.

Non-limiting examples of solid tumors include pancreatic cancer; bladder cancer; colorectal cancer; breast cancer, including metastatic breast cancer; prostate cancer, including androgen-dependent and androgen-independent prostate cancer; renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; skin cancer, including e.g., malignant melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; soft tissue sarcoma; and thyroid carcinoma.

Non-limiting examples of hematologic malignancies include acute myeloid leukemia (AML); chronic myelogenous leukemia (CML), including accelerated CML and CML blast phase (CML-BP); acute lymphoblastic leukemia (ALL); chronic lymphocytic leukemia (CLL); Hodgkin's disease (HD); non-Hodgkin's lymphoma (NHL), including follicular lymphoma and mantle cell lymphoma; B-cell lymphoma; T-cell lymphoma; multiple myeloma (MM); Waldenstrom's macroglobulinemia; myelodysplastic syndromes (MDS), including refractory anemia (RA), refractory anemia with ringed sideroblasts (RARS), (refractory anemia with excess blasts (RAEB), and RAEB in transformation (RAEB-T); and myeloproliferative syndromes.

In some embodiments, the examples of the cancer to be treated include, but are not limited to, lung cancer, head and neck cancer, colorectal cancer, pancreatic cancer, colon cancer, breast cancer, ovarian cancer, prostate cancer, stomach cancer, kidney cancer, liver cancer, brain cancer, bone cancer, and leukemia.

The at least one compound and/or at least one pharmaceutically acceptable salt described herein can be used to achieve a beneficial therapeutic or prophylactic effect, for example, in subjects with an inflammatory disease or inflammatory disorder. The term "inflammatory disease" or "inflammatory disorder" refers to pathological states resulting in inflammation, typically caused by neutrophil chemotaxis. Examples of such disorders include inflammatory skin diseases including psoriasis and atopic dermatitis; systemic scleroderma and sclerosis; responses associated with inflammatory bowel disease (IBD) (such as Crohn's disease and ulcerative colitis); ischemic reperfusion disorders including surgical tissue reperfusion injury, myocardial ischemic conditions such as myocardial infarction, cardiac arrest, reperfusion after cardiac surgery and constriction after percutaneous transluminal coronary angioplasty, stroke, and abdominal aortic aneurysms; cerebral edema secondary to stroke; cranial trauma, hypovolemic shock; asphyxia; adult respiratory distress syndrome; acute-lung injury; Behcet's Disease; dermatomyositis; polymyositis; multiple sclerosis (MS); dermatitis; meningitis; encephalitis; uveitis; osteoarthritis; lupus nephritis; autoimmune diseases such as rheumatoid arthritis (RA), Sjorgen's syndrome, vasculitis; diseases involving leukocyte diapedesis; central nervous system (CNS) inflammatory disorder, multiple organ injury syndrome secondary to septicaemia or trauma; alcoholic hepatitis; bacterial pneumonia; antigen-antibody complex mediated diseases including glomerulonephritis; sepsis; sarcoidosis; immunopathologic responses to tissue/organ transplantation; inflammations of the lung, including pleurisy, alveolitis, vasculitis, pneumonia, chronic bronchitis, bronchiectasis, diffuse panbronchiolitis, hypersensitivity pneumonitis, idiopathic pulmonary fibrosis (IPF), and cystic fibrosis; etc. The preferred indications include, without limitation, chronic inflammation, autoimmune diabetes, rheumatoid arthritis (RA), rheumatoid spondylitis, gouty arthritis and other arthritic conditions, multiple sclerosis (MS), asthma, systemic lupus erythrematosus, adult respiratory distress syndrome, Behcet's disease, psoriasis, chronic pulmonary inflammatory disease, graft versus host reaction, Crohn's Disease, ulcerative colitis, inflammatory bowel disease (IBD), Alzheimer's disease, and pyresis, along with any disease or disorder that relates to inflammation and related disorders.

The at least one compound and/or at least one pharmaceutically acceptable salt described herein can be used to achieve a beneficial therapeutic or prophylactic effect, for example, in subjects with an autoimmune disease. The term "autoimmune disease" refers to a disease or disorder arising from and/or directed against an individual's own tissues or organs, or a co-segregate or manifestation thereof, or resulting condition therefrom. Examples of autoimmune diseases include, but are not limited to, lupus, myasthenia gravis, multiple sclerosis (MS), rheumatoid arthritis (RA), psoriasis, inflammatory bowel disease, asthma and idiopathic thrombocytopenic purpura, and myeloid proliferative disorder, such as myelofibrosis, PV/ET (Post-Polycythemia/Essential Thrombocythemia Myelofibrosis).

In some embodiments, the at least one compound and/or at least one pharmaceutically acceptable salt described herein, is administered in conjunction with another therapeutic agent. In some embodiments, the other therapeutic agent is one that is normally administered to patients with the disease or condition being treated. For example, the other therapeutic agent may be an anti-inflammatory agent or an anti-neoplastic agent, depending on the disease or condition being treated. The at least one compound and/or at least one pharmaceutically acceptable salt described herein, may be administered with the other therapeutic agent in a single dosage form or as a separate dosage form. When administered as a separate dosage form, the other therapeutic agent may be administered prior to, at the same time as, or following administration of the at least one compound and/or at least one pharmaceutically acceptable salt described herein.

In some embodiments, at least one compound and/or at least one pharmaceutically acceptable salt described herein, is administered in conjunction with an anti-inflammatory agent. Nonlimiting examples of anti-inflammatory agents include corticosteroids (e.g., fluticasone propionate, beclomethasone dipropionate, mometasone furoate, triamcinolone acetonide or budesonide), disease-modifying agents (e.g., antimalarials, methotrexate, sulfasalazine, mesalamine, azathioprine, 6-mercaptopurine, metronidazole, injectable and oral gold, or D-penicillamine), non-steroidal antiinflammatory drugs (e.g., acetominophen, aspirin, sodium salicylate, sodium cromoglycate, magnesium salicylate, choline magnesium salicylate, salicylsalicylic acid, ibuprofen, naproxen, diclofenac, diflunisal, etodolac, fenoprofen calcium, fluriprofen, piroxicam, indomethacin, ketoprofen, ketorolac tromethamine, meclofenamate, meclofenamate sodium, mefenamic acid, nabumetone, oxaprozin, phenyl butyl nitrone (PBN), sulindac, or tolmetin), COX-2 inhibitors, inhibitors of cytokine synthesis/release (e.g., anti-cytokine antibodies, anti-cytokine receptor antibodies, and the like).

In some embodiments, at least one compound and/or at least one pharmaceutically acceptable salt described herein, is administered in conjunction with an anti-neoplastic agent. As used herein, the term "anti-neoplastic agent" refers to any agent that is administered to a subject with cancer for purposes of treating the cancer. Nonlimiting examples of anti-neoplastic agents include: radiotherapy; immunotherapy; DNA damaging chemotherapeutic agents; and chemotherapeutic agents that disrupt cell replication.

Non-limiting examples of DNA damaging chemotherapeutic agents include topoisomerase I inhibitors (e.g., irinotecan, topotecan, camptothecin and analogs or metabolites thereof, and doxorubicin); topoisomerase II inhibitors (e.g., etoposide, teniposide, and daunorubicin); alkylating agents (e.g., melphalan, chlorambucil, busulfan, thiotepa, ifosfamide, carmustine, lomustine, semustine, streptozocin, decarbazine, methotrexate, mitomycin C, and cyclophosphamide); DNA intercalators (e.g., cisplatin, oxaliplatin, and carboplatin); DNA intercalators and free radical generators such as bleomycin; and nucleoside mimetics (e.g., 5-fluorouracil, capecitibine, gemcitabine, fludarabine, cytarabine, mercaptopurine, thioguanine, pentostatin, and hydroxyurea).

Chemotherapeutic agents that disrupt cell replication include: paclitaxel, docetaxel, and related analogs; vincristine, vinblastin, and related analogs; thalidomide and related analogs (e.g., CC-5013 and CC-4047); protein tyrosine kinase inhibitors (e.g., imatinib mesylate and gefitinib); proteasome inhibitors (e.g., bortezomib); NF-kappa B inhibitors, including inhibitors of I kappa B kinase; antibodies which bind to proteins overexpressed in cancers and thereby downregulate cell replication (e.g., trastuzumab, rituximab, cetuximab, and bevacizumab); and other inhibitors of proteins or enzymes known to be upregulated, over-expressed or activated in cancers, the inhibition of which downregulates cell replication.

EXAMPLES

The examples below are intended to be purely exemplary and should not be considered to be limiting in any way. Efforts have been made to ensure accuracy with respect to numbers used (for example, amounts, temperature, etc.) but some experimental errors and deviations should be accounted for. Unless indicated otherwise, parts are parts by weight, temperature is in degrees Centigrade, and pressure is at or near atmospheric. All MS data were checked by agilent 6120 and/or agilent 1100. All reagents, except intermediates, used in this invention are commercially available. All compound names except the reagents were generated by Chemdraw 8.0.

In the following examples, the abbreviations below are used:

AIBN a,a'-azo-isobutyronnitrile
BINAP 2,2'-Bis(diphenylphosphino)-1,1'-binaphthyl
Boc tert-butoxycarbonyl
$Boc_2O$ di-t-butyl-dicarbonate
i-$BuNO_2$ isobutylnitrite
BTC bis(trichloromethyl)carbonate
DCM dichloromethane
DIPEA N,N-diisopropylethylamine
DMF N,N-dimethylformamide
DMAP 4-dimethylaminopyridine
DPPA diphenylphosphoryl azide
DBU 1,8-diazabicyclo[5.4.0]undec-7-ene
$Et_3N$ triethylamine
h hour
HATU O-(7-azabenzotriazol-1-yl)-N,N,N',N'-tetramethyluronium hexafluorophosphate
HMTA Hexamethylenetetramine
HOAc acetic acid
Lawesson's reagent: 2,4-Bis(4-methoxyphenyl)-2,4-dithioxo-1,3,2,4-dithiadiphosphetane
mL milliliter(s)
min minute(s)
MeOH methanol
MsCl methanesulfonyl chloride
NBS N-bromosuccinimide
PE petroleum ether
Pd(dppf)$Cl_2$ 1,1'-Bis(diphenylphosphino)ferrocene-palladium(II)dichloride
Pd(dppf)$Cl_2$.$CH_2Cl_2$ 1,1'-Bis(diphenylphosphino)ferrocene-palladium(II)dichloride dichloromethane complex
$Pd_2(dba)_3$ tris(dibenzylideneacetone)dipalladium(0)
Pd(PPh$_3$)$_4$ tetrakis(triphenylphosphine)palladium(0)
PdCl$_2$(PPh$_3$)$_2$ Bis(triphenylphosphine)palladium(II)dichloride
PPh$_3$ triphenylphosphine
THF tetrahydrofuran
TFA trifluoroacetic acid
TBTU o-benzotriazol-1-yl-N,N,N',N'-tetramethyluronium tetrafluoroborate

Intermediate 1

(R)-tert-butyl 3-(cyclopentyl)(prop-2-ynyl)amino)pyrrolidine-1-carboxylate

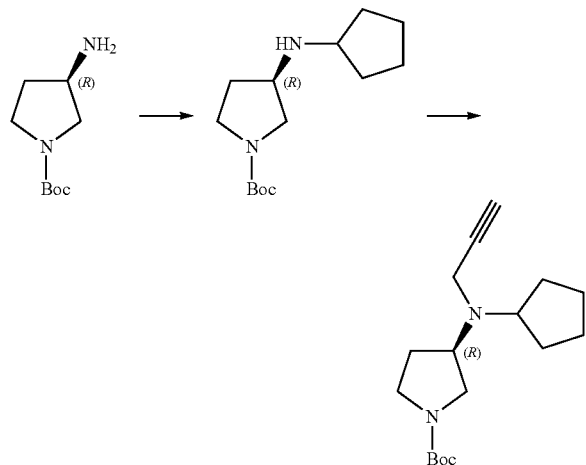

(A) (R)-butyl 3-(cyclopentylamino)pyrrolidine-1-carboxylate

To a solution of (R)-tert-butyl 3-aminopyrrolidine-1-carboxylate (1.0 g, 5.3 mmol) and cyclopentanone (451 mg, 5.3 mmol) in THF (20 mL) was slowly added NaBH(OAc)$_3$ (1.13 g, 5.3 mmol) and then stirred at the ambient temperature for overnight. The reaction was quenched with H$_2$O (20 mL) and extracted with dichloromethane (3×20 mL). The combined extracts were washed with brine (3×5 mL), dried over anhydrous Na$_2$SO$_4$, filtered and concentrated to give the title compound. MS (m/z): 255 (M+H)$^+$.

(B) (R)-tert-butyl 3-(cyclopentyl(prop-2-ynyl)amino)pyrrolidine-1-carboxylate A mixture of (R)-tert-butyl 3-(cyclopentylamino)pyrrolidine-1-carboxylate (200 mg, 0.78 mmol), 3-bromo-1-propyne (140 mg, 1.18 mmol) and K$_2$CO$_3$ (217 mg, 1.57 mmol) in acetonitrile (3 mL) was stirred at reflux for overnight. The volatiles were removed under reduced pressure. The residue was purified by chromatography on silica gel (PE/EtOAc=4:1) to give the title compound. MS (m/z): 293 (M+H)$^+$.

Intermediate 2

(R)—N-methyl-1-(7H-pyrrolo[2,3-d]-pyrimidin-4-yl) pyrrolidin-3-amine

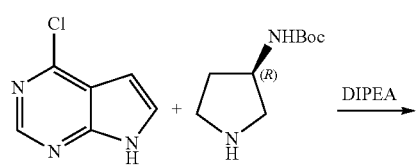

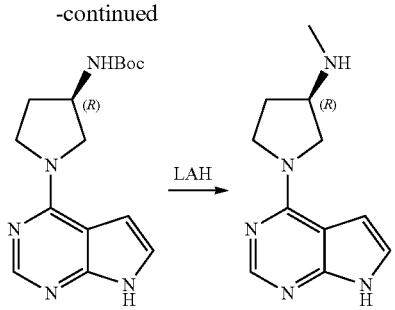

(A) (R)-tert-butyl 1-(7H-pyrrolo[2,3-d]pyrimidin-4-yl) pyrrolidin-3-ylcarbamate A mixture of (R)-tert-butyl pyrrolidin-3-ylcarbamate (250 mg, 1.34 mmol), 4-chloro-7H-pyrrolo[2,3-d]pyrimidine (206 mg, 1.34 mmol) and DIPEA (0.35 mL, 2.01 mmol) in EtOH (3 mL) was stirred at reflux temperature for 16 hours. The volatiles were removed under reduced pressure. The residue was dissolved in EtOAc (15 mL), and filtered. The filtrate was washed with brine (3×5 mL), dried over anhydrous Na$_2$SO$_4$, and concentrated to give the title compound (360 mg, 88% yield). MS (m/z): 304 (M+H)$^+$.

(B) (R)—N-methyl-1-(7H-pyrrolo[2,3-d]-pyrimidin-4-yl) pyrrolidin-3-amine

Under N$_2$, to a solution of (R)-tert-butyl 1-(7H-pyrrolo[2,3-d]pyrimidin-4-yl) pyrrolidin-3-ylcarbamate (380 mg, 1.34 mmol) in anhydrous THF (10 mL) was slowly added Lithium aluminium hydride (143 mg, 3.76 mmol) at 0° C. After the completion of the addition, the reaction mixture was stirred at 65° C. for 2 hours. The reaction mixture was then cooled to 0° C., quenched with aqueous NaOH (15%), and filtrated to remove the solid. The filtrate was concentrated under reduced pressure. The residue was purified by preparative TLC to give the title compound (178 mg, 66% yield). MS (m/z): 218 (M+H)$^+$.

Intermediate 3

(R) 1-(7H-pyrrolo[2,3-d]pyrimidin-4-yl)pyrrolidin-3-amine hydrochloride

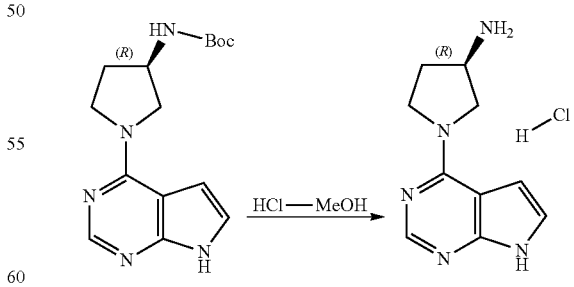

(R)-tert-butyl 1-(7H-pyrrolo[2,3-d]pyrimidin-4-yl)pyrrolidin-3-ylcarbamate (600 mg, 1.97 mmol) was treated with HCl (in MeOH, 6 N, 5 mL) at the ambient temperature for 2 h. The volatiles were removed under reduced pressure to give (R)-1-(7H-pyrrolo[2,3-d]pyrimidin-4-yl)pyrrolidin-3-amine hydrochloride salt. MS (m/z): 204 (M+H)$^+$.

27

Intermediate 4

(R)—N-propyl-1-(7H-pyrrolo[2,3-d]pyrimidin-4-yl)pyrrolidin-3-amine

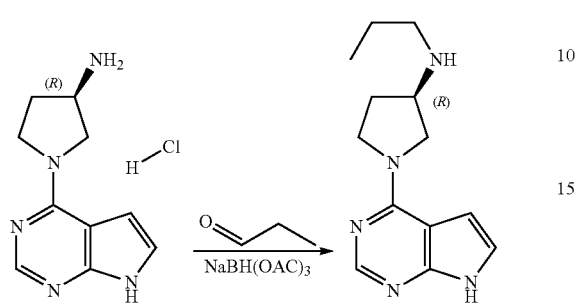

A mixture of (R)-1-(7H-pyrrolo[2,3-d]pyrimidin-4-yl)pyrrolidin-3-amine hydrochloride (50 mg, 0.24 mmol), propionaldehyde (15 mg, 0.26 mmol) and NaBH(OAC)$_3$ (61 mg, 1.2 mmol) in THF (5 mL) was stirred at the ambient temperature for 20 minutes. It was then quenched with water (2 mL) and extracted with EtOAc (3×10 mL). The combined extracts were washed with brine (3×5 mL), dried over anhydrous Na$_2$SO$_4$, filtered, and concentrated to give the title compound. MS (m/z): 246 (M+H)$^+$.

Intermediate 5

(R)-6-(1-(7-((2-(trimethylsilyl)ethoxy)methyl)-7H-pyrrolo[2,3-d]pyrimidin-4-yl)pyrrolidin-3-ylamino)nicotinonitrile

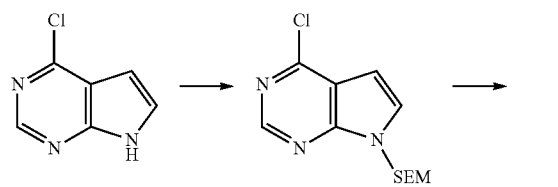

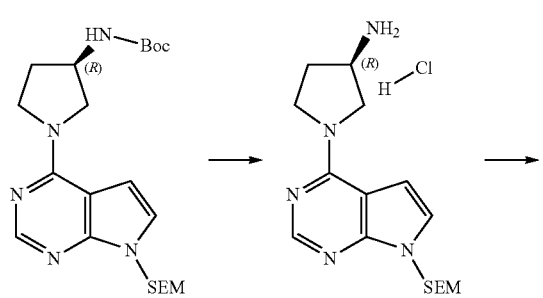

28

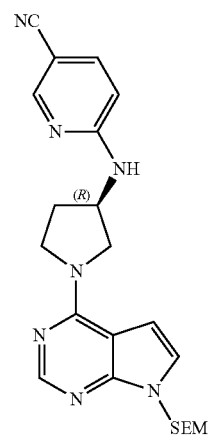

(A) 4-chloro-7-((2-(trimethylsilyl)ethoxy)methyl)-7H-pyrrolo-[2,3-d]pyrimidine

To a solution of 4-chloro-7H-pyrrolo[2,3-d]pyrimidine (5 g, 32.6 mmol) in THF (50 mL) was added NaH (30%, 4 g, 50.0 mmol) at 0° C. The reaction mixture was stirred at 0° C. for 1 hour before the addition of (2-(chloromethoxy)ethyl)-trimethylsilane (15 g, 90.0 mmol). The reaction was stirred at ambient temperature for 3 hours. It was then treated with water (5 mL) and extracted with EtOAc. The organic layer was concentrated under reduced pressure, and the residue was purified by chromatography to give the title compound. MS (m/z): 284 (M+H)$^+$ ($^{35}$Cl), 286 (M+H)$^+$ ($^{37}$Cl).

(B) (R)-tert-butyl 1-(7-((2-(trimethylsilyl)ethoxy)methyl)-7H-pyrrolo[2,3-d]pyrimidin-4-yl)pyrrolidin-3-ylcarbamate A solution of 4-chloro-7-((2-(trimethylsilyl)ethoxy)methyl)-7H-pyrrolo [2,3-d]pyrimidine (900 mg, 3.17 mmol), (R)-tert-butyl pyrrolidin-3-ylcarbamate (709 mg, 3.80 mmol) and DIPEA (618 mg, 4.75 mmol) in EtOH (20 mL) was stirred at refluxed temperature for 3 hours. The volatiles were removed under reduced pressure and the residue was dissolved in EtOAc (100 mL), washed with brine (3×10 mL), dried over anhydrous Na$_2$SO$_4$, filtered, and concentrated under reduced pressure to give the tile compound. MS (m/z): 434 (M+H)$^+$.

(C) (R)-6-(1-(7-((2-(trimethylsilyl)ethoxy)methyl)-7H-pyrrolo[2,3-d]pyrimidin-4-yl)pyrrolidin-3-ylamino)nicotinonitrile A solution of (R)-tert-butyl 1-(7-((2-(trimethylsilyl)ethoxy)methyl)-7H-pyrrolo[2,3-d]pyrimidin-4-yl)pyrrolidin-3-ylcarbamate (700 mg, 1.61 mmol) in HCl (in MeOH, 6 N, 5 mL) was stirred at ambient temperature for 3 hours. The volatiles were removed under reduced pressure. The residue was dissolved in DMSO (3 mL). 6-chloronicotinonitrile (323 mg, 2.41 mmol), KI (10 mg, 0.06 mmol) and DIPEA (311 mg, 2.41 mmol) were then added. The reaction mixture was stirred at 120° C. for 14 h, cooled to ambient temperature, diluted with H$_2$O (20 mL), and extracted with EtOAc (3×40 mL). The combined extracts were washed with brine (3×10 mL), dried over anhydrous Na$_2$SO$_4$, filtered and concentrated under reduced pressure. The residue was purified by chromatography to give the title compound. MS (m/z): 436 (M+H)$^+$.

Intermediate 6

(R)—N-methyl-1-(7-((2-(trimethylsilyl)ethoxy)methyl)-7H-pyrrolo[2,3-d]pyrimidin-4-yl)pyrrolidin-3-amine

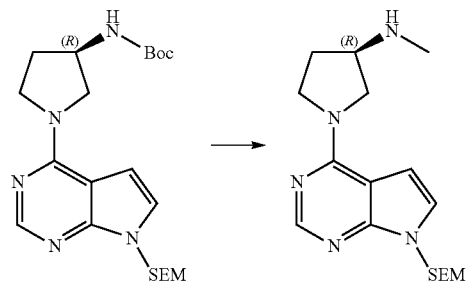

The title compound was prepared according to the procedures of Intermediate 2(B) using (R)-tert-butyl 1-(7-((2-(trimethylsilyl)ethoxy)methyl)-7H-pyrrolo[2,3-d]pyrimidin-4-yl)pyrrolidin-3-ylcarbamate. MS (m/z): 348 (M+H)$^+$.

Intermediate 7

(R)-5-bromo-N-methyl-N-(1-(7-((2-(trimethylsilyl)ethoxy)methyl)-7H-pyrrolo[2,3-d]pyrimidin-4-yl)pyrrolidin-3-yl)pyrazin-2-amine

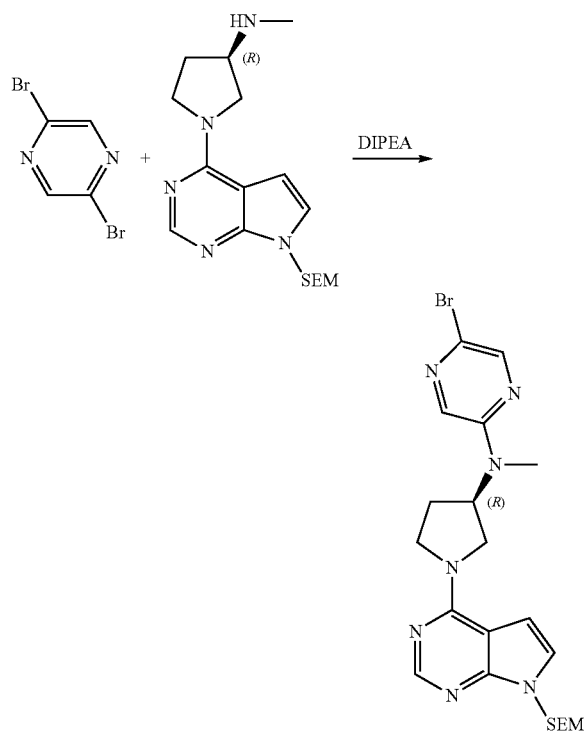

DIPEA (2.876 mmol) was added to the solution of (R)—N-methyl-1-(7-((2-(trimethylsilyl)ethoxy)methyl)-7H-pyrrolo[2,3-d]pyrimidin-4-yl)pyrrolidin-3-amine (0.575 mmol) and 2,5-dibromopyrazine (0.689 mmol) in NMP (2 mL). Then it was heated at 200° C. for 45 min in a microwave reactor. After cooling, it was poured into water, and extracted with EtOAc. The combined organic layer was concentrated, and the resulting residue was purified by column chromatography to give (R)-5-bromo-N-methyl-N-(1-(7-((2-(trimethylsilyl)ethoxy)methyl)-7-pyrrolo[2,3-d]pyrimidin-4-yl)pyrrolidin-3-yl)pyrazin-2-amine in 57.5% yield. MS (m/z): 504 (M+H)$^+$, 506 (M+H)$^+$.

Intermediate 8

(R)—N$^2$-Methyl-N$^2$-{1-[7-(2-trimethylsilanyl-ethoxymethyl)-7H-pyrrolo[2,3-d]pyrimidin-4-yl]-pyrrolidin-3-yl}-pyridine-2,5-diamine

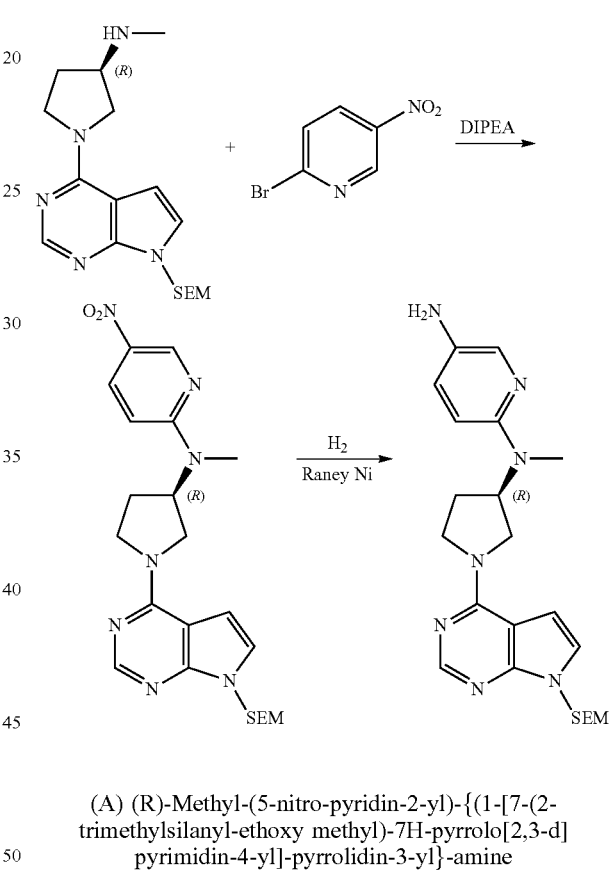

(A) (R)-Methyl-(5-nitro-pyridin-2-yl)-{(1-[7-(2-trimethylsilanyl-ethoxy methyl)-7H-pyrrolo[2,3-d]pyrimidin-4-yl]-pyrrolidin-3-yl}-amine A mixture of (R)-Methyl-{1-[7-(2-trimethylsilanyl-ethoxymethyl)-7H-pyrrolo[2,3-d]pyrimidin-4-yl]-pyrrolidin-3-yl}-amine (10 mmol), DIPEA (20 mmol) and 2-bromo-5-nitro-pyridine (11 mmol) in DMF (50 mL) was stirred at 100° C. for 24 hours. After cooling, it was poured into water and extracted with EtOAc. The organic layer was washed with water and brine sequentially, and then concentrated to give crude product. The crude product was purified by column chromatography to give the title compound.

(B) (R)—N$^2$-Methyl-N$^2$-{1-[7-(2-trimethylsilanyl-ethoxymethyl)-7H-pyrrolo[2,3-d]pyrimidin-4-yl]-pyrrolidin-3-yl}-pyridine-2,5-diamine To a solution of (R)-methyl-(5-nitro-pyridin-2-yl)-{1-[7-(2-trimethylsilanyl-ethoxymethyl)-7H-pyrrolo[2,3-d]pyrimidin-4-yl]-pyrrolidin-3-yl}-amine (10 mmol) in methanol (100 mL) was added Raney Ni. The mixture was stirred at room temperature for 18 hours under 1 atm of H$_2$. After filtration, it was concentrated to give the title compound.

Intermediate 9

(R)-tert-butyl 3-((5-cyanopyridin-2-yl)(cyclopropyl)amino)pyrrolidine-1-carboxylate

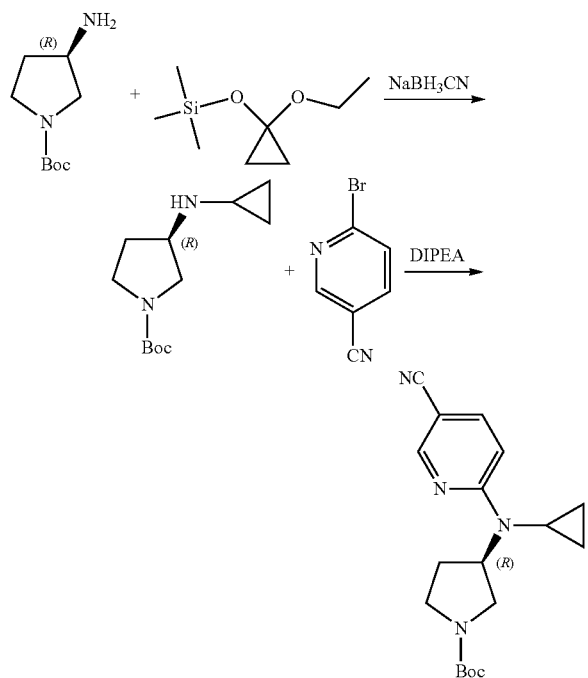

(A) (R)-tert-butyl 3-(cyclopropylamino)pyrrolidine-1-carboxylate

To a solution of (R)-tert-butyl 3-aminopyrrolidine-1-carboxylate (400 mg, 2.15 mmol), (1-ethoxycyclopropoxy)trimethylsilane (1500 mg, 8.60 mmol) in methanol (30 mL) was added sodium cyanoborohydride (569 mg, 8.60 mmol) and acetic acid (0.2 mL). The mixture was stirred at reflux for 10 h. The volatiles were removed under reduced pressure. The residue was treated with water (20 mL) and extracted with ethyl acetate (3×30 mL). The combined extracts were washed with brine (3×10 mL), dried over anhydrous Na$_2$SO$_4$, filtered, and concentrated to give the title compound. MS (m/z): 227 (M+H)$^+$.

(B) (R)-tert-butyl 3-((5-cyanopyridin-2-yl)(cyclopropyl)amino)pyrrolidine-1-carboxylate The title compound was prepared according to the procedures of Intermediate 2 (A) using (R)-tert-butyl 3-(cyclopropylamino)pyrrolidine-1-carboxylate and 6-bromonicotinonitrile under similar conditions MS (m/z): 329 (M+H)$^+$.

Intermediate 10 tert-butyl 3-(5-cyanoindolin-1-yl)pyrrolidine-1-carboxylate

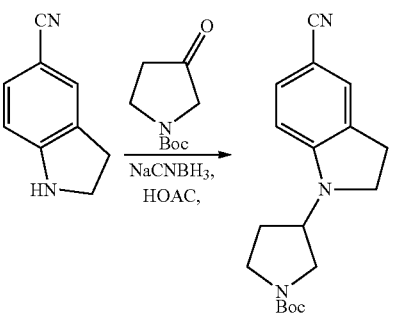

To a solution of indoline-5-carbonitrile (110 mg, 0.75 mmol) in 2.5 mL of MeOH was added tert-butyl 3-oxopyrrolidine-1-carboxylate (166 mg, 0.90 mmol) and HOAc (0.11 mL, 1.88 mmol) subsequently. After stirring at room temperature for 10 minutes, NaCNBH$_3$ (57 mg, 0.90 mmol) was added and the mixture was then stirred at ambient temperature for 2 days. The volatiles were removed under vacuum. The residue was diluted with EtOAc, then washed with 1 N NaOH solution and brine, dried over Na$_2$SO$_4$, and evaporated in vacuo to afford the crude title compound for the next step use without further purification.

Intermediate 11

(R)-tert-butyl 3-((5-cyano-6-methoxypyridin-2-yl)(methyl)amino)pyrrolidine-1-carboxylate

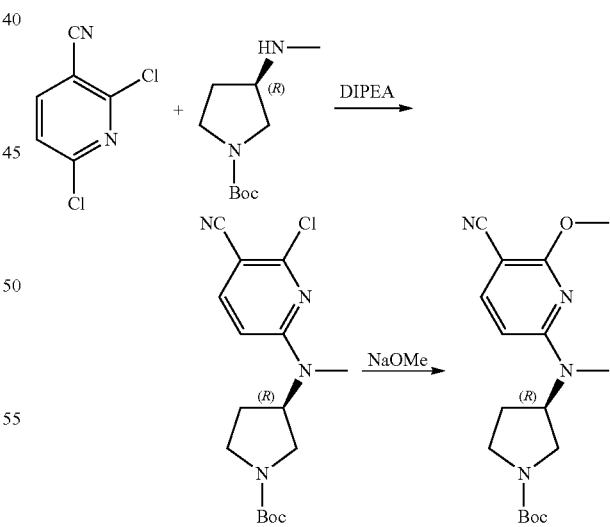

(A) (R)-tert-butyl 3-((6-chloro-5-cyanopyridin-2-yl)(methyl)amino) pyrrolidine-1-carboxylate To a solution of 2, 6-dichloronicotinonitrile (2.2 mmol) and DIPEA (10 mmol) in DMF (10 mL) was added (R)-tert-butyl 3-(methylamino) pyrrolidine-1-carboxylate with stirring at room temperature. The reaction mixture was stirred at 100° C. overnight. Then the mixture was diluted with EtOAc, washed 3 times with water, dried, filtered and concentrated. The crude product was purified by flash chromatography to give the title compound.

(B) (R)-tert-butyl 3-((5-cyano-6-methoxypyridin-2-yl)(methyl)amino)pyrrolidine-1-carboxylate To a solution of (R)-tert-butyl 3-((6-chloro-5-cyanopyridin-2-yl)(methyl)amino) pyrrolidine-1-carboxylate (0.45 mmol) in MeOH (20 mL) was added the solution of NaOMe (0.9 mmol) in MeOH (2 mL). The reaction mixture was stirred at room temperature for 3 hours, then heated to 50° C., stirred for another 2 hours, then stirred at reflux overnight. The mixture was concentrated, diluted with EtOAc, washed with brine, dried, filtered, and concentrated to give the title compound.

The following intermediates 12-14 were prepared according to the procedures of Intermediate 11 (A) using the corresponding intermediates and reagents under appropriate conditions that could be recognized by one skilled in the art.

Intermediate 12

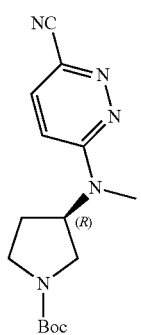

(R)-tert-butyl-3-((6-cyanopyridazin-3-yl)(methyl)amino)pyrrolidine-1-carboxylate Intermediate 13

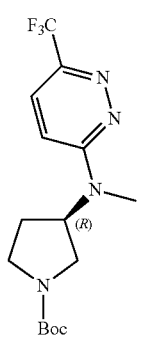

(R)-tert-butyl 3-(methyl(6-(trifluoromethyl)-pyridazin-3-yl)-amino)pyrrolidine-1-carboxylate Intermediate 14

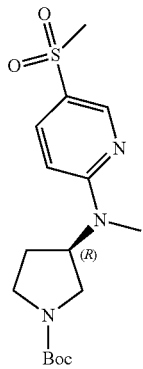

(R)-tert-butyl 3-(methyl(5-(methylsulfonyl)pyridin-2-yl)amino)-pyrrolidine-1-carboxylate Intermediate 15

(R)-tert-butyl 3-(N-methylcyloropanesulfonamido)pyrrolidine-1-carboxylate

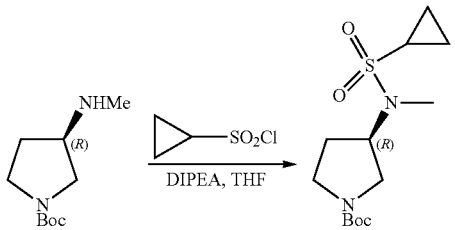

To a solution of (R)-tert-butyl 3-(methylamino)pyrrolidine-1-carboxylate (100 mg, 0.5 mmol) in 2.5 mL THF was added cyclopropanesulfonyl chloride (77 mg, 0.55 mmol) and DIPEA (0.10 mL, 0.60 mmol) at ambient temperature. The mixture was stirred at ambient temperature overnight. Water was added, and then extracted with EtOAc. The organic layers were combined washed with brine, dried over Na$_2$SO$_4$, and evaporated in vacuo to afford the crude title product which was used for the next step without further purification. MS (m/z): 305 (M+H)$^+$.

Intermediate 16

(R)-tert-butyl N-methylcyclopropanesulfonamido)pyrrolidine-1-carboxylate

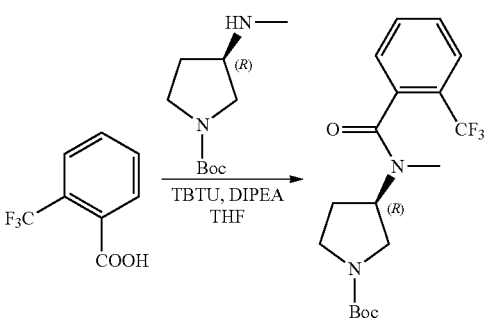

To a solution of (R)-tert-butyl 3-(methylamino)pyrrolidine-1-carboxylate (1 mmol), was slowly added TBTU (1.2 mmol), DIPEA (2 mmol) and 2-(trifluoromethyl)benzoic acid (1 mmol). The mixture was stirred at room temperature overnight. It was then concentrated. The residue was diluted with water, and extracted with EtOAc. The combined extracts were concentrated to give the title compound for the next step use without further purification.

Example 1: Synthesis of Compounds 1-260

Compound 1

(R)—N-(1-(7H-pyrrolo[2,3-d]pyrimidin-4-yl)pyrrolidin-3-yl)-2-cyano-N-methylacetamide

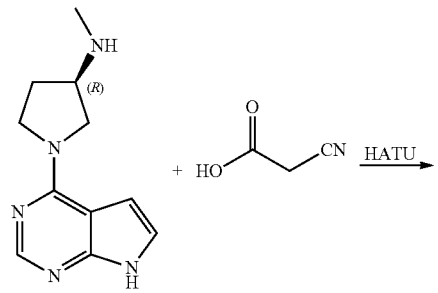

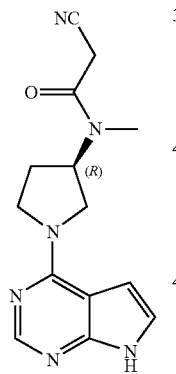

To a solution of (R)—N-methyl-1-(7H-pyrrolo[2,3-d]pyrimidin-4-yl)pyrrolidin-3-amine (75 mg, 0.345 mmol) and 2-cyanoacetic acid (35 mg, 0.414 mmol) in THF (5 mL) were added HATU (157 mg, 0.414 mmol) and DIPEA (0.12 mL, 0.69 mmol). The reaction mixture was stirred at room temperature for 20 hours. The precipitate was filtered, washed with EtOAc, and dried under reduced pressure to give the title compound (45 mg, 46%). MS (m/z): 285 (M+H)+.

The following compounds were prepared according to the procedures of Compound 1 using the corresponding intermediates and reagents under appropriate conditions that could be recognized by one skilled in the art.

| Compound | Structure | MS (m/z) (M + H)+ |
|---|---|---|
| 2 | 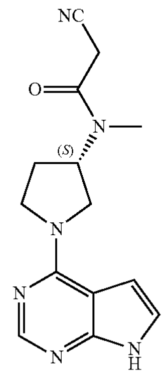 | 285 |
| 3 | 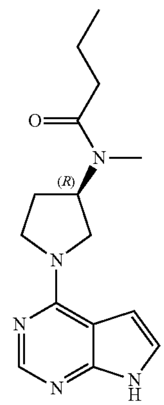 | 288 |
| 4 | 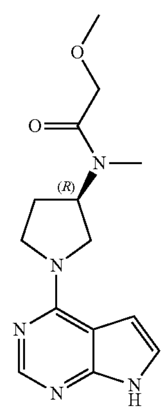 | 290 |
| 5 | 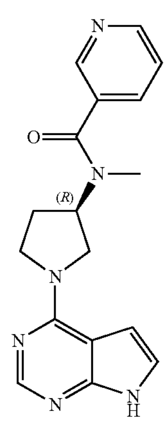 | 323 |

-continued

| Compound | Structure | MS (m/z) (M + H)+ |
|---|---|---|
| 6 | 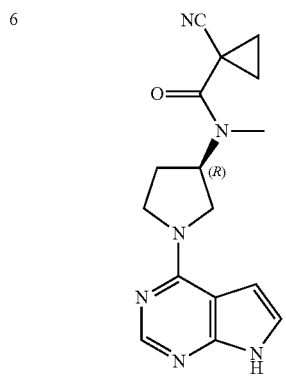 | 311 |
| 7 | 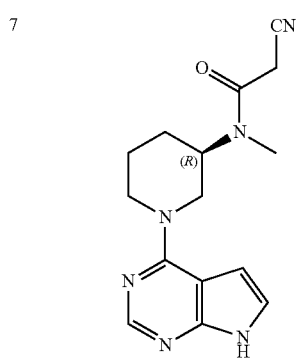 | 299 |
| 8 | 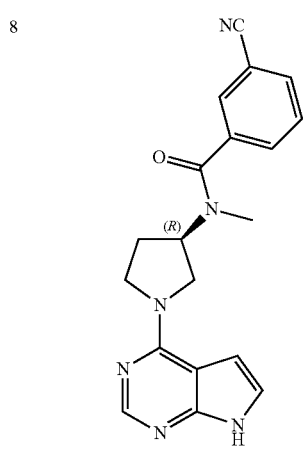 | 347 |

Compound 9

(R)—N-(1-(7H-pyrrolo[2,3]pyrimidin-4-yl)pyrrolidin-3-yl-4-cyano-N Methylbenzenesulfonamide

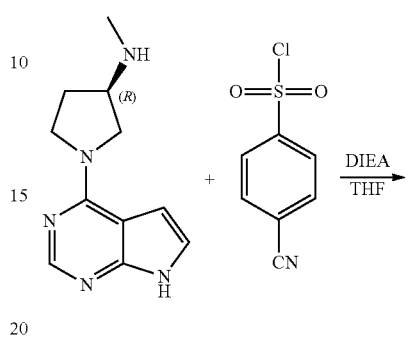

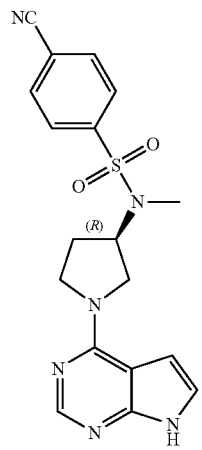

To a solution of (R)—N-methyl-1-(7H-pyrrolo[2,3-d]pyrimidin-4-yl)pyrrolidin-3-amine (30 mg, 0.138 mmol) in THF (2 mL) were added 4-cyanobenzene-1-sulfonyl chloride (42 mg, 0.208 mmol) and DIPEA (36 mg, 0.28 mmol). The reaction mixture was stirred at room temperature for 0.5 hour. The reaction mixture was then diluted with water, and extracted with EtOAc. The organic layers were combined, dried, and concentrated. The residue was purified by preparative TLC to give the title compound (13.6 mg, 26%). MS (m/z): 383 (M+H)+.

The following compounds were prepared according to the procedures of Compound 9 using the corresponding intermediates and reagents under appropriate conditions that could be recognized by one skilled in the art.

| Compound | Structure | MS (m/z) (M + H)+ |
|---|---|---|
| 10 | 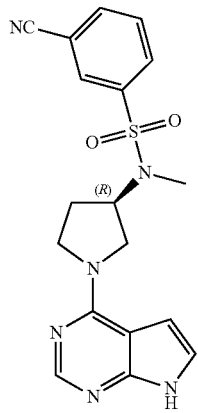 | 383 |
| 11 | 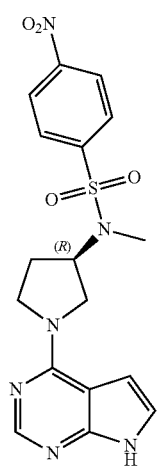 | 403 |
| 12 | 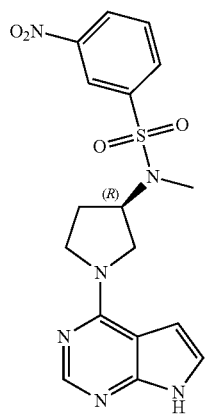 | 403 |
-continued
| Compound | Structure | MS (m/z) (M + H)+ |
|---|---|---|
| 13 | 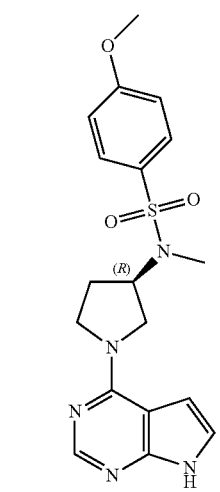 | 388 |
| 14 | 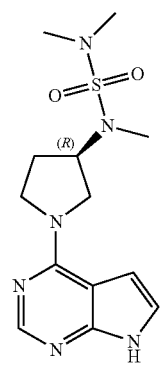 | 325 |
| 15 | 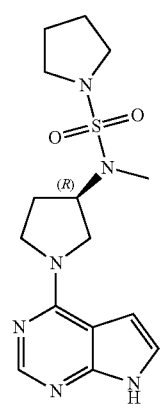 | 351 |

Compound 16

(R)-1-(1-(7H-pyrrolo[2,3-d]pyrimidin-4-yl)pyrrolidin-3-yl)-3-(3-cyanophenyl)-1-methylurea

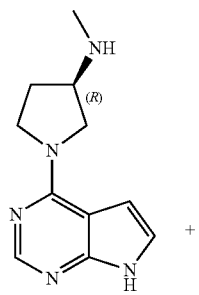

| Compound | Structure | MS (m/z) (M + H)+ |
|---|---|---|
| 17 | 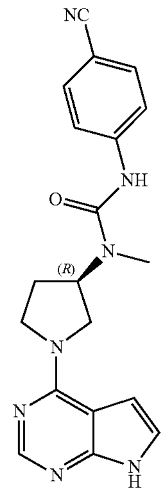 | 362 |

Compound 18

(R)—N-(1-(7H-pyrrolo[2,3-d]pyrimidin-4-yl)pyrrolidin-3-yl)-N-methyl-2-(trifluoromethyl)benzamide

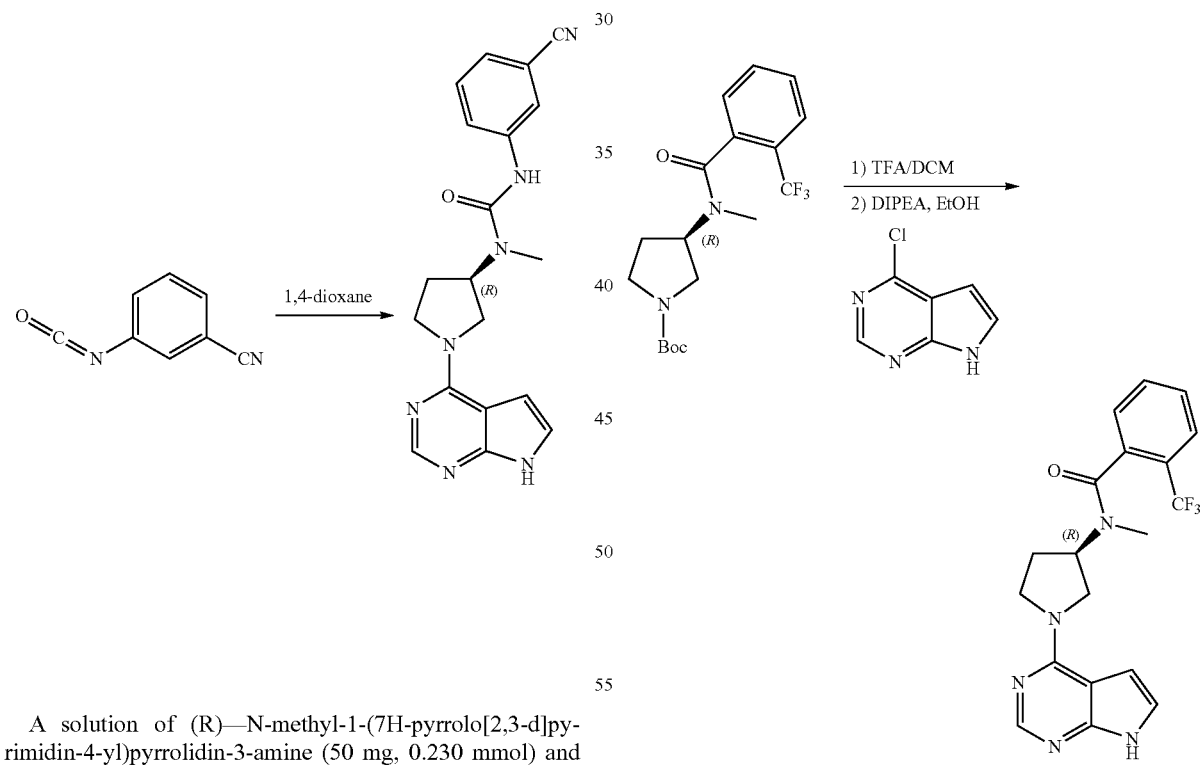

A solution of (R)—N-methyl-1-(7H-pyrrolo[2,3-d]pyrimidin-4-yl)pyrrolidin-3-amine (50 mg, 0.230 mmol) and 3-isocyanatobenzonitrile (37 mg, 0.257 mmol) in 1,4-dioxane (1 mL) was refluxed overnight. The volatiles were removed under vacuum and the residue was purified by flash chromatography to give the title compound. MS (m/z): 362 (M+H)+.

The following compound was prepared according to the procedures of Compound 16 using the corresponding intermediates and reagents under appropriate conditions that could be recognized by one skilled in the art.

A solution of (R)-tert-butyl 3-(N-methyl-2-(trifluoromethyl)benzamido)pyrrolidine-1-carboxylate (1 mmol) in TFA (2 mL) and DCM (2 mL) was stirred at room temperature for 2 hours, concentrated and diluted with water. It was then basified with aqueous NaHCO3 solution till pH=~9, and extracted with EtOAc. The combined extracts were dried, filtered, and concentrated to give (R)—N-methyl-N-(pyrrolidin-3-yl)-2-(trifluoromethyl)benzamide.

To a solution of (R)—N-methyl-N-(pyrrolidin-3-yl)-2-(trifluoromethyl)benzamide (1 mmol) and 4-chloro-7H-pyrrolo[2,3-d]pyrimidine (0.8 mmol) in the EtOH (3 mL) was added DIPEA (2 mmol) with stirring at room temperature. The reaction mixture was refluxed overnight. The mixture was then concentrated, and purified by flash chromatography to give the title compound. MS (m/z): 390 (M+H)$^+$.

The following compounds were prepared according to the procedures of Compound 18 using the corresponding intermediates and reagents under appropriate condition that could be recognized by one skilled in the art.

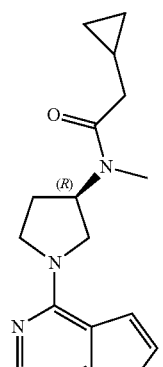

| Compound | Structure | MS (m/z) (M + H)$^+$ |
|---|---|---|
| 19 | 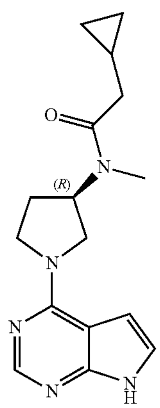 | 300 |
| 20 | 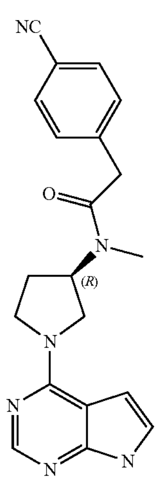 | 361 |
| 21 | | 418 |
| 22 | | 393 |

Compound 23

(R)—N-(1-(7H-pyrrolo[2,3-d]pyrimidin-4-yl)pyrrolidin-3-yl)-2-(1H-imidazol-4-yl)-N-methylacetamide

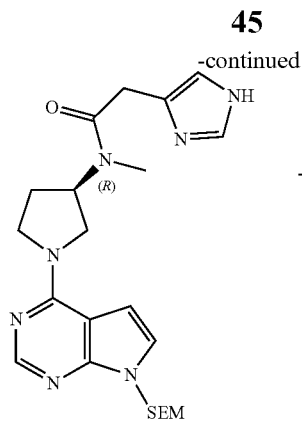

1) TFA/DCM
2) NH₂CH₂CH₂NH₂
MeOH

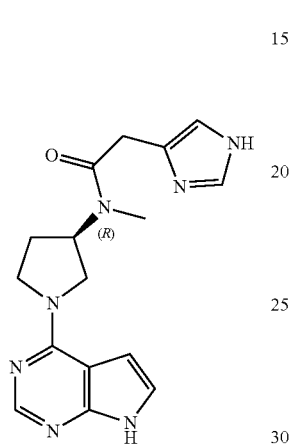

(A) (R)-2-(1H-imidazol-4-yl)-N-methyl-N-(1-(7-((2-(trimethylsilyl)ethoxy)methyl)-7H-pyrrolo[2,3-d]pyrimidin-4-yl)pyrrolidin-3-yl)acetamide To a solution of (R)—N-methyl-1-(7-((2-(trimethylsilyl)ethoxy)methyl)-7H-pyrrolo[2,3-d]pyrimidin-4-yl)pyrrolidin-3-amine (0.29 mmol), TBTU (0.35 mmol) and DIPEA (0.58 mmol) in THF was slowly added 2-(1H-imidazol-4-yl)acetic acid (0.29 mmol). The mixture was stirred at room temperature overnight, then concentrated, diluted with water, and extracted with EtOAc. The combined extracts were dried, filtered and concentrated. The residue was purified by flash chromatography to give the title compound.

(B) (R)—N-(1-(7H-pyrrolo[2,3-d]pyrimidin-4-yl)pyrrolidin-3-yl)-2-(1H-imidazol-4-yl)-N-methylacetamide A solution of (R)-2-(1H-imidazol-4-yl)-N-methyl-N-(1-(7-((2-(trimethylsilyl)ethoxy)methyl)-7H-pyrrolo[2,3-d]pyrimidin-4-yl)pyrrolidin-3-yl)acetamide (0.11 mmol) in TFA (1 mL) and DCM (2 mL) was stirred at room temperature for 1.5 hours. The volatiles were removed under reduce pressure. The residue was dissolved in MeOH (2 mL) and treated with ethane-1,2-diamine (0.2 mL) at room temperature overnight. The volatiles were then removed under reduced pressure and the residue was purified by flash chromatography to give the title compound. MS (m/z): 326 (M+H)⁺.

The following compounds were prepared according to the procedures of Compound 23 using the corresponding intermediates and reagents under appropriate conditions that could be recognized by one skilled in the art.

| Compound | Structure | MS (m/z) (M + H)⁺ |
|---|---|---|
| 24 | 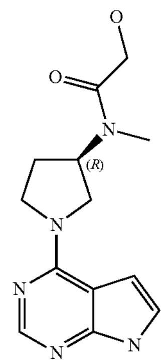 | 276 |
| 25 | 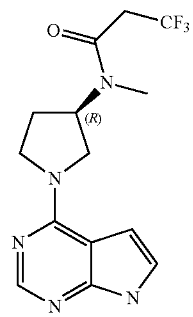 | 328 |
| 26 | 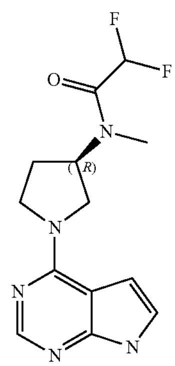 | 296 |
| 27 | 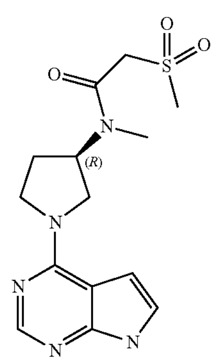 | 338 |

-continued

| Compound | Structure | MS (m/z) (M + H)+ |
|---|---|---|
| 28 | 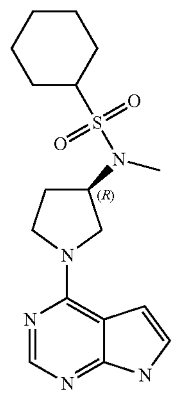 | 364 |

Compound 29

1-((R)-1-(7H-pyrrolo[2,3-d]pyrimidin-4-yl)pyrrolidin-3-yl)-3-((1R,2R)-2-hydroxy-2,3-dihydro-1H-inden-1-yl)-1-methylurea

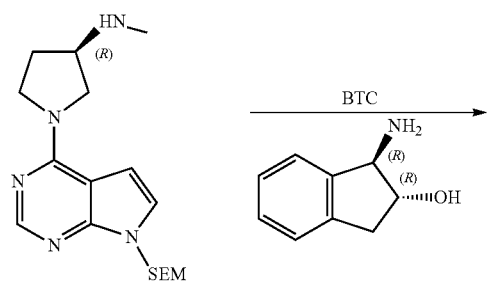

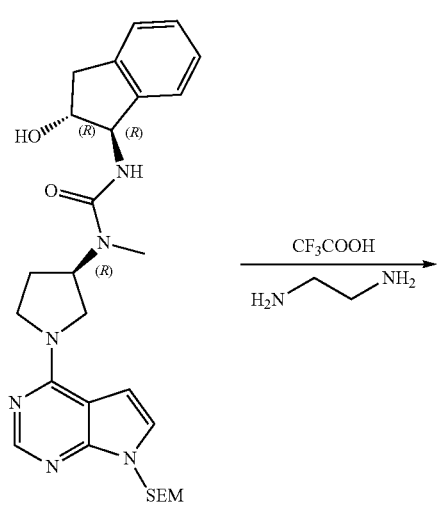

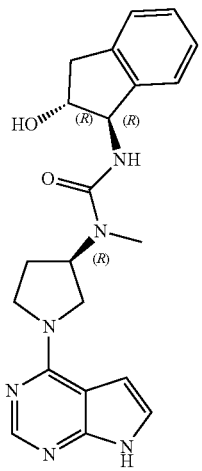

(A) 3-((1R,2R)-2-hydroxy-2,3-dihydro-1H-inden-1-yl)-1-methyl-1-((R)-1-(7-((2-(trimethylsilyl)ethoxy)methyl)-7H-pyrrolo[2,3-d]pyrimidin-4-yl)pyrrolidin-3-yl)urea To a solution of (R)—N-methyl-1-(7-((2-(trimethylsilyl)ethoxy)methyl)-7H-pyrrolo[2,3-d]pyrimidin-4-yl)pyrrolidin-3-amine (0.29 mmol) in anhydrous THF (2 mL) were subsequently added BTC and DIPEA (0.35 mmol) at 0° C. The mixture was stirred at 0° C. for 30 minutes and at the ambient temperature for 3 hours. It was then cooled to 0° C., (1R,2R)-1-amino-2,3-dihydro-1H-inden-2-ol (0.35 mmol) was added, and the mixture was stirred at room temperature for 24 hours. It was then purified with preparative TLC to give the title compound.

(B) 1-((R)-1-(7H-pyrrolo[2,3-d]pyrimidin-4-yl)pyrrolidin-3-yl)-3-((1R,2R)-2-hydroxy-2,3-dihydro-1H-inden-1-yl)-1-methylurea The tile compound was prepared according to the procedure of Compound 23 (B) using 3-((1R,2R)-2-hydroxy-2,3-dihydro-1H-inden-1-yl)-1-methyl-1-((R)-1-(7-((2-(trimethylsilyl)ethoxy)methyl)-7H-pyrrolo[2,3-d]pyrimidin-4-yl)pyrrolidin-3-yl)urea. MS (m/z): 393 (M+H)+.

The following compounds were prepared according to the procedures of Compound 29 using the corresponding intermediates and reagents under appropriate conditions that could be recognized by one skilled in the art.

| Compound | Structure | MS (m/z) (M + H)+ |
|---|---|---|
| 30 | 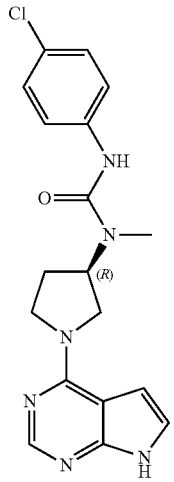 | 405 |
| 31 | 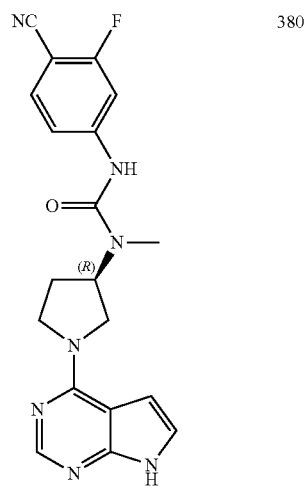 | 380 |
| 32 | 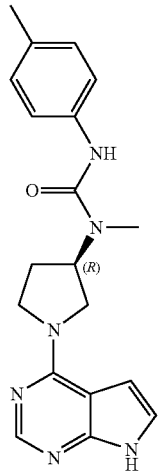 | 351 |
-continued
| Compound | Structure | MS (m/z) (M + H)+ |
|---|---|---|
| 33 | 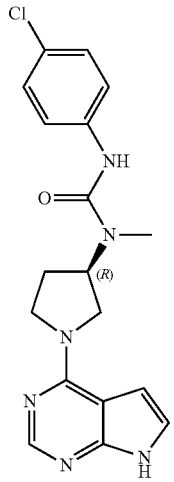 | 371 |
| 34 | 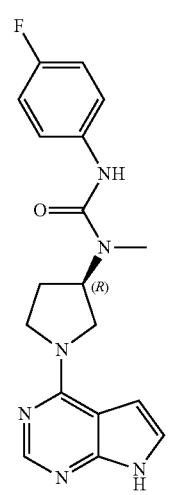 | 355 |
| 35 | 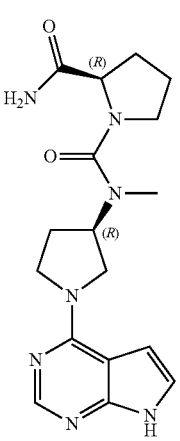 | 358 |

-continued

| Compound | Structure | MS (m/z) (M + H)+ |
|---|---|---|
| 36 | (tetrahydropyran-NH-C(O)-N(Me)-pyrrolidine(R)-N-pyrrolo[2,3-d]pyrimidine) | 345 |
| 37 | (pyrrolidine-C(O)-N(Me)-pyrrolidine(R)-N-pyrrolo[2,3-d]pyrimidine) | 315 |
| 38 | (NC-(R)-pyrrolidine-C(O)-N(Me)-pyrrolidine(R)-N-pyrrolo[2,3-d]pyrimidine) | 340 |

Compound 39

(R)—N-cyclopentyl-N-(prop-2-ynyl)-1-(7H-pyrrolo[2,3-d]pyrimidin-4-yl)pyrrolidin-3-amine

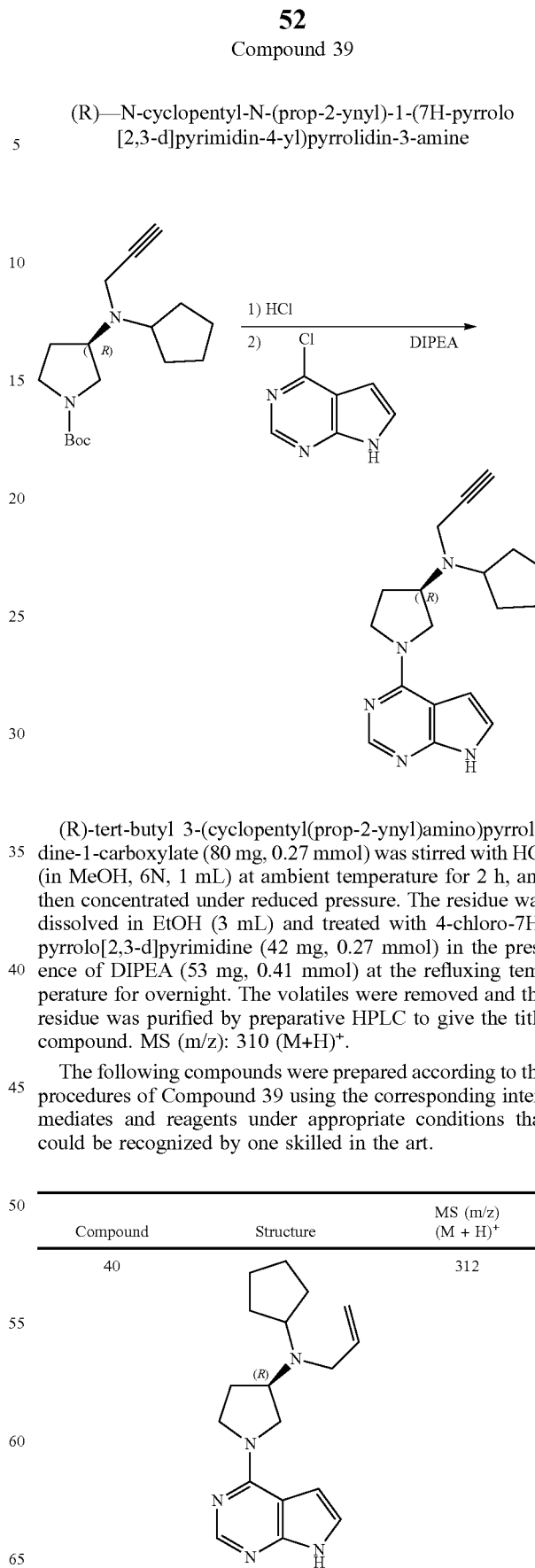

(R)-tert-butyl 3-(cyclopentyl(prop-2-ynyl)amino)pyrrolidine-1-carboxylate (80 mg, 0.27 mmol) was stirred with HCl (in MeOH, 6N, 1 mL) at ambient temperature for 2 h, and then concentrated under reduced pressure. The residue was dissolved in EtOH (3 mL) and treated with 4-chloro-7H-pyrrolo[2,3-d]pyrimidine (42 mg, 0.27 mmol) in the presence of DIPEA (53 mg, 0.41 mmol) at the refluxing temperature for overnight. The volatiles were removed and the residue was purified by preparative HPLC to give the title compound. MS (m/z): 310 (M+H)+.

The following compounds were prepared according to the procedures of Compound 39 using the corresponding intermediates and reagents under appropriate conditions that could be recognized by one skilled in the art.

| Compound | Structure | MS (m/z) (M + H)+ |
|---|---|---|
| 40 | (cyclopentyl-N(allyl)-pyrrolidine(R)-N-pyrrolo[2,3-d]pyrimidine) | 312 |

-continued
| Compound | Structure | MS (m/z) (M + H)+ |
|---|---|---|
| 41 | 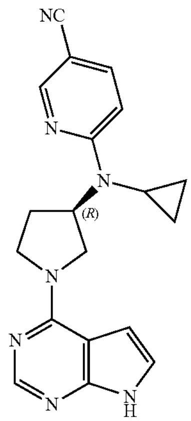 | 346 |
| 42 | 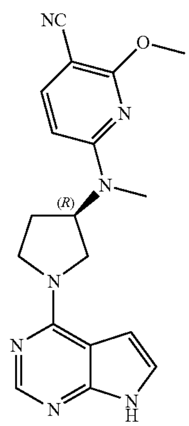 | 350 |
| 43 | 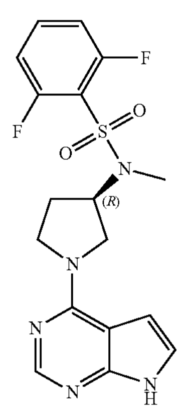 | 394 |
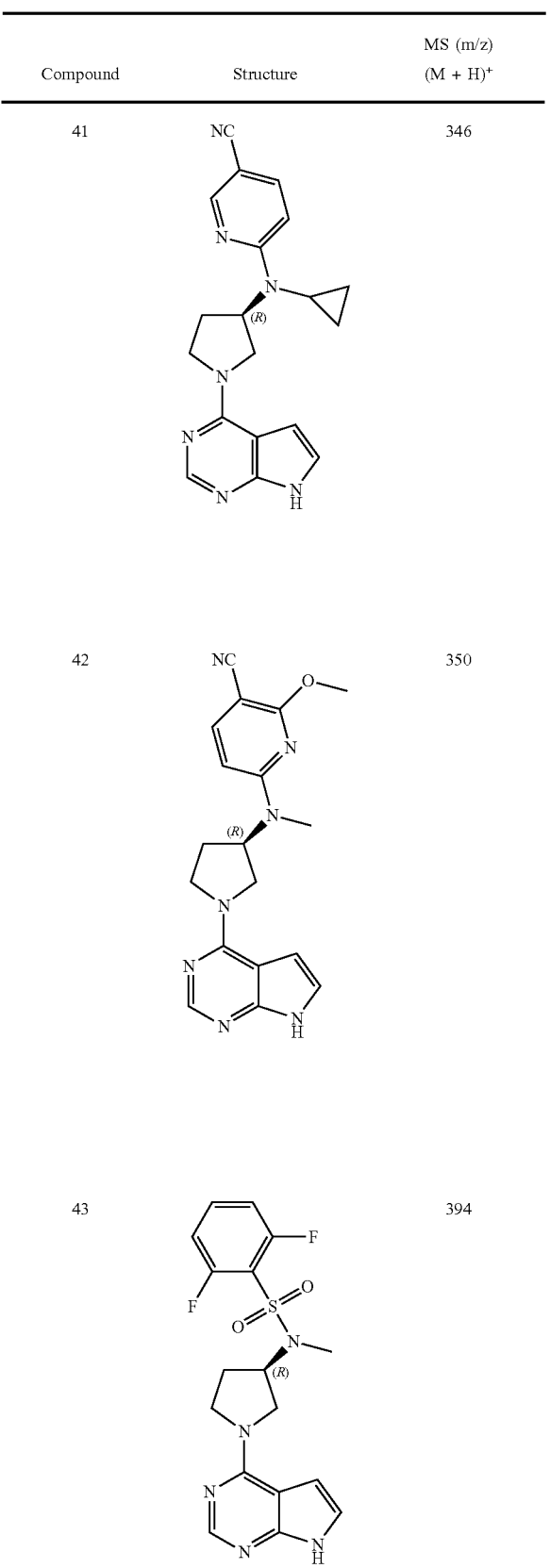
-continued
| Compound | Structure | MS (m/z) (M + H)+ |
|---|---|---|
| 44 | 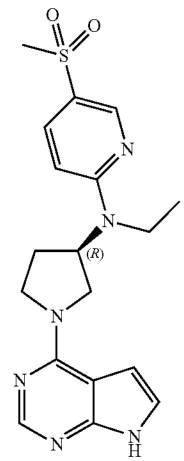 | 387 |
| 45 | 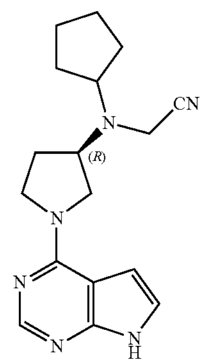 | 311 |
| 46 | 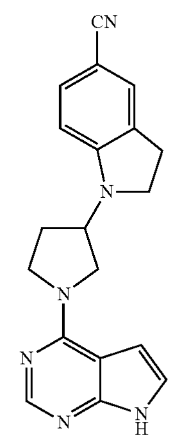 [SMILES: N#Cc1ccc2c(c1)CCN2C1CCN(c2ncnc3[nH]ccc23)C1] | 331 |
| 47 | 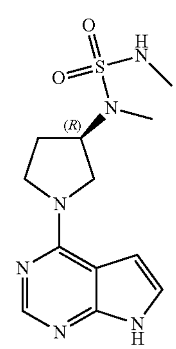 | 311 |
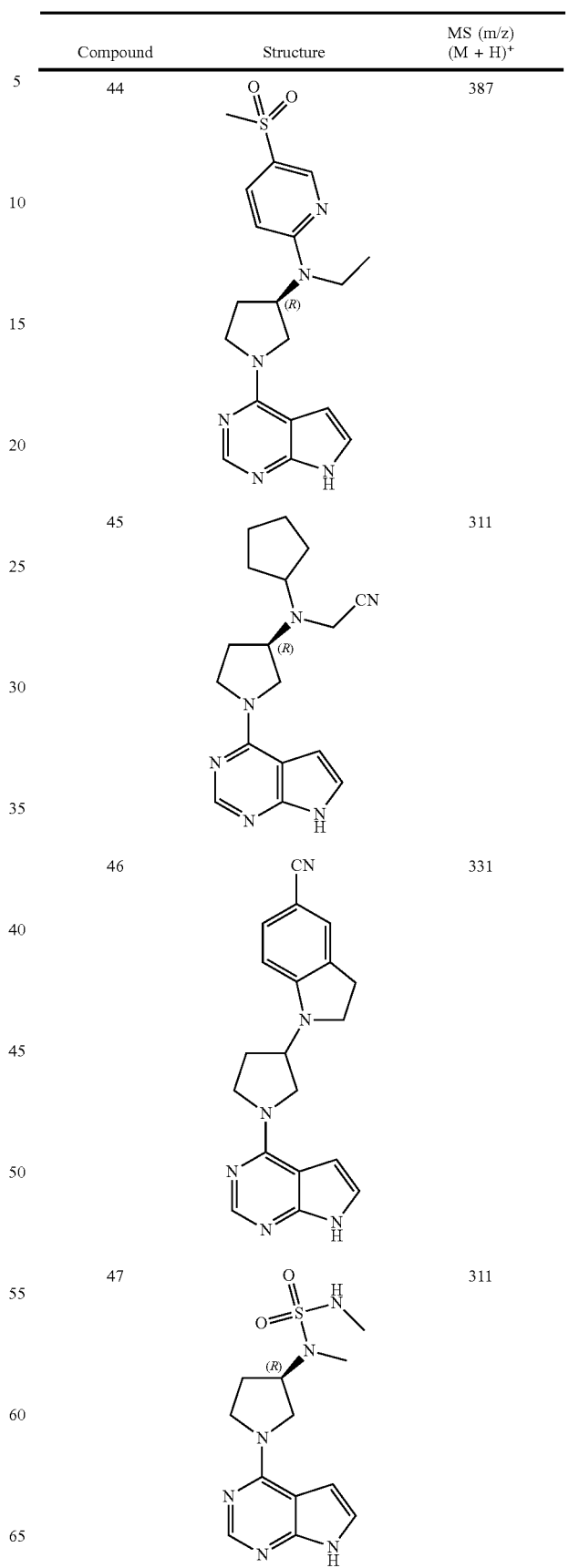

-continued
| Compound | Structure | MS (m/z) (M + H)+ |
|---|---|---|
| 48 | 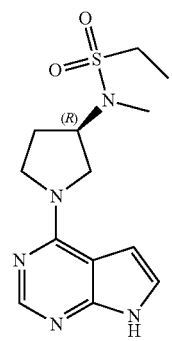 | 310 |
| 49 | 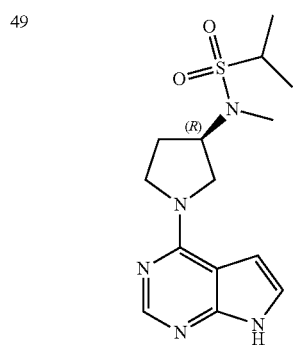 | 324 |
| 50 | 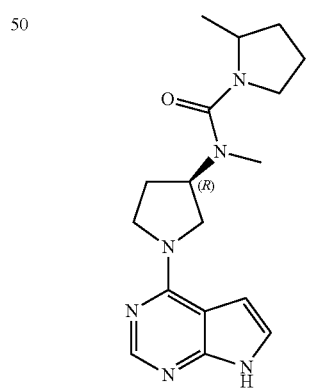 | 329 |
| 51 | 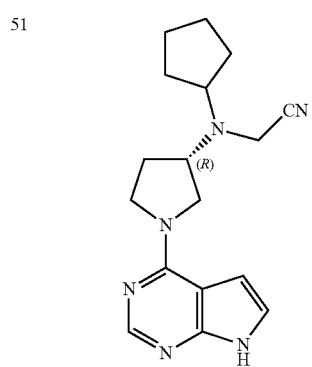 | 311 |
-continued
| Compound | Structure | MS (m/z) (M + H)+ |
|---|---|---|
| 52 | 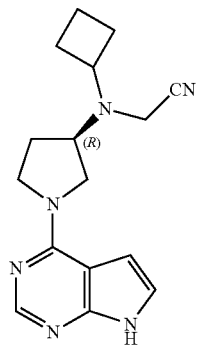 | 297 |
| 53 | 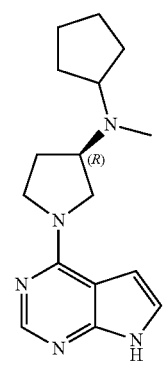 | 286 |
| 54 | 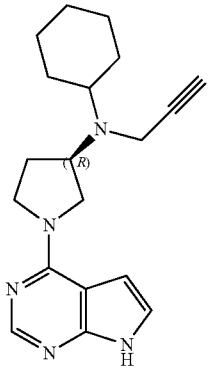 | 324 |
| 55 | 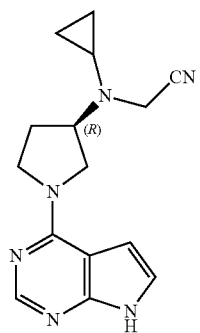 | 283 |

57
-continued
| Compound | Structure | MS (m/z) (M + H)+ |
|---|---|---|
| 56 | 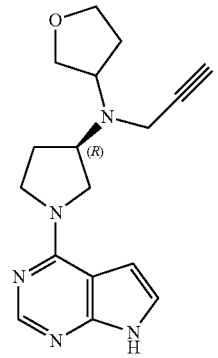 | 312 |
| 57 | 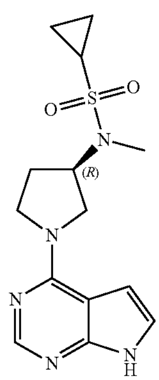 | 322 |
| 58 | 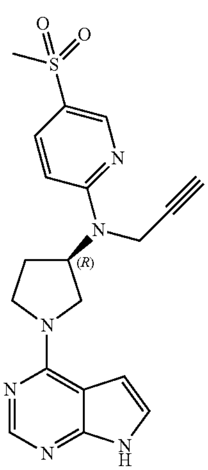 | 397 |
58
-continued
| Compound | Structure | MS (m/z) (M + H)+ |
|---|---|---|
| 59 | 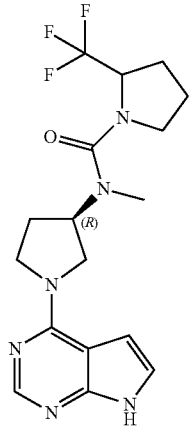 | 383 |
| 60 | 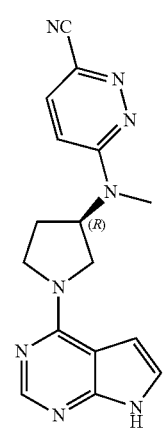 | 321 |
| 61 | 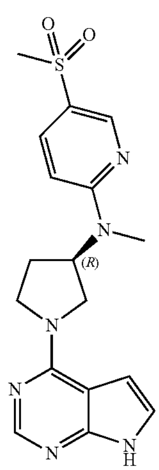 | 373 |

| Compound | Structure | MS (m/z) (M + H)+ |
|---|---|---|
| 62 | | 364 |

Compound 63

(R)—N-(1-(7H-pyrrolo[2,3-d]pyrimidin-4-yl)pyrrolidin-3-yl)-2-chloro-N-methylpyrimidin-4-amine

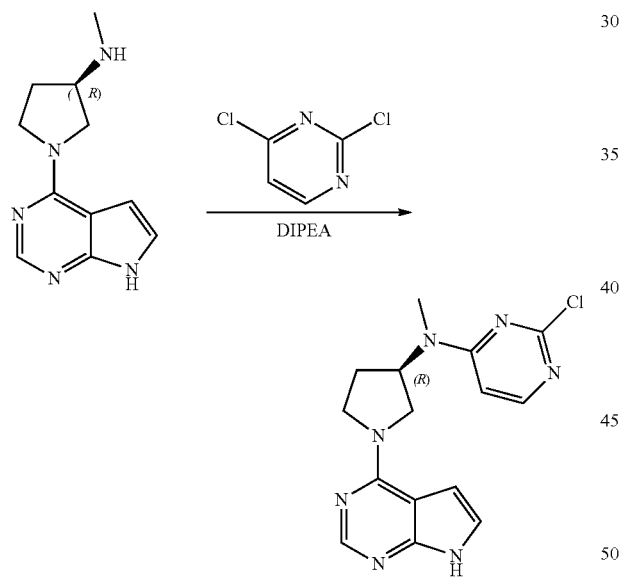

A mixture of methyl (R)—N-methyl-1-(7H-pyrrolo[2,3-d]pyrimidin-4-yl)pyrrolidin-3-amine (0.20 g, 0.92 mmol), 2,4-dichloropyrimidine (0.18 g, 1.21 mmol) and DIPEA (0.25 g, 1.94 mmol) in DMF (6 mL) was stirred at 110° C. for 16 hours. The mixture was poured into water (5 mL) and extracted with ethyl acetate (2×8 mL). The combined extracts was washed with brine (2×30 mL), dried over anhydrous $Na_2SO_4$, and concentrated under reduced pressure. The residue was purified by chromatography on silica gel (v. DCM/MeOH=12/1) to give the title compound. MS (m/z): 330 (M+H)+.

The following compounds were prepared according to the procedures of Compound 65 using the corresponding intermediates and reagents under appropriate conditions that could be recognized by one skilled in the art.

| Compound | Structure | MS (m/z) (M + H)+ |
|---|---|---|
| 64 | 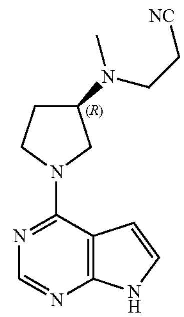 | 271 |
| 65 | 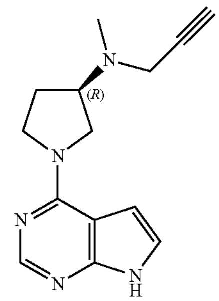 | 256 |
| 66 | 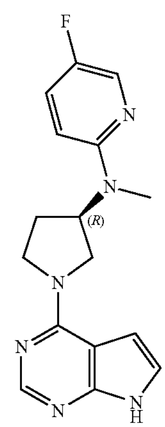 | 313 |
| 67 | 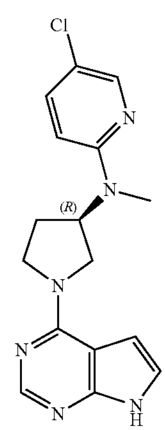 | 329 ($^{35}$Cl) 331 ($^{37}$Cl) |

-continued

| Compound | Structure | MS (m/z) (M + H)+ |
|---|---|---|
| 68 | 5-Br-pyridin-2-yl, N-methyl, (R)-pyrrolidin-3-yl, 7H-pyrrolo[2,3-d]pyrimidin-4-yl | 373 ($^{79}$Br) 375 ($^{81}$Br) |
| 69 | 5-I-pyridin-2-yl, N-methyl, (R)-pyrrolidin-3-yl, 7H-pyrrolo[2,3-d]pyrimidin-4-yl | 421 |
| 70 | 5-NO$_2$-pyridin-2-yl, N-methyl, (R)-pyrrolidin-3-yl, 7H-pyrrolo[2,3-d]pyrimidin-4-yl | 340 |

-continued

| Compound | Structure | MS (m/z) (M + H)+ |
|---|---|---|
| 71 | 5-CN-pyridin-2-yl, N-methyl, (R)-pyrrolidin-3-yl, 7H-pyrrolo[2,3-d]pyrimidin-4-yl | 320 |
| 72 | 6-Cl-5-CN-4-methyl-pyridin-2-yl, N-methyl, (R)-pyrrolidin-3-yl, 7H-pyrrolo[2,3-d]pyrimidin-4-yl | 368 ($^{35}$Cl) 370 ($^{37}$Cl) |
| 73 | 6-Cl-4-methyl-3-CN-pyridin-2-yl, N-methyl, (R)-pyrrolidin-3-yl, 7H-pyrrolo[2,3-d]pyrimidin-4-yl | 368 ($^{35}$Cl) 370 ($^{37}$Cl) |

-continued
| Compound | Structure | MS (m/z) (M + H)+ |
|---|---|---|
| 74 | 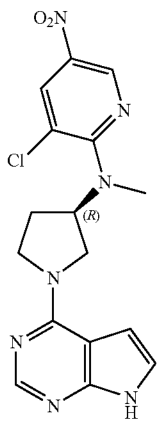 | 374 ($^{35}Cl$) 376 ($^{37}Cl$) |
| 75 | 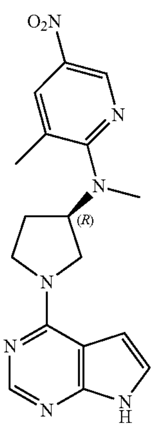 | 354 |
| 76 | 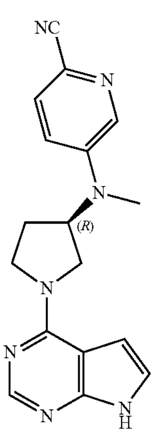 | 320 |
-continued
| Compound | Structure | MS (m/z) (M + H)+ |
|---|---|---|
| 77 | 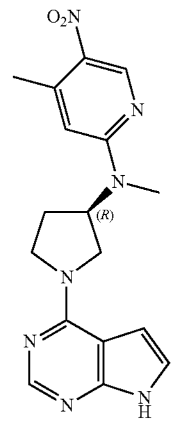 | 354 |
| 78 | 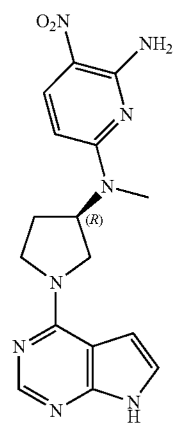 | 355 |
| 79 | 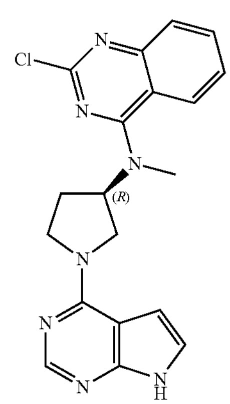 | 380 ($^{35}Cl$) 382 ($^{37}Cl$) |
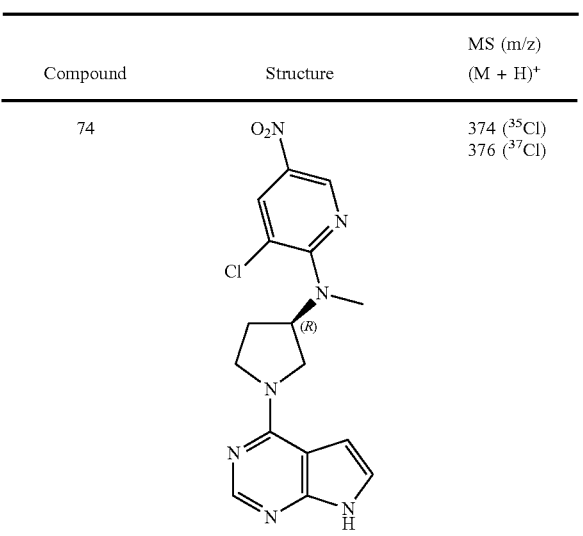
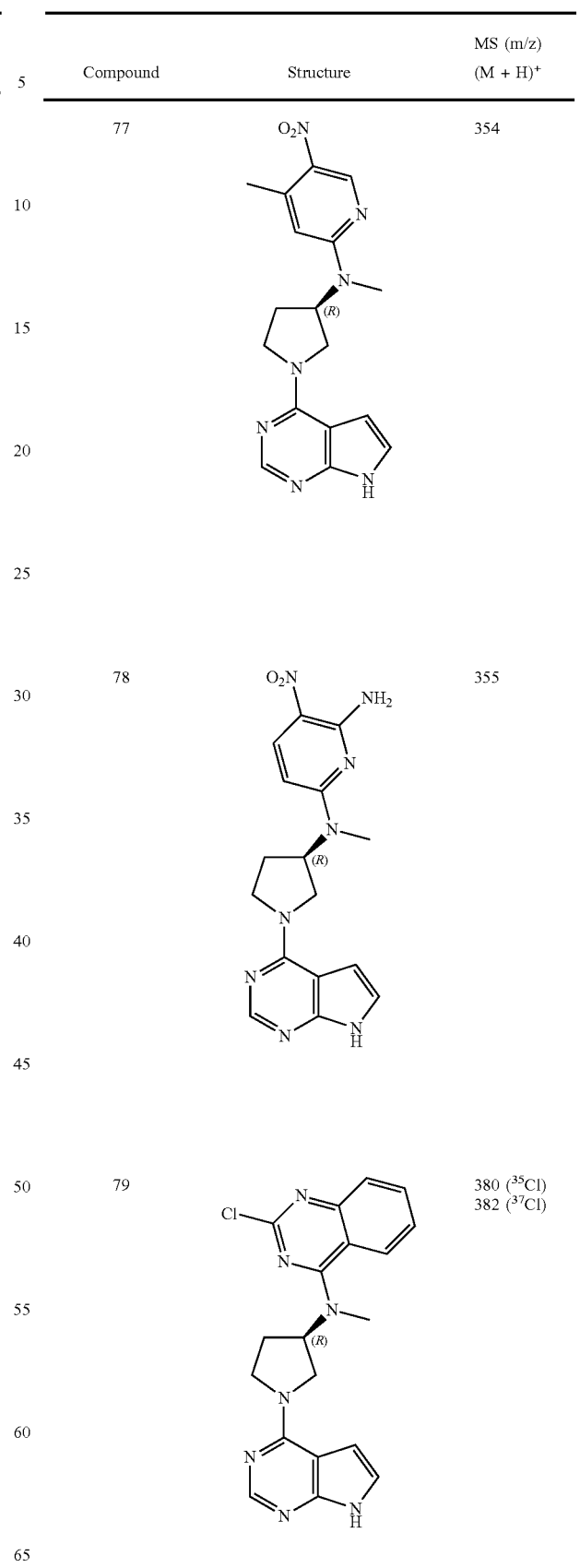

-continued
| Compound | Structure | MS (m/z) (M + H)+ |
|---|---|---|
| 80 | 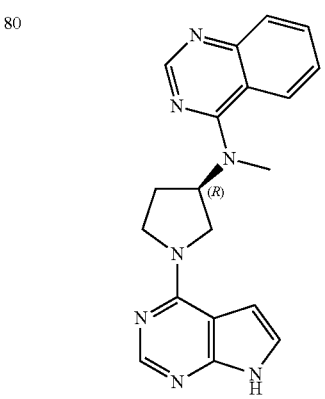 | 346 |
| 81 | 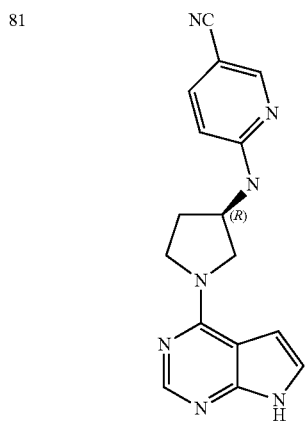 | 306 |
| 82 | 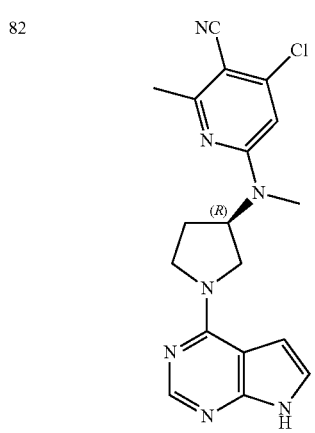 | 368 ($^{35}$Cl) 370 ($^{37}$Cl) |
-continued
| Compound | Structure | MS (m/z) (M + H)+ |
|---|---|---|
| 83 | 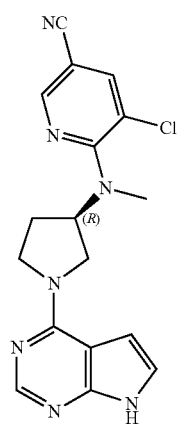 | 354 ($^{35}$Cl) 356 ($^{37}$Cl) |
| 84 | 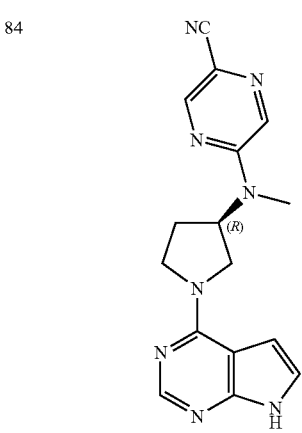 | 321 |
| 85 | 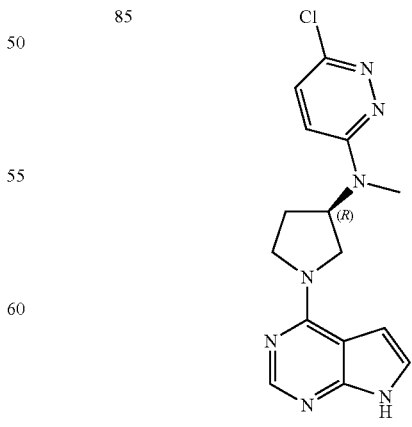 | 330 ($^{35}$Cl) 332 ($^{37}$Cl) |

-continued
| Compound | Structure | MS (m/z) (M + H)+ |
|---|---|---|
| 86 | 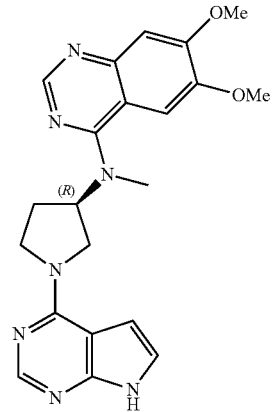 | 406 |
| 87 | 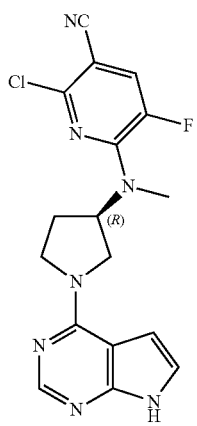 | 372 ($^{35}$Cl) 374 ($^{37}$Cl) |
| 88 | 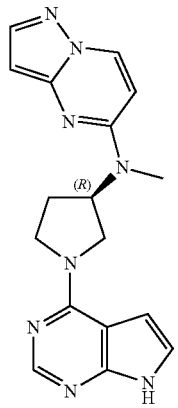 | 335 |
-continued
| Compound | Structure | MS (m/z) (M + H)+ |
|---|---|---|
| 89 | 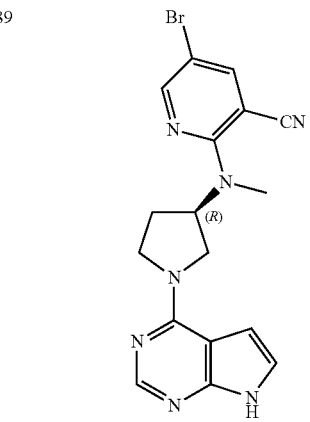 | 398 ($^{79}$Br) 400 ($^{81}$Br) |
| 90 | 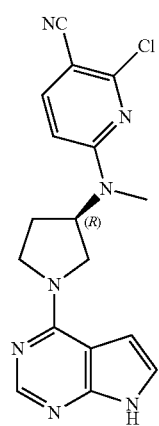 | 354 ($^{35}$Cl) 356 ($^{37}$Cl) |
| 91 | 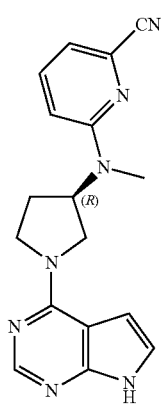 | 320 |

-continued
| Compound | Structure | MS (m/z) (M + H)+ |
|---|---|---|
| 92 | 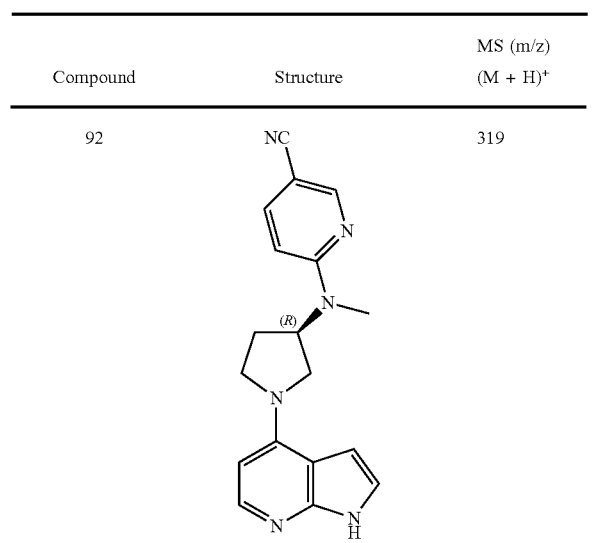 | 319 |
| 93 | 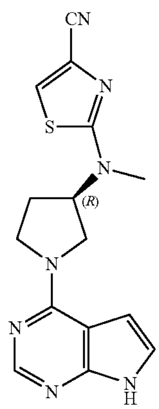 | 326 |
| 94 | 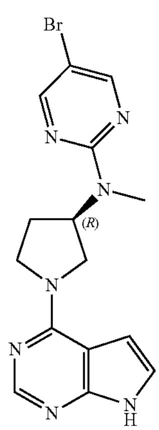 | 374 (79Br) 376 (81Br) |
-continued
| Compound | Structure | MS (m/z) (M + H)+ |
|---|---|---|
| 95 | 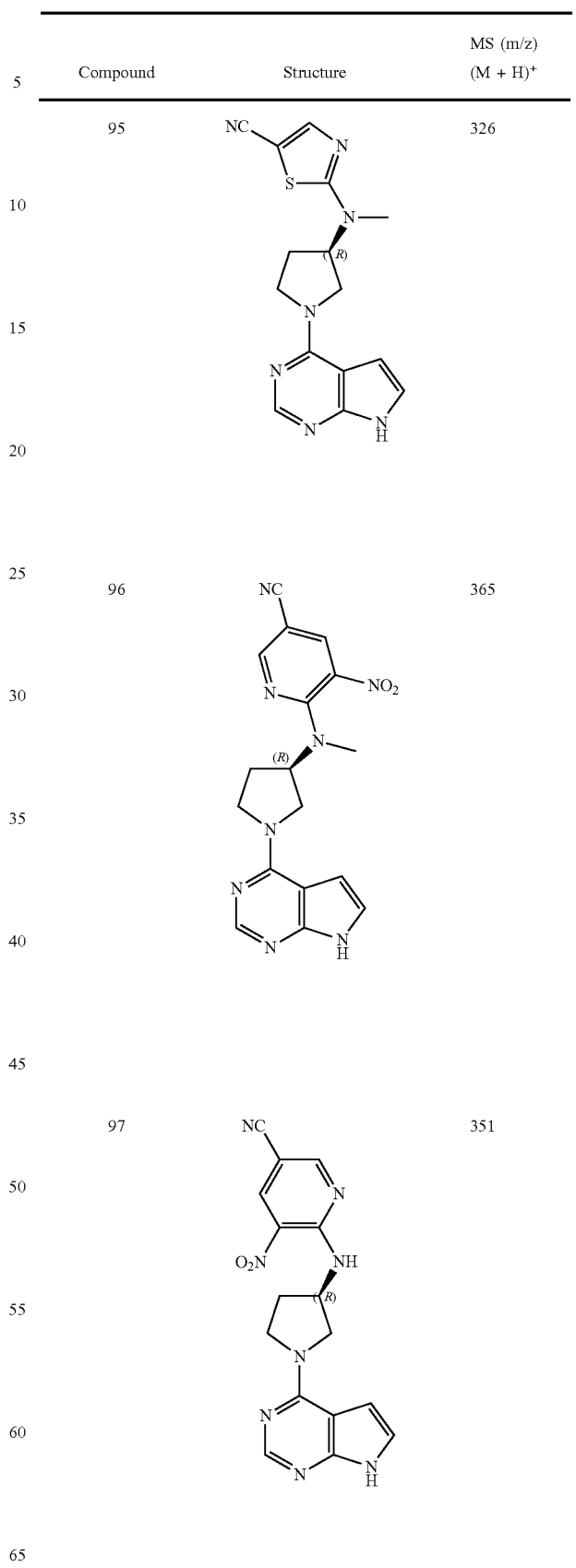 | 326 |
| 96 | 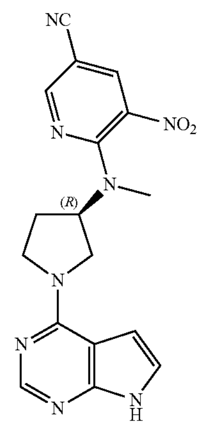 | 365 |
| 97 | 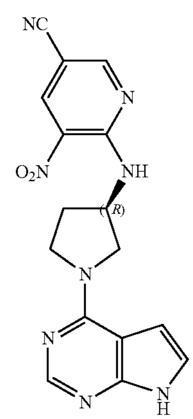 | 351 |

-continued
| Compound | Structure | MS (m/z) (M + H)⁺ |
|---|---|---|
| 98 | 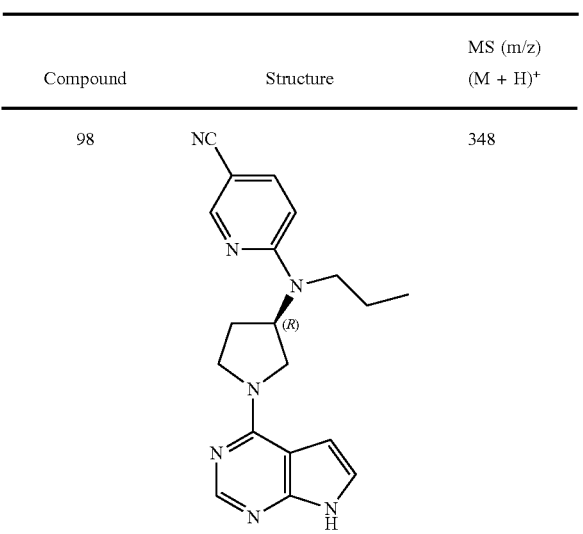 | 348 |
| 99 | 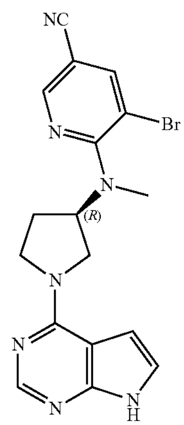 | 398 (⁷⁹Br) 400 (⁸¹Br) |
| 100 | 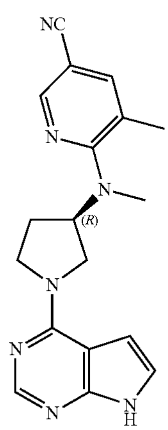 | 334 |
-continued
| Compound | Structure | MS (m/z) (M + H)⁺ |
|---|---|---|
| 101 | 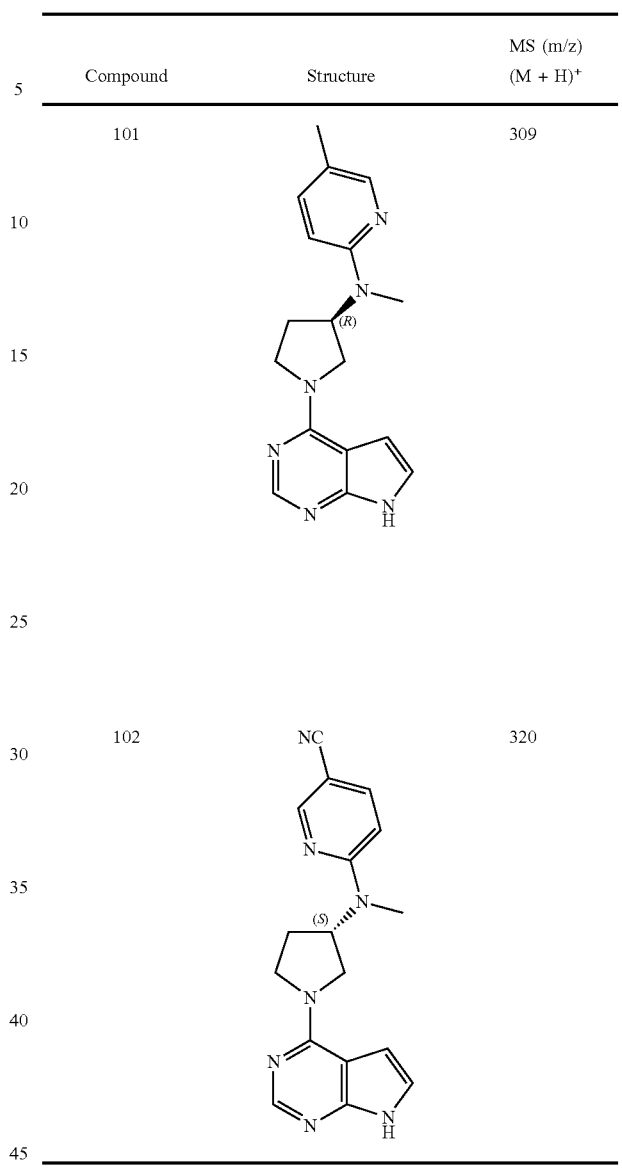 | 309 |
| 102 | 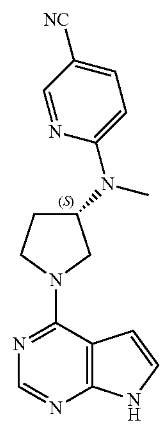 | 320 |
Compound 103
(R)-4-((1-(7H-pyrrolo[2,3-d]pyrimidin-4-yl)pyrrolidin-3-yl)(methyl)amino)-3-fluorobenzonitrile
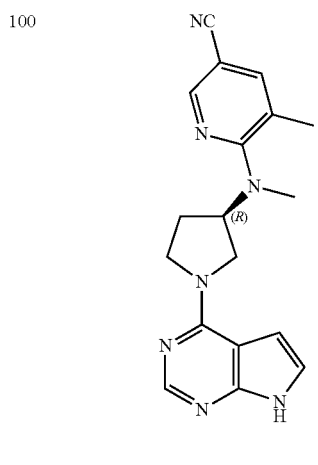 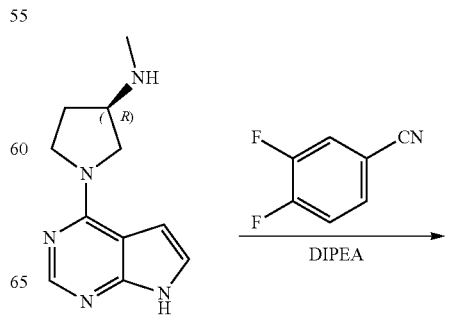
DIPEA -continued

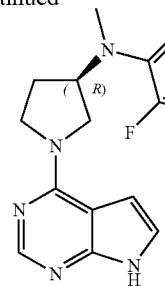

A mixture of methyl (R)—N-methyl-1-(7H-pyrrolo[2,3-d]pyrimidin-4-yl)pyrrolidin-3-amine (0.50 g, 2.3 mmol), 3,4-difluorobenzonitrile (0.48 g, 3.45 mmol) and DIPEA (0.59 g, 4.6 mmol) in DMSO (10 mL) was stirred at 90° C. for overnight. The mixture was poured into water (50 mL) and extracted with ethyl acetate (2×50 mL). The combined extracts was washed with brine (2×50 mL), dried over anhydrous $Na_2SO_4$, filtered, and concentrated under reduced pressure. The residue was purified by chromatography to give the title compound (0.404 g, 52% yield). MS (m/z): 337 $(M+H)^+$.

The following compounds were prepared according to the procedures of Compound 103 using the corresponding intermediates and reagents under appropriate conditions that could be recognized by one skilled in the art.

| Compound | Structure | MS (m/z) (M + H)+ |
|---|---|---|
| 104 | | 319 |
| 105 | | 337 |
| 106 | 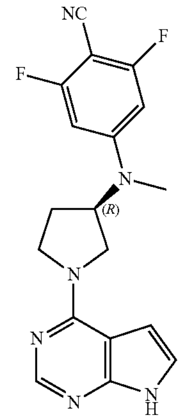 | 355 |
| 107 | 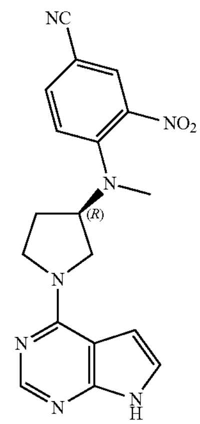 | 364 |
| 108 | 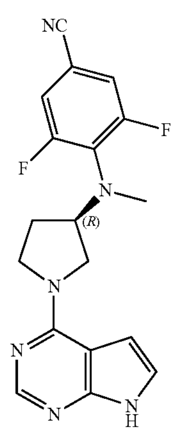 | 355 |

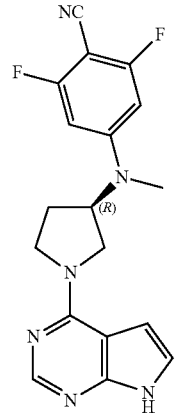

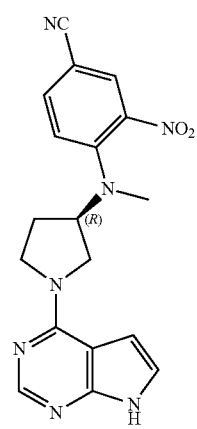

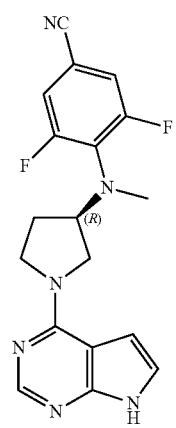

75
-continued
| Compound | Structure | MS (m/z) (M + H)+ |
|---|---|---|
| 109 | 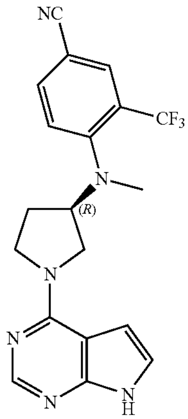 | 387 |
| 110 | 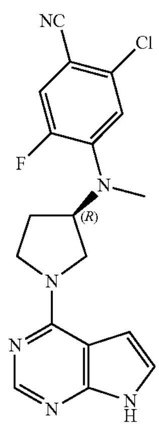 | 371 ($^{35}$Cl) 373 ($^{37}$Cl) |
| 111 | 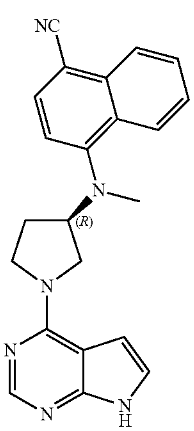 | 369 |
76
-continued
| Compound | Structure | MS (m/z) (M + H)+ |
|---|---|---|
| 112 | 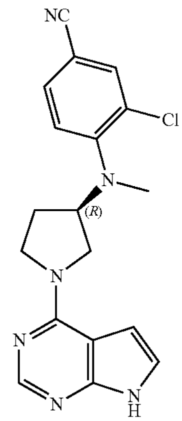 | 353 ($^{35}$Cl) 355 ($^{37}$Cl) |
| 113 | 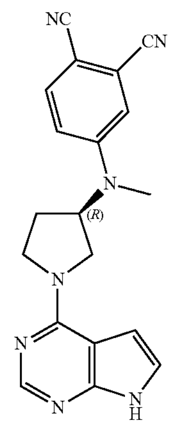 | 344 |
| 114 | 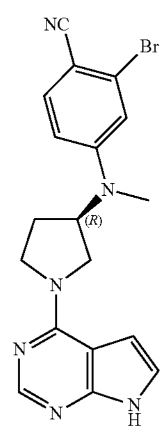 | 397 ($^{79}$Br) 399 ($^{81}$Br) |
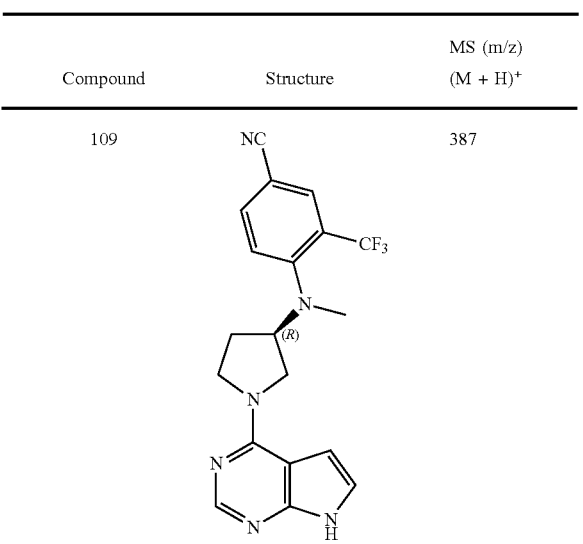
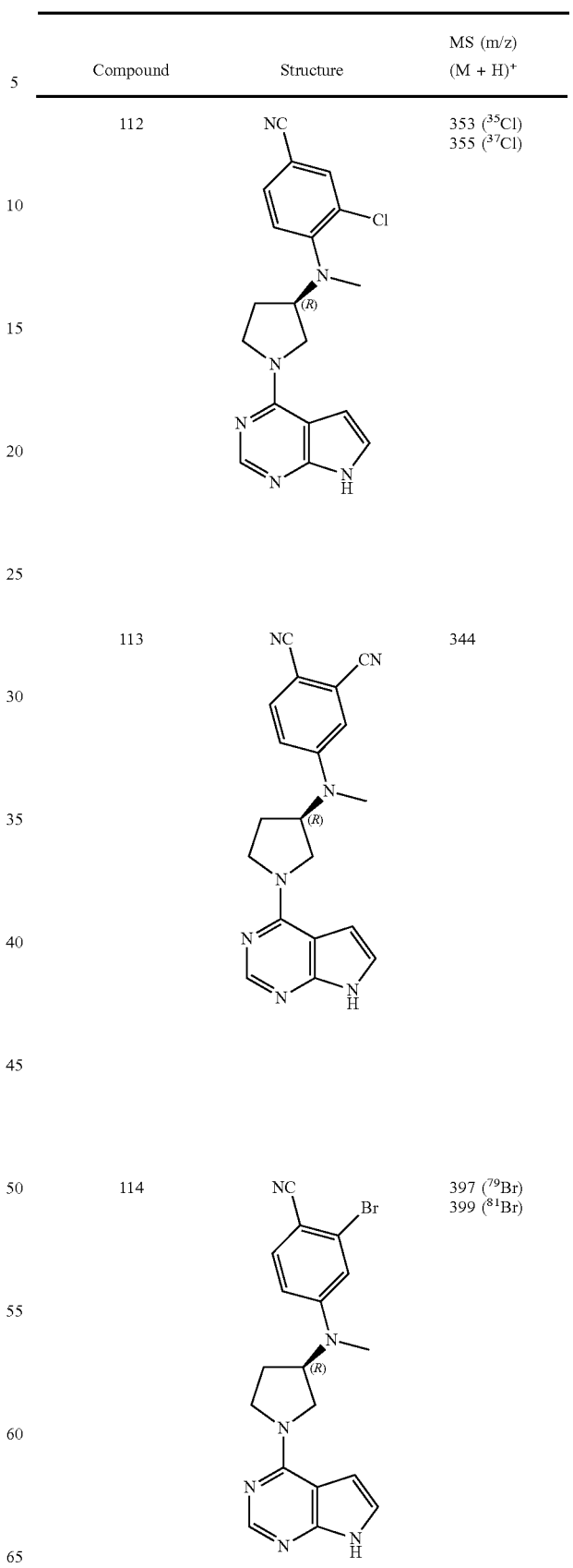

-continued

| Compound | Structure | MS (m/z) (M + H)+ |
|---|---|---|
| 115 | 4-cyano-2-bromo-phenyl-N-methyl-(R)-pyrrolidin-3-yl-(7H-pyrrolo[2,3-d]pyrimidin-4-yl) | 397 (79Br) 399 (81Br) |
| 116 | 4-cyano-3-chloro-phenyl-N-methyl-(R)-pyrrolidin-3-yl-(7H-pyrrolo[2,3-d]pyrimidin-4-yl) | 353 (35Cl) 355 (37Cl) |
| 117 | 4-cyano-2,3,5,6-tetrafluorophenyl-N-methyl-(R)-pyrrolidin-3-yl-(7H-pyrrolo[2,3-d]pyrimidin-4-yl) | 391 |

-continued

| Compound | Structure | MS (m/z) (M + H)+ |
|---|---|---|
| 118 | 2,4-difluoro-6-cyanophenyl-N-methyl-(R)-pyrrolidin-3-yl-(7H-pyrrolo[2,3-d]pyrimidin-4-yl) | 355 |

Compound 119

(R)-3-((1-(7H-pyrrolo[2,3-d]pyrimidin-4-yl)pyrrolidin-3-yl)(methyl)amino)benzonitrile (A) (R)-3-(methyl(1-(7-((2-(trimethylsilyl)ethoxy)methyl)-7H-pyrrolo[2,3-d]pyrimidin-4-yl)pyrrolidin-3-yl)amino)benzonitrile Under N₂, a mixture of (R)—N-methyl-1-(7-((2-(trimethylsilyl)ethoxy)methyl)-7H-pyrrolo[2,3-d]pyrimidin-4-yl)pyrrolidin-3-amine (50 mg, 0.14 mmol), 3-bromobenzonitrile (39 mg, 0.21 mmol), Pd$_2$(dba)$_3$ (1 mg, 0.002 mmol), BINAP (5 mg, 0.008 mmol) and t-BuONa (27 mg, 0.28 mmol) in toluene (2 mL) was stirred at reflux for 6 hour, cooled to ambient temperature, diluted with EtOAc (50 mL), washed with brine (3×10 mL), dried over anhydrous Na$_2$SO$_4$, filtered, and concentrated under reduced pressure. The residue was purified by preparative TLC (DCM: MeOH=20:1) to give the title compound. MS (m/z): 449 (M+H)$^+$.

(B) (R)-3-((1-(7H-pyrrolo[2,3-d]pyrimidin-4-yl)pyrrolidin-3-yl)(methyl)amino)-benzonitrile The title compound was prepared according to the procedures of Compound 23 (B) using (R)-3-(methyl(1-(7-((2-(trimethylsilyl)ethoxy)methyl)-7H-pyrrolo[2,3-d]pyrimidin-4-yl)pyrrolidin-3-yl)amino)benzonitrile. MS (m/z): 319 (M+H)$^+$.

Compound 120

(R)—N-methyl-N-(4-(methylsulfonyl)phenyl)-1-(7H-pyrrolo[2,3-d]pyrimidin-4-yl)pyrrolidin-3-amine

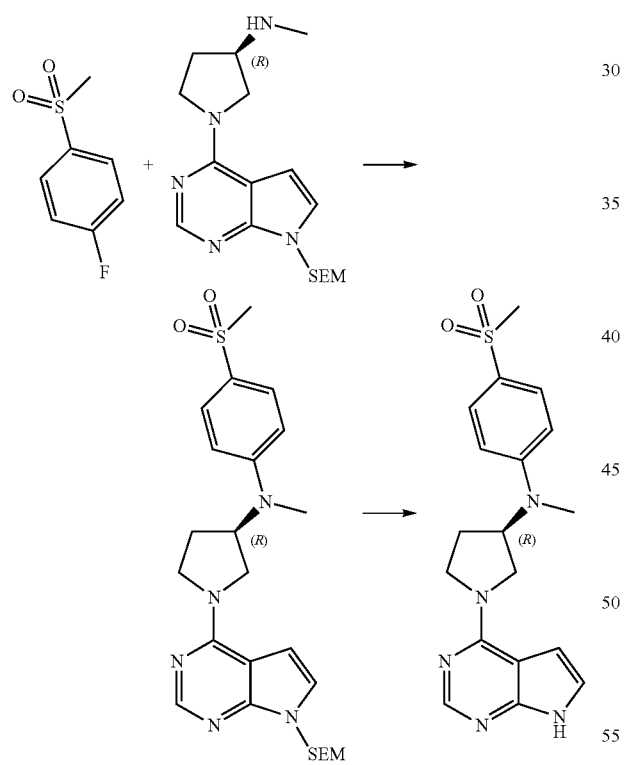

(A) (R)—N-methyl-N-(4-(methylsulfonyl)phenyl)-1-(7-((2-(trimethylsilyl)ethoxy)methyl)-7H-pyrrolo[2,3-d]pyrimidin-4-yl)pyrrolidin-3-amine A mixture of (R)—N-methyl-1-(7-((2-(trimethylsilyl)ethoxy)methyl)-7H-pyrrolo[2,3-d]pyrimidin-4-yl)pyrrolidin-3-amine (100 mg, 0.287 mmol) and 1-fluoro-4-(methylsulfonyl)benzene (150 mg, 0.861 mmol) and K$_2$CO$_3$ (158 mg, 1.142 mmol) in DMF (2 mL) was stirred at 120° C. overnight and then cooled to ambient temperature, poured into water, and extracted with EtOAc. The EtOAc layer was concentrated, purified by preparative TLC to give the title compound.

(B) (R)—N-methyl-N-(4-(methylsulfonyl)phenyl)-1-(7H-pyrrolo[2,3-d]pyrimidin-4-yl)pyrrolidin-3-amine The title compound was prepared according to the procedures of Compound 23 (B) using (R)—N-methyl-N-(4-(methylsulfonyl)phenyl)-1-(7-((2-(trimethylsilyl)ethoxy)methyl)-7H-pyrrolo[2,3-d]pyrimidin-4-yl)pyrrolidin-3-amine.MS (m/z): 372 (M+H)$^+$.

The following compounds were prepared according to the procedures of Compound 120 using the corresponding intermediates and reagents under appropriate conditions that could be recognized by one skilled in the art.

| Compound | Structure | MS (m/z) (M + H)$^+$ |
|---|---|---|
| 121 | (structure) | 320 |
| 122 | (structure) | 426 |

81

-continued

| Compound | Structure | MS (m/z) (M + H)+ |
|---|---|---|
| 123 | 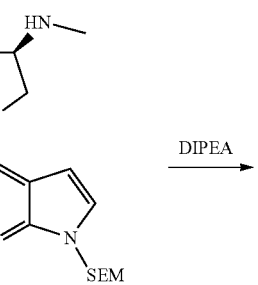 | 363 |
| 124 | 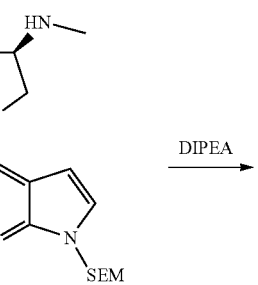 | 360 |

Compound 125

(R)—N-(1-(7H-pyrrolo[2,3-d]pyrimidin-4-yl)pyrrolidin-3-yl)-N-methyl-1H-pyrazolo[3,4-c]pyridin-5-amine

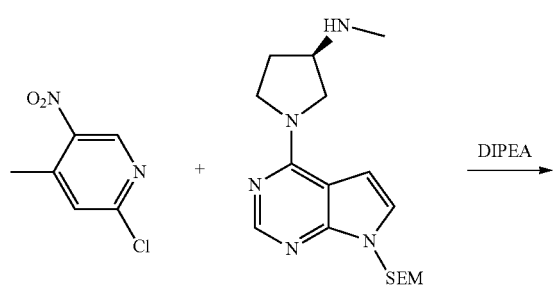

82

-continued

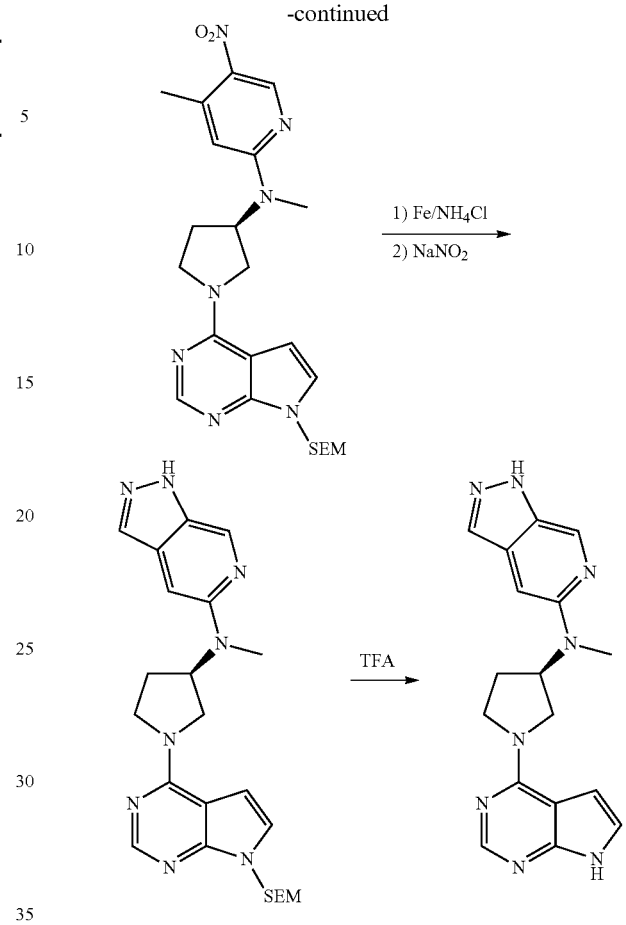

(A) (R)—N,4-dimethyl-5-nitro-N-(1-(7-((2-(trimethylsilyl)ethoxy)methyl)-7H-pyrrolo[2,3-d]pyrimidin-4-yl)pyrrolidin-3-yl)pyridin-2-amine A solution of (R)—N-methyl-1-(7-((2-(trimethylsilyl)ethoxy)methyl)-7H-pyrrolo[2,3-d]pyrimidin-4-yl)pyrrolidin-3-amine (0.287 mmol), 2-chloro-4-methyl-5-nitropyridine (0.347 mmol), and DIPEA (1.435 mmol) in NMP (1.5 mL) was stirred at 200° C. for 30 minutes in a microwave reactor and then cooled to ambient temperature. The solution was poured into water, extracted with EtOAc, concentrated, and purified by column chromatography to give the title compound in 86.3% yield.

(B) (R)—N-methyl-N-(1-(7-((2-(trimethylsilyl)ethoxy)methyl)-7H-pyrrolo[2,3-d]pyrimidin-4-yl)pyrrolidin-3-yl)-1H-pyrazolo[3,4-c]pyridin-5-amine To a solution of (R)—N,4-dimethyl-5-nitro-N-(1-(7-((2-(trimethylsilyl)ethoxy)methyl)-7H-pyrrolo[2,3-d]pyrimidin-4-yl)pyrrolidin-3-yl)pyridin-2-amine (0.248 mmol) in ethanol (20 mL) and water (5 mL), was added iron powder (0.752 mmol) and NH$_4$Cl (1.495 mmol). The mixture was stirred at refluxing temperature for 2 hours, cooled, and filtered. The filtrate was concentrated, and dissolved in CH$_3$COOH (1.5 mL) and water (2.5 mL). NaNO$_2$ (0.304 mmol) was then slowly added, and the mixture was stirred at room temperature overnight, which was subsequently treated with NH$_3$.H$_2$O and extracted with EtOAc (3×20 mL). The combined extracts were concentrated and the residue was purified by column chromatography to give the title compound in 33.0% yield.

(C) (R)—N-(1-(7H-pyrrolo[2,3-d]pyrimidin-4-yl)pyrrolidin-3-yl)-N-methyl-1H-pyrazolo[3,4-c]pyridin-5-amine The title compound was prepared according to the procedures of Compound 23 (B) using (R)—N-methyl-N-(1-(7-((2-(trimethylsilyl)ethoxy)methyl)-7H-pyrrolo[2,3-d]pyrimidin-4-yl)pyrrolidin-3-yl)-1H-pyrazolo[3,4-c]pyridin-5-amine.MS (m/z): 335 (M+H)+.

Compound 126

(R)-6-((1-(7H-pyrrolo[2,3-d]pyrimidin-4-yl)pyrrolidin-3-yl)(ethyl)amino)-nicotinonitrile

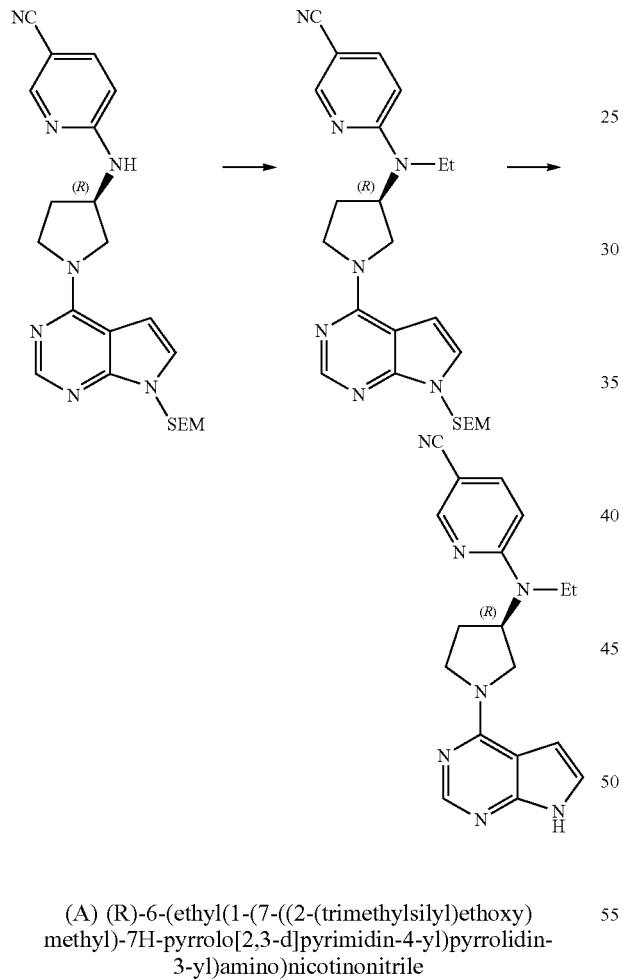

(A) (R)-6-(ethyl(1-(7-((2-(trimethylsilyl)ethoxy)methyl)-7H-pyrrolo[2,3-d]pyrimidin-4-yl)pyrrolidin-3-yl)amino)nicotinonitrile To a solution of (R)-6-(1-(7-((2-(trimethylsilyl)ethoxy)methyl)-7H-pyrrolo[2,3-d]pyrimidin-4-yl)pyrrolidin-3-ylamino)nicotinonitrile (200 mg, 0.46 mmol) in DMF (5.0 mL) was added NaH (55 mg, 2.3 mmol) in portions at 0° C. The reaction mixture was stirred at ambient temperature for 30 minutes, bromoethane (60 mg, 0.55 mmol) was then added dropwise and the reaction mixture was stirred at ambient temperature for additional 30 minutes. The reaction mixture was quenched with saturated NH4Cl (10 mL) and extracted with EtOAc (3×20 mL). The combined extracts were washed with brine, dried over anhydrous Na2SO4, filtered, and concentrated under reduced pressure. The residue was purified by chromatography to give the title compound. MS (m/z): 464 (M+H)+.

(B) (R)-6-((1-(7H-pyrrolo[2,3-d]pyrimidin-4-yl)pyrrolidin-3-yl)(ethyl)amino)-nicotinonitrile The title compound was prepared according to the procedures of Compound 23 (B) using (R)-6-(ethyl(1-(7-((2-(trimethylsilyl)ethoxy)methyl)-7H-pyrrolo[2,3-d]pyrimidin-4-yl)pyrrolidin-3-yl)amino)nicotinonitrile. MS (m/z): 334 (M+H)+.

The following compounds were prepared according to the procedures of Compound 126 using the corresponding intermediates and reagents under appropriate conditions that could be recognized by one skilled in the art.

| Compound | Structure | MS (m/z) (M + H)+ |
|---|---|---|
| 127 | (structure) | 345 |
| 128 | (structure) | 344 |

85
-continued
| Compound | Structure | MS (m/z) (M + H)+ |
|---|---|---|
| 129 | 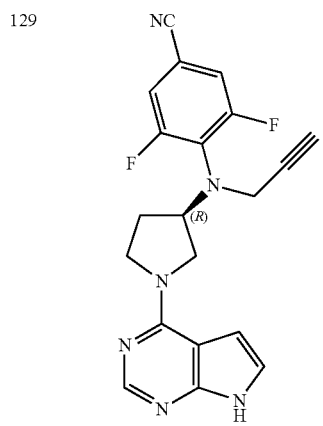 | 379 |
| 130 | 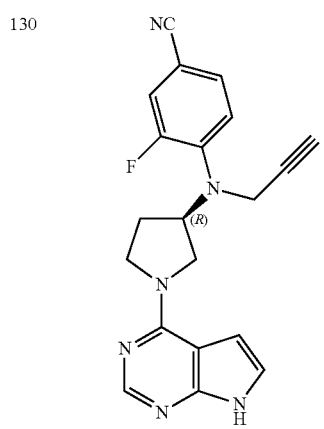 | 361 |
| 131 | 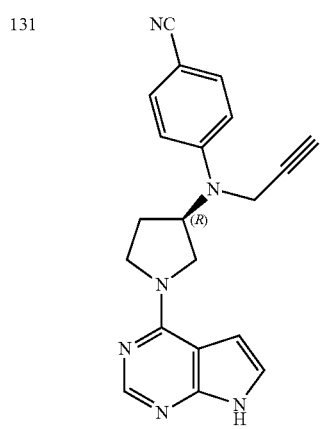 | 343 |
86
-continued
| Compound | Structure | MS (m/z) (M + H)+ |
|---|---|---|
| 132 | 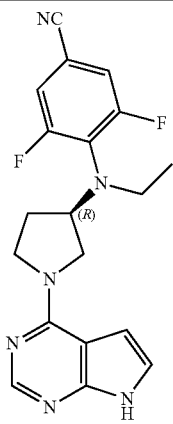 | 369 |
| 133 | 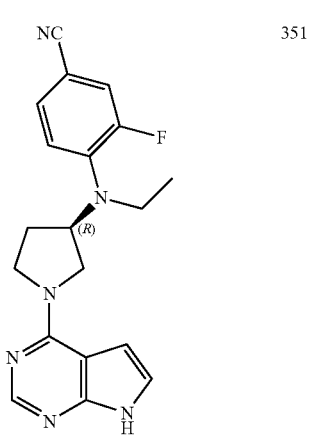 | 351 |
Compound 134
(R)—N-(1-7H-pyrrolo[2,3-d]pyrimidin-4-yl)pyrrolidin-3-yl)-N-methyl-5-morpholinopyrazin-2-amine
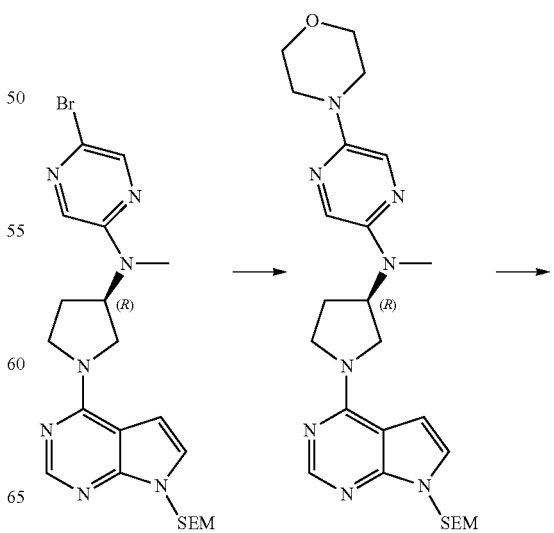

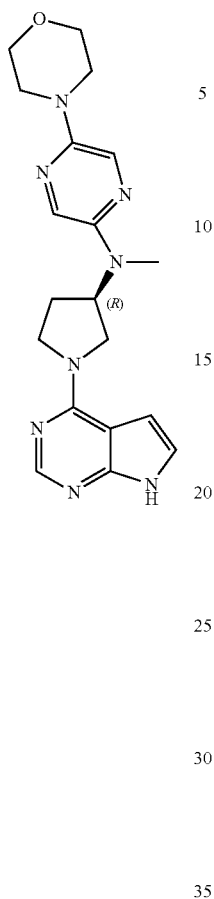

(A) (R)—N-methyl-5-morpholino-N-(1-(7-((2-(trimethylsilyl)ethoxy)methyl)-7H-pyrrolo[2,3-d]pyrimidin-4-yl)pyrrolidin-3-yl)pyrazin-2-amine A solution of (R)-5-bromo-N-methyl-N-(1-(7-((2-(trimethylsilyl)ethoxy)methyl)-7H-pyrrolo[2,3-d]pyrimidin-4-yl)pyrrolidin-3-yl)pyrazin-2-amine (0.099 mmol) and morpholine (1.5 mL) in NMP (0.5 mL) was stirred at 195° C. for 2 hours in a microwave reactor. After cooling to the ambient temperature, it was poured into water, and extracted with EtOAc. The combined organic extracts were concentrated and the residue was purified by column chromatography on silica gel to give the title compound.

(B) (R)—N-(1-(7H-pyrrolo[2,3-d]pyrimidin-4-yl)pyrrolidin-3-yl)-N-methyl-5-morpholinopyrazin-2-amine The title compound was prepared according to the procedures of Compound 23 (B) using (R)—N-methyl-5-morpholino-N-(1-(7-((2-(trimethylsilyl)ethoxy)methyl)-7H-pyrrolo[2,3-d]pyrimidin-4-yl)pyrrolidin-3-yl)pyrazin-2-amine. MS (m/z): 381 (M+H)⁺.

The following compounds were prepared according to the procedures of Compound 134 using the corresponding intermediates and reagents under appropriate conditions that could be recognized by one skilled in the art.

| Compound | Structure | MS (m/z) (M + H)⁺ |
|---|---|---|
| 135 | 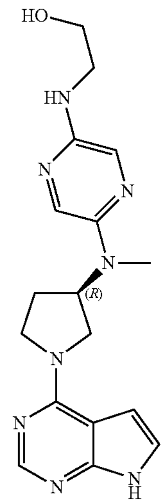 | 355 |
| 136 | 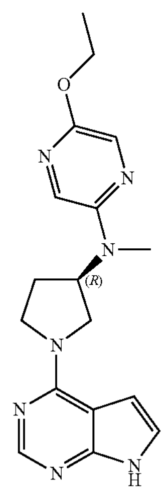 | 340 |
| 137 | 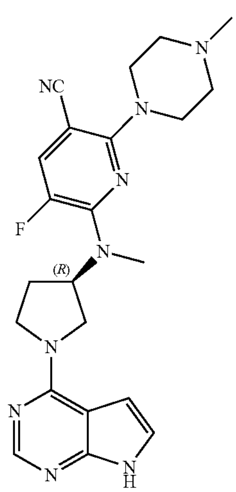 | 436 |

| Compound | Structure | MS (m/z) (M + H)+ |
|---|---|---|
| 138 | 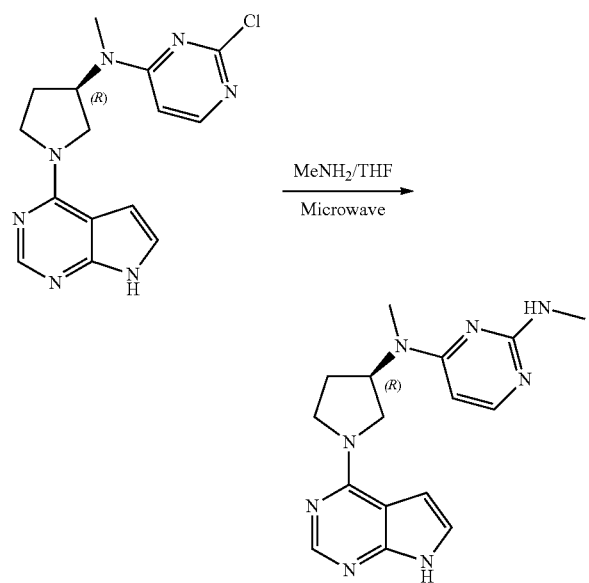 | 365 |

| Compound | Structure | MS (m/z) (M + H)+ |
|---|---|---|
| 140 | 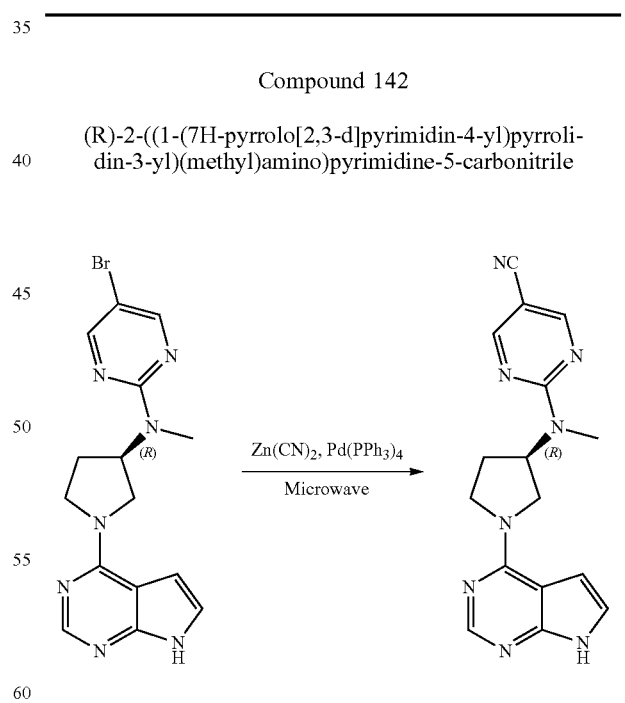 | 311 |
| 141 | 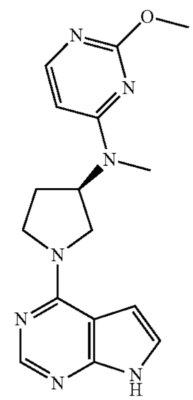 [SMILES: COc1nccc(N(C)[C@@H]2CCN(c3ncnc4[nH]ccc34)C2)n1] | 326 |

Compound 139

(R)—N⁴-(1-(7H-pyrrolo[2,3-d]pyrimidin-4-yl)pyrrolidin-3-yl)-N²,N⁴-dimethylpyrimidine-2,4-diamine Compound 142

(R)-2-((1-(7H-pyrrolo[2,3-d]pyrimidin-4-yl)pyrrolidin-3-yl)(methyl)amino)pyrimidine-5-carbonitrile A mixture of (R)—N-(1-(7H-pyrrolo[2,3-d]pyrimidin-4-yl)pyrrolidin-3-yl)-2-chloro-N-methylpyrimidin-4-amine (26.0 mg, 0.08 mmol) and methylamine (in THF, 2.0 M, 0.5.0 mL, 10.0 mmol) was stirred at 110° C. for 45 min in an Initiator™ Biotage microwave reactor. The volatiles were removed under reduced pressure and the residue was purified by chromatography on silica gel to give the title compound. MS (m/z): 325 (M+H)+.

The following compounds were prepared according to the procedures of Compound 139 using the corresponding reagent under appropriate conditions that will be recognized by one skilled in the art.

A mixture of (R)—N-(1-(7H-pyrrolo[2,3-d]pyrimidin-4-yl)pyrrolidin-3-yl)-5-bromo-N-methylpyrimidin-2-amine (50.0 mg, 0.134 mmol), dicyanozinc (15.7 mg, 0.134 mmol) and tetrakis(triphenylphosphine)palladium (15.4 mg, 0.0134 mmol) in 5 mL of DMF was stirred at 120° C. for 40 min in an Initiator™ Biotage microwave reactor. The reaction mixture was partitioned between 15 mL of water and 20 mL of ethyl acetate. The organic layer was washed by brine, dried, concentrated and the residue was purified by preparative TLC to afford the title compound. MS (m/z): 321 (M+H)+.

Compound 143

(R)—N-(1-(7H-pyrrolo[2,3-d]pyrimidin-4-yl)pyrrolidin-3-yl)-N-methylpyrazin-2-amine

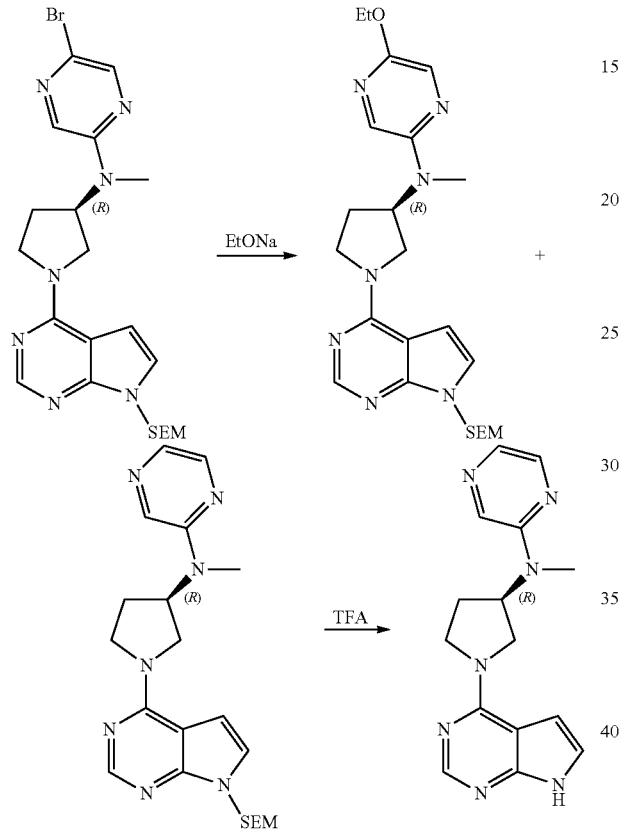

Compound 143

(A) (R)—N-methyl-N-(1-(7-((2-(trimethylsilyl)ethoxy)methyl)-7H-pyrrolo[2,3-d]pyrimidin-4-yl)pyrrolidin-3-yl)pyrazin-2-amine A solution of (R)-5-bromo-N-methyl-N-(1-(7-((2-(trimethylsilyl)ethoxy)methyl)-7H-pyrrolo[2,3-d]pyrimidin-4-yl)pyrrolidin-3-yl)pyrazin-2-amine (55 mg, 0.10 mmol) and sodium ethoxide (680 mg, 10 mmol) in EtOH (10.5 mL) was stirred at refluxing temperature for 5 days. It was then treated with water and extracted with EtOAc (2×30 mL). The combined extracts were concentrated and the residue was purified by chromatography on silica gel (PE/EtOAc=1/1). The first compound from the column was collected and confirmed to be (R)-5-ethoxy-N-methyl-N-(1-(7-((2-(trimethylsilyl)ethoxy)-methyl)-7H-pyrrolo[2,3-d]pyrimidin-4-yl)pyrrolidin-3-yl)pyrazin-2-amine [MS (m/z), 470 (M+1)+, 21 mg, 41.1% yield) and the later compound from the column was isolated and concentrated to give the title compound (22 mg, 47.8% yield). MS (m/z), 426 (M+1)+

(B) (R)—N-(1-(7H-pyrrolo[2,3-d]pyrimidin-4-yl)pyrrolidin-3-yl)-N-methylpyrazin-2-amine The title compound was prepared according to the procedures of Compound 23 (B) using (R)—N-methyl-N-(1-(7-((2-(trimethylsilyl)ethoxy)methyl)-7H-pyrrolo[2,3-d]pyrimidin-4-yl)pyrrolidin-3-yl)pyrazin-2-amine. MS (m/z): 296 (M+H)+.

Compound 144

(R)—N-(1-(7H-pyrrolo[2,3-d]pyrimidin-4-yl)pyrrolidin-3-yl)-N-methyl-3,4'-b]pyridin-6-amine

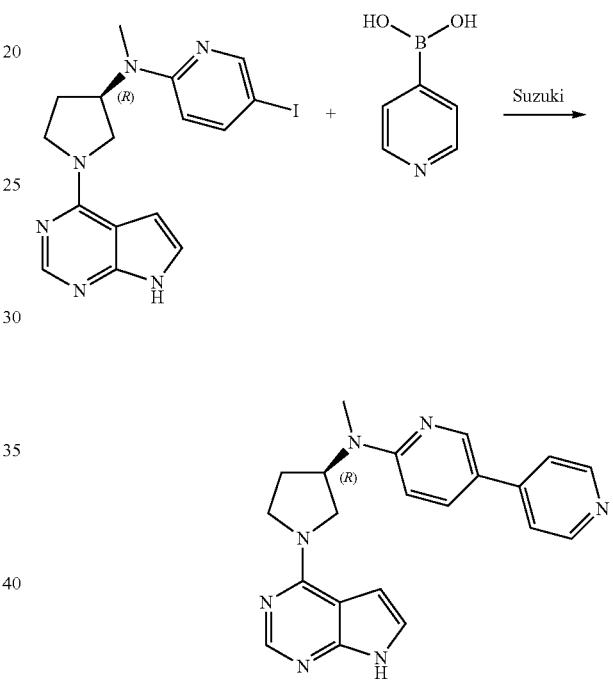

Under $N_2$, a mixture of (R)—N-(1-(7H-pyrrolo[2,3-d]pyrimidin-4-yl)pyrrolidin-3-yl)-5-iodo-N-methylpyridin-2-amine (90.0 mg, 0.21 mmol), pyridin-4-yl boronic acid (28.4 mg, 0.23 mmol), $PdCl_2dppf.CH_2Cl_2$ (17.2 mg, 0.02 mmol) and $K_2CO_3$ (0.058 g) in DMF (5.0 mL) was stirred at 110° C. for 16 h. It was then cooled to ambient temperature, diluted with water (5.0 mL) and extracted with ethyl acetate (3×10 mL). The combined extracts was washed with brine (3×5.0 mL), dried over $Na_2SO_4$ (anhydrous), filtered and concentrated. The residue was purified by flash chromatography to give the title product. MS (m/z): 372 (M+H)+.

The following compounds were prepared according to the procedures of Compound 144 using the corresponding intermediates and reagents under appropriate conditions that could be recognized by one skilled in the art.

| Compound | Structure | MS (m/z) (M + H)+ |
|---|---|---|
| 145 | 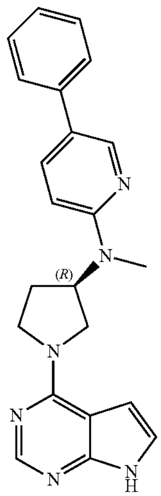 | 371 |
| 146 | 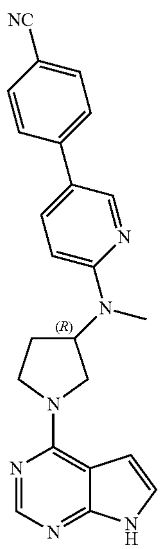 | 396 |
| 147 | 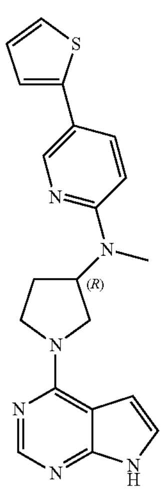 | 377 |
| 148 | | 420 |
| 149 | | 375 |
| 150 | | 361 |

Compound 151

N—((R)-1-(7H-pyrrolo[2,3-d]pyrimidin-4-yl)pyrrolidin-3-yl)-N-methyl-5-(1H-pyrazol-4-yl)pyrazin-2-amine

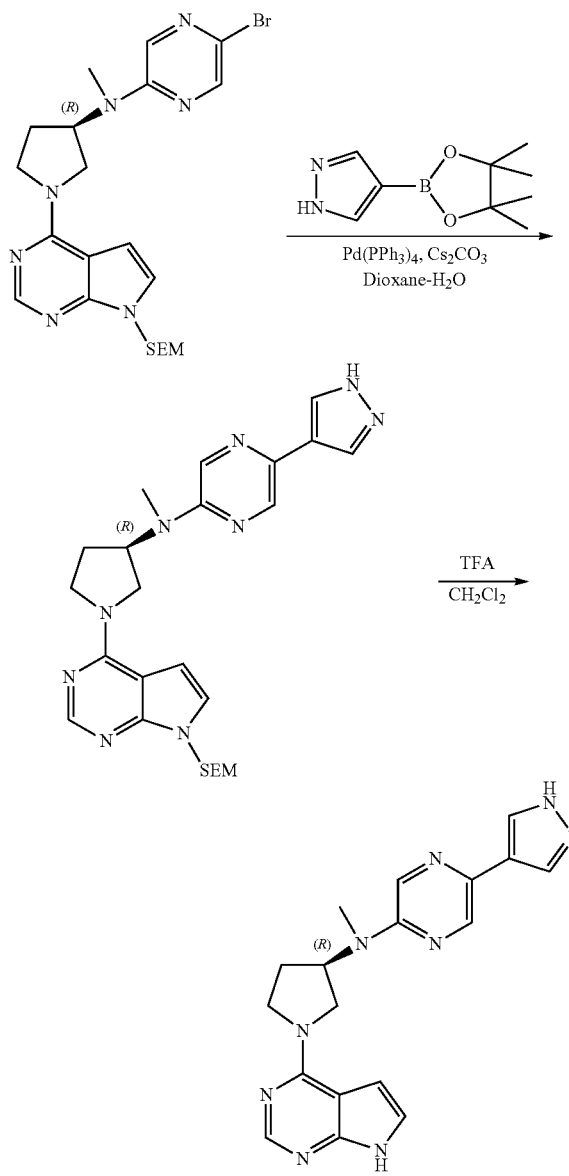

(A) (R)—N-methyl-5-(1H-pyrazol-4-yl)-N-(1-(7-((2-(trimethylsilyl)ethoxy)methyl)-7H-pyrrolo[2,3-d]pyrimidin-4-yl)pyrrolidin-3-yl)pyrazin-2-amine Under N₂, a mixture of (R)-5-bromo-N-methyl-N-(1-(7-((2-(trimethylsilyl)ethoxy)methyl)-7H-pyrrolo[2,3-d]pyrimidin-4-yl)pyrrolidin-3-yl)pyrazin-2-amine (64 mg, 0.127 mmol), 4-pyrazoleboronic acid pinacol ester (37 mg, 0.19 mmol), Pd(PPh₃)₄(29 mg, 0.0254 mmol), Cs₂CO₃ (124 mg, 0.381 mmol) in 1,4-Dioxane (3 mL)/water (0.3 mL) was stirred at reflux for 14 h. It was then cooled to ambient temperature, diluted with EtOAc and H₂O, and extracted with EtOAc. The combined extracts was washed with brine (50 mL), dried over Na₂SO₄, concentrated in vacuo, and purified by flash chromatography to give the title compound.

(B) N—((R)-1-(7H-pyrrolo[2,3-d]pyrimidin-4-yl)pyrrolidin-3-yl)-N-methyl-5-(1H-pyrazol-4-yl)pyrazin-2-amine The title compound was prepared according to the procedures of Compound 23 (B) using (R)—N-methyl-5-(1H-pyrazol-4-yl)-N-(1-(7-((2-(trimethylsilyl)ethoxy)methyl)-7H-pyrrolo[2,3-d]pyrimidin-4-yl)pyrrolidin-3-yl)pyrazin-2-amine. MS (m/z): 362 (M+H)⁺.

The following compound was prepared according to the procedures of Compound 151 using the corresponding intermediates and reagents under appropriate conditions that could be recognized by one skilled in the art.

| Compound | Structure | MS (m/z) (M + H)⁺ |
|---|---|---|
| 152 | 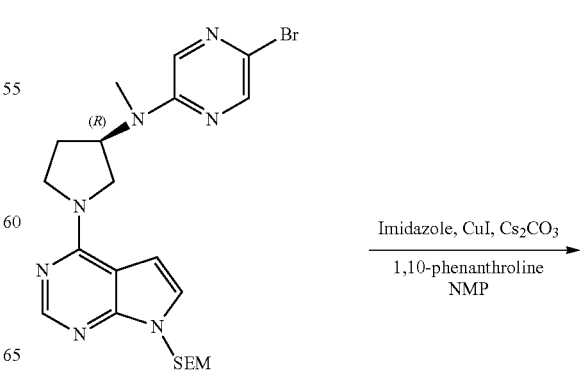 | 362 |

Compound 153

N—((R)-1-(7H-pyrrolo[2,3-d]pyrimidin-4-yl)pyrrolidin-3-yl)-5-(1H-imidazol-1-yl)-N-methylpyrazin-2-amine

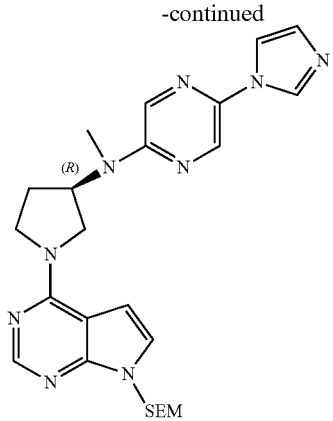

↓

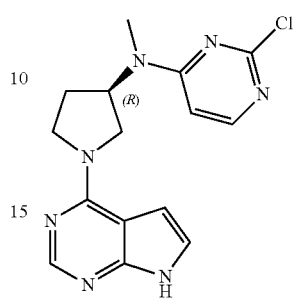

Compound 154

(R)—N-(1-(7H-pyrrolo[2,3-d]pyrimidin-4-yl)pyrrolidin-3-yl)-N-methylpyrimidin-4-amine

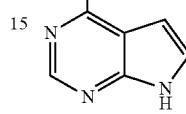

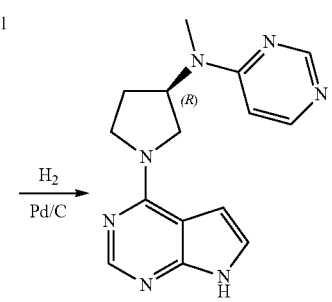

Under the atmosphere of hydrogen, a mixture of (R)—N-(1-(7H-pyrrolo[2,3-d]pyrimidin-4-yl)pyrrolidin-3-yl)-2-chloro-N-methylpyrimidin-4-amine (30 mg, 0.09 mmol), Pd/C (10 wt. %, 20.0 mg) was stirred in 3.0 mL methanol at ambient temperature for 4 h. The catalyst was removed by filtration and the filtrate was concentrated. The residue was purified by preparative TLC (DCM/MeOH=15/1) to give the title compound. MS (m/z): 296 (M+H)+.

The following compounds were prepared according to the procedures of Compound 154 using the corresponding intermediates and reagents under appropriate conditions that could be recognized by one skilled in the art.

(A) 5-(1H-imidazol-1-yl)-N-methyl-N—((R)-1-(7-((2-(trimethylsilyl)ethoxy)methyl)-7H-pyrrolo[2,3-d]pyrimidin-4-yl)pyrrolidin-3-yl)pyrazin-2-amine A mixture of (R)-5-bromo-N-methyl-N-(1-(7-((2-(trimethylsilyl)ethoxy)methyl)-7H-pyrrolo[2,3-d]pyrimidin-4-yl)pyrrolidin-3-yl)pyrazin-2-amine (50 mg, 0.0991 mmol), imidazole (14 mg, 0.198 mmol), CuI (9.4 mg, 0.050 mmol), Cs₂CO₃ (32 mg, 0.0991 mmol), and 1,10-phenanthroline (9 mg, 0.050 mmol), in NMP (2 mL) was stirred at 180° C. for 45 minutes in a microwave reactor. It was then cooled to the ambient temperature and diluted with H₂O, extracted with EtOAc, washed with brine, dried, and concentrated in vacuo. The residue was purified by flash chromatography on silica gel to give the title compound (20 mg, 41%).

(B) N—((R)-1-(7H-pyrrolo[2,3-d]pyrimidin-4-yl)pyrrolidin-3-yl)-5-(1H-imidazol-1-yl)-N-methylpyrazin-2-amine The title compound was prepared according to the procedures of Compound 23 (B) using 5-(1H-imidazol-1-yl)-N-methyl-N—((R)-1-(7-((2-(trimethylsilyl)ethoxy)methyl)-7H-pyrrolo[2,3-d]pyrimidin-4-yl)pyrrolidin-3-yl)pyrazin-2-amine. MS (m/z): 362 (M+H)+.

| Compound | Structure | MS (m/z) (M + H)+ |
|---|---|---|
| 155 | 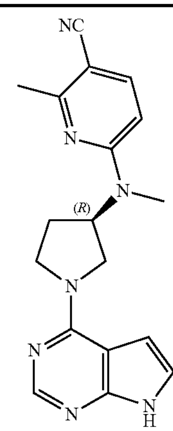 | 334 |
| 156 | 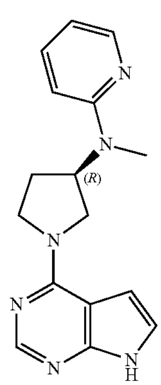 | 295 |

99
-continued

| Compound | Structure | MS (m/z) (M + H)+ |
|---|---|---|
| 157 | 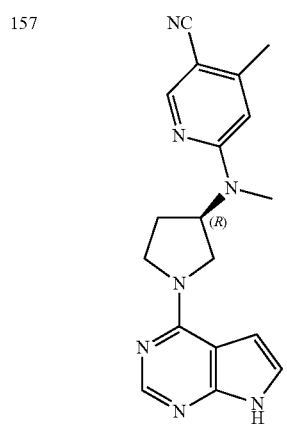 | 334 |
| 158 | 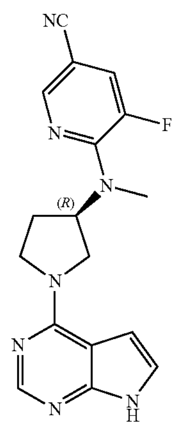 | 338 |
| 159 | 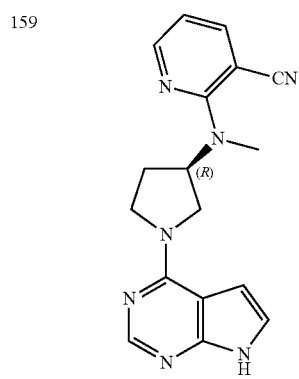 | 320 |

100

Compound 160

(R)—N-(1-(7H-pyrrolo[2,3-d]pyrimidin-4-yl)pyrrolidin-3-yl)-N-methyl-5-(2H-tetrazol-5-yl)pyridin-2-amine

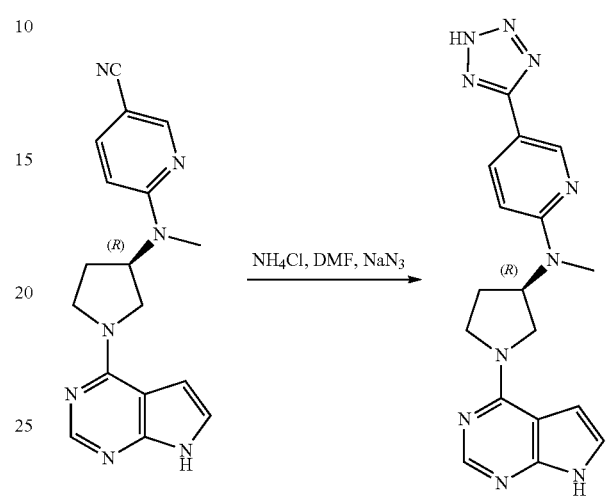

A mixture of (R)-6-((1-(7H-pyrrolo[2,3-d]pyrimidin-4-yl)pyrrolidin-3-yl)(methyl)amino)nicotinonitrile (100 mg, 0.3 mmol), ammonia chloride (84 mg, 1.57 mmol) and sodium azide (108 mg, 1.66 mmol) in N,N-dimethylformamide (5.0 mL) was stirred at 120° C. for 16 h. The volatile was removed under vacuum and the residue was purified by chromatography on silica gel to give the title compound. MS (m/z): 363.0 (M+H)+.

The following compound was prepared according to the procedures of Compound 160 using the corresponding intermediates and reagents under appropriate conditions that could be recognized by one skilled in the art.

| Compound | Structure | MS (m/z) (M + H)+ |
|---|---|---|
| 161 | 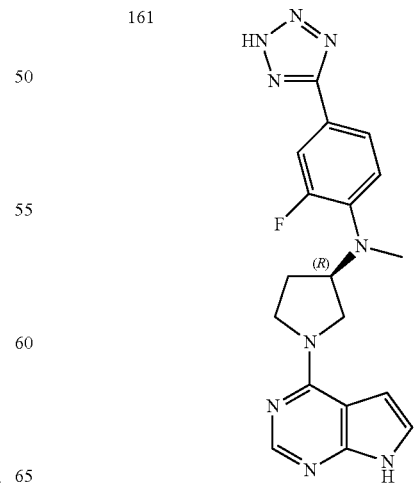 | 380 |

Compound 162

(R)—N-(1-(7H-pyrrolo[2,3-d]pyrimidin-4-yl)pyrrolidin-3-yl)-5-ethynyl-N-methylpyridin-2-amine

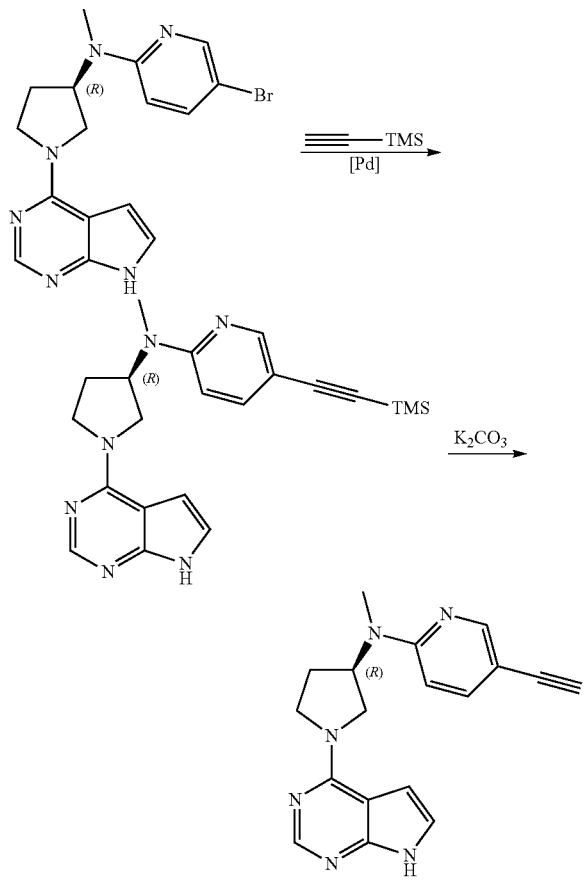

(A) (R)—N-(1-(7H-pyrrolo[2,3-d]pyrimidin-4-yl)pyrrolidin-3-yl)-N-methyl-5-(((trimethylsilyl)ethynyl)pyridin-2-amine Under N$_2$, a mixture of (R)—N-(1-(7H-pyrrolo[2,3-d]pyrimidin-4-yl)pyrrolidin-3-yl)-5-bromo-N-methylpyridin-2-amine (0.22 g, 0.58 mmol), ethynyltrimethylsilane (0.22 mL, 1.6 mmol), Et$_3$N (0.24 mL, 1.5 mmol), CuI (5.0 mg, 0.03 mmol), PdCl$_2$(PPh$_3$)$_2$ (8.0 mg, 0.01 mmol) and PPh$_3$ (3.0 mg, 0.01 mmol) in DMF (3.0 mL) was stirred at 90° C. for 4 h. The reaction was then cooled to ambient temperature, diluted with water (3 mL), extracted with ethyl acetate (2×10 mL). The combined extracts was washed with brine (2×6 mL), dried over anhydrous Na$_2$SO$_4$, filtered, and concentrated. The residue was purified by chromatography on silica gel to give the titled compound. MS (m/z): 295 (M+H)$^+$.

(B) (R)—N-(1-(7H-pyrrolo[2,3-d]pyrimidin-4-yl)pyrrolidin-3-yl)-5-ethynyl-N-methylpyridin-2-amine A mixture of (R)—N-(1-(7H-pyrrolo[2,3-d]pyrimidin-4-yl)pyrrolidin-3-yl)-N-methyl-5-((trimethylsilyl)ethynyl)pyridin-2-amine (26 mg, 0.06 mmol) and K$_2$CO$_3$ (20.0 mg) in MeOH (4.0 mL) was stirred at the ambient temperature for 16 hours. The volatiles were removed and the residue was purified by chromatography on silica gel to give the title compound. MS (m/z): 319 (M+H)$^+$.

Compound 163

(R)—N-(1-(7H-pyrrolo[2,3-d]pyrimidin-4-yl)pyrrolidin-3-yl)-N-methyl-3H-imidazo[4,5-b]pyridin-5-amine

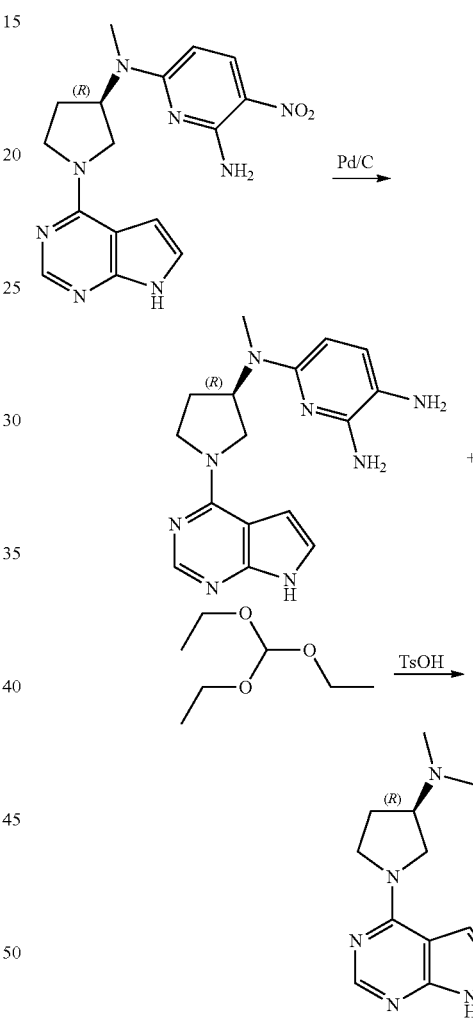

(A) (R)—N$^2$-(1-(7H-pyrrolo[2,3-d]pyrimidin-4-yl)pyrrolidin-3-yl)-N$^2$-methylpyridine-2,5,6-triamine A solution of (R)—N$^2$-(1-(7H-pyrrolo[2,3-d]pyrimidin-4-yl)pyrrolidin-3-yl)-N$^2$-methyl-5-nitropyridine-2,6-diamine (320 mg, 0.90 mmol) in ethanol (35 mL) was degassed and purged with N$_2$. Pd/C (10%, 100 mg) was added, degassed and purged with H$_2$ and then stirred under hydrogen atmosphere at ambient temperature for 20 hours. The catalyst was removed by filtration and the filtrate was concentrated to give the title product. MS (m/z): 325 (M+H)$^+$.

(B) (R)—N-(1-(7H-pyrrolo[2,3-d]pyrimidin-4-yl)pyrrolidin-3-yl)-N-methyl-3H-Imidazo[4,5-b]pyridin-5-amine A solution of (R)—N²-(1-(7H-pyrrolo[2,3-d]pyrimidin-4-yl)pyrrolidin-3-yl)-N-methylpyridine-2,5,6-triamine (35 mg, 0.11 mmol), triethoxymethane (0.58 mL, 3.45 mmol) and 4-methylbenzenesulfonic acid monohydrate (62 mg, 0.33 mmol) in methanol (3.0 mL) was stirred at 150° C. for 5 min in an Initiator™ Biotage microwave reactor. The volatiles were removed and the residue is purified by chromatography to give the title product. MS (m/z): 335 (M+H)⁺.

Compound 164

(R)-5-((1-(7H-pyrrolo[2,3-d]pyrimidin-4-yl)pyrrolidin-3-yl)(methyl)amino)-1H-imidazo[4,5-b]pyridin-2(3H)-one

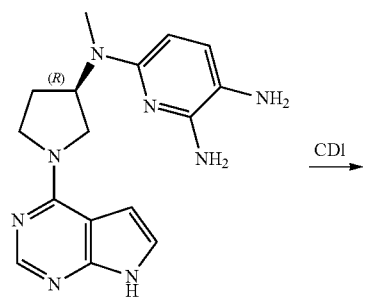

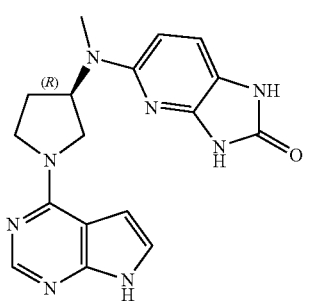

A solution of (R)—N²-(1-(7H-pyrrolo[2,3-d]pyrimidin-4-yl)pyrrolidin-3-yl)-N²-methylpyridine-2,5,6-triamine (35 mg, 0.11 mmol,) and 1,1'-carbonyldiimidazole (21 mg, 0.13 mmol) in tetrahydrofuran (3.0 mL) was stirred at reflux for 1 h. The volatiles were removed and the residue was purified by chromatography to give the title compound. MS (m/z): 351 (M+H)⁺.

Compound 165

(R)-3-(1-(7H-pyrrolo[2,3-d]pyrimidin-4-yl)pyrrolidin-3-yl)-2-oxo-2,3-dihydro-1H-imidazo[4,5-b]pyridine-6-carbonitrile

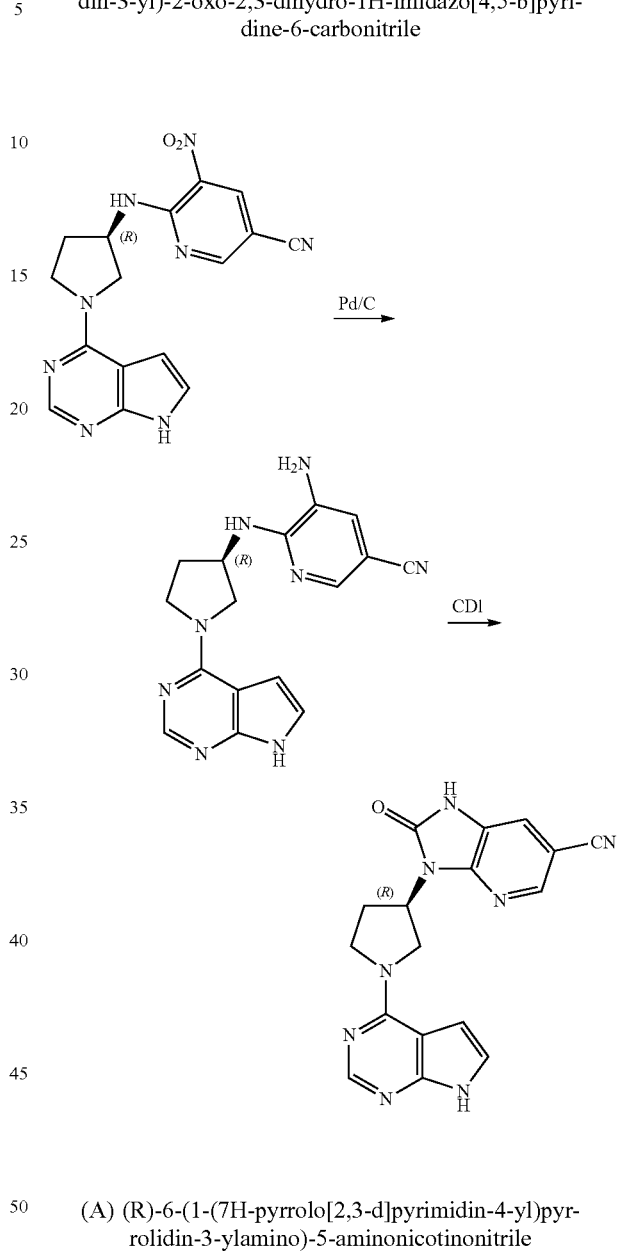

(A) (R)-6-(1-(7H-pyrrolo[2,3-d]pyrimidin-4-yl)pyrrolidin-3-ylamino)-5-aminonicotinonitrile The tile compound was prepared according to the procedure of Compound 163 (A) using (R)-6-(1-(7H-pyrrolo[2,3-d]pyrimidin-4-yl)pyrrolidin-3-ylamino)-5-nitronicotinonitrile. MS (m/z): 321 (M+H)⁺.

(B) (R)-3-(1-(7H-pyrrolo[2,3-d]pyrimidin-4-yl)pyrrolidin-3-yl)-2-oxo-2,3-dihydro-1H-imidazo[4,5-b]pyridine-6-carbonitrile The tile compounds was prepared according to the procedure of Compound 164 using R)-6-(1-(7H-pyrrolo[2,3-d]pyrimidin-4-yl)pyrrolidin-3-ylamino)-5-aminonicotinonitrile. MS (m/z): 347 (M+H)⁺.

Compound 166

(R)-4-((1-(7H-pyrrolo[2,3-d]pyrimidin-4-yl)pyrrolidin-3-yl)(methyl)amino)-3-aminobenzonitrile

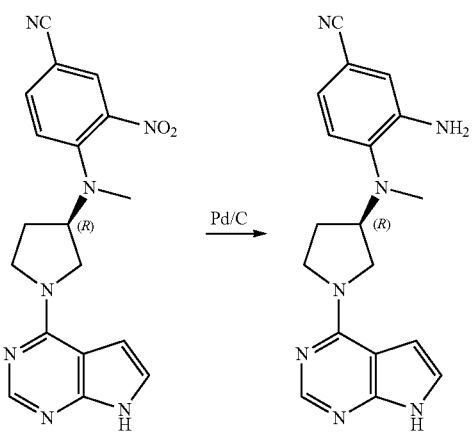

The title compound was prepared according to the procedures of Compound 163 using (R)-4-((1-(7H-pyrrolo[2,3-d]pyrimidin-4-yl)pyrrolidin-3-yl)(methyl)amino)-3-nitrobenzonitrile. MS (m/z): 334 (M+H)$^+$.

Compound 167

(R)—N-(1-(7H-pyrrolo[2,3-d]pyrimidin-4-yl)pyrrolidin-3-yl)-N-methyl-3H-[1,2,3]triazolo[4,5-b]pyridin-5-amine

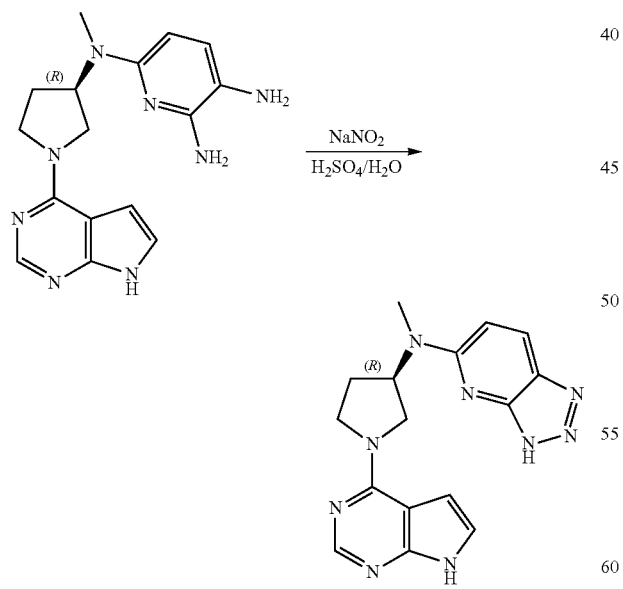

To a suspension of (R)—N$^2$-(1-(71H-pyrrolo[2,3-d]pyrimidin-4-yl)pyrrolidin-3-yl)-N$^2$-methylpyridine-2,5,6-triamine (50 mg, 0.15 mmol,) in water (0.6 mL) was added concentrated sulfuric acid (23 uL). The mixture was stirred at room temperature for 1 h. It was cooled to 0° C., and aqueous sodium nitrite (17 mg, 0.25 mmol, in 0.1 mL of water) was added. The reaction mixture was stirred at 0° C. for 1 h. It was then neutralized till pH equal to 5 with aqueous NaHCO$_3$ (10%) and extracted with EtOAc (3×10 mL). The combined extracts were washed with brine (2×10 mL), concentrated, and the residue was purified by chromatography to give the title compound. MS (m/z): 336 (M+H)$^+$.

Compound 168

(R)-methyl 6-((1-(7H-pyrrolo[2,3-d]pyrimidin-4-yl)pyrrolidin-3-yl)methyl)amino)nicotinate

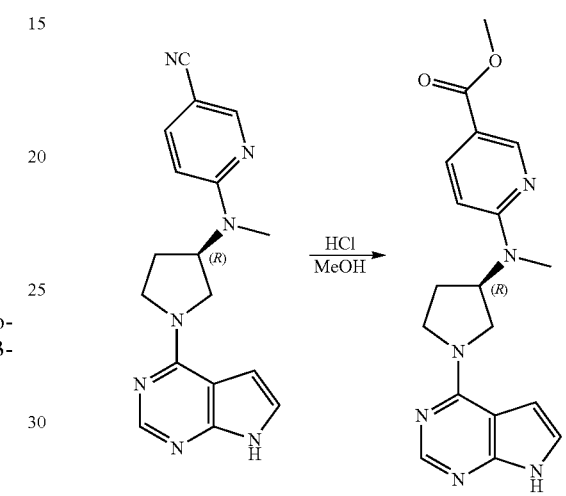

A solution of (R)-6-((1-(7H-pyrrolo[2,3-d]pyrimidin-4-yl)pyrrolidin-3-yl)(methyl)amino)nicotinonitrile (31.9 mg, 0.1 mmol) in hydrogen chloride (6M in MeOH, 5.0 ml) was stirred at 65° C. for 14 h. The volatiles were removed under reduced pressure and the residue was purified by silica gel chromatography to give the title compound. MS (m/z): 353 (M+H)$^+$.

Compound 169

(R)-6-((1-(7H-pyrrolo[2,3-d]pyrimidin-4-yl)pyrrolidin-3-yl)(methyl)amino)nicotinamide

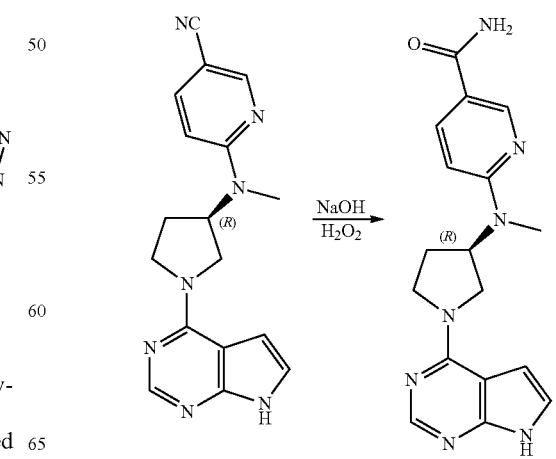

A solution of (R)-6-((1-(7H-pyrrolo[2,3-d]pyrimidin-4-yl)pyrrolidin-3-yl)(methyl)amino) nicotinonitrile (31.9 mg, 0.1 mmol), aqueous sodium hydroxide (1.0 M, 0.7 mL, 0.7 mmol,) and hydrogen peroxide (30% in H$_2$O, 0.3 mL) in MeOH (1.0 mL) was stirred at ambient temperature for 2 hours and then treated with aqueous Na$_2$SO$_3$ (10%) until no peroxide could be detected. The volatiles were removed under reduced pressure and the residue was extracted with EtOAc (3×20 mL). The combined extracts were washed with brine, concentrated and the residue was purified by silica gel chromatography to give the title compound. MS (m/z): 338 (M+H)$^+$.

Compound 170

(R)-6-((1-(7H-pyrrolo[2,3-d]pyrimidin-4-yl)pyrrolidin-3-yl)(methyl)amino)nicotinic acid

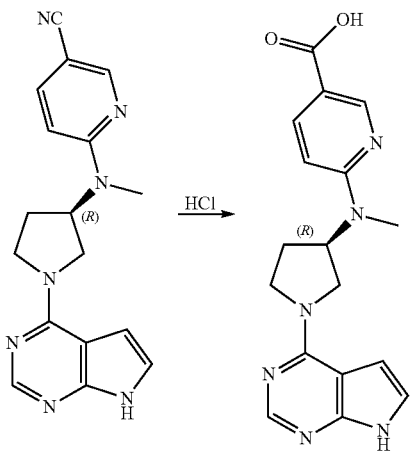

A solution of (R)-6-((1-(7H-pyrrolo[2,3-d]pyrimidin-4-yl)pyrrolidin-3-yl)(methyl)amino)nicotinonitrile (160 mg, 0.5 mmol) in concentrated hydrochloric acid (5.0 mL) was stirred at 100° C. for 14 hours. The volatiles were removed under reduced pressure to give the title compound. MS (m/z): 339 (M+H)$^+$.

Compound 171

(R)-6-((1-(7H-pyrrolo[2,3-d]pyrimidin-4-yl)pyrrolidin-3-yl)(methyl)amino)-N-cyclopropylnicotinamide

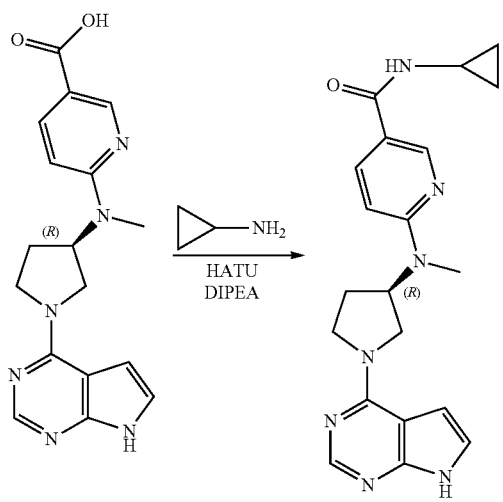

To a solution of (R)-6-((1-(7H-pyrrolo[2,3-d]pyrimidin-4-yl)pyrrolidin-3-yl)(methyl)amino) nicotinic acid (33.8 mg, 0.1 mmol) in DMF (2 mL) were added cyclopropylamine (5.71 mg, 0.2 mmol), DIPEA (26 mg, 0.2 mmol) and HATU (38.0 mg, 0.1 mmol). The reaction mixture was stirred at ambient temperature for 16 hours. The volatiles were removed under reduced pressure and the residue was purified by silica gel chromatography to give the title compound. MS (m/z): 378 (M+H)$^+$.

The following compounds were prepared according to the procedures of Compound 171 using the corresponding intermediates and reagents under appropriate conditions that could be recognized by one skilled in the art.

| Compound | Structure | MS (m/z) (M + H)$^+$ |
|---|---|---|
| 172 | ![structure with HN-Bn] | 428 |
| 173 | ![structure with N,N-dimethyl] | 366 |

-continued

| Compound | Structure | MS (m/z) (M + H)+ |
|---|---|---|
| 174 | 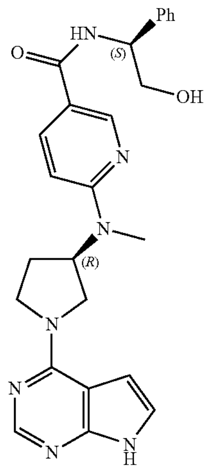 | 458 |
| 175 | 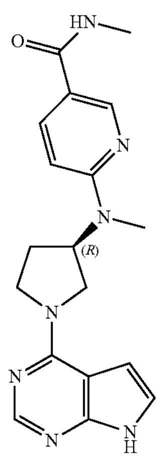 | 352 |
| 176 | 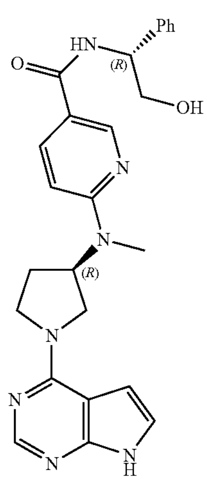 | 458 |

-continued

| Compound | Structure | MS (m/z) (M + H)+ |
|---|---|---|
| 177 | | 432 |
| 178 | | 446 |
| 179 | | 475 |

-continued

| Compound | Structure | MS (m/z) (M + H)+ |
|---|---|---|
| 180 | 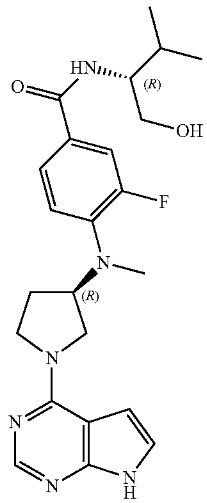 | 441 |
| 181 | 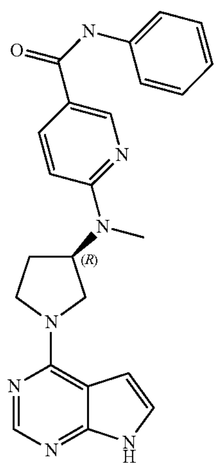 | 414 |
| 182 | 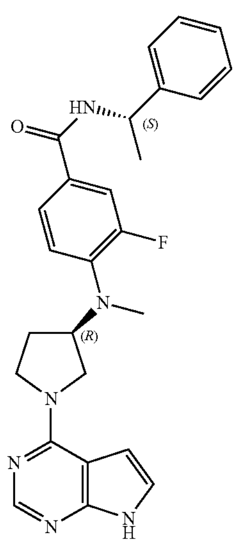 | 459 |

-continued

| Compound | Structure | MS (m/z) (M + H)+ |
|---|---|---|
| 183 | 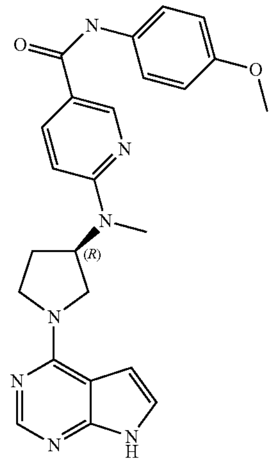 | 444 |
| 184 | 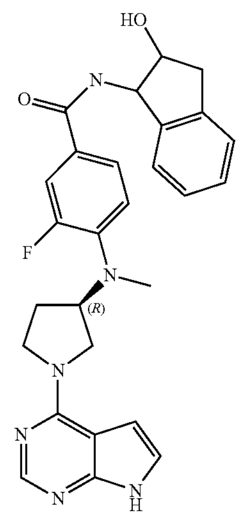 | 487 |
| 185 | 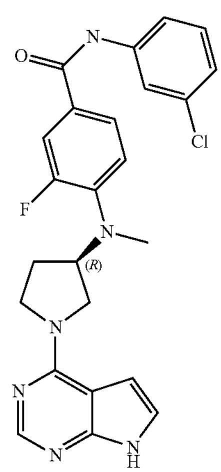 | 465 ($^{35}$Cl)<br>467 ($^{37}$Cl) |

-continued

| Compound | Structure | MS (m/z) (M + H)+ |
|---|---|---|
| 186 | 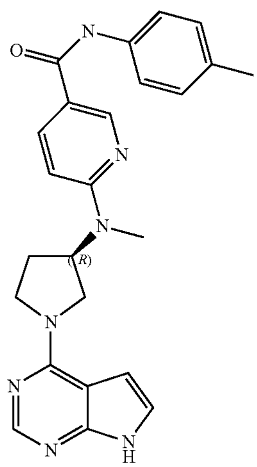 | 428 |
| 187 | 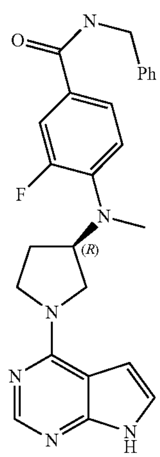 | 445 |
| 188 | 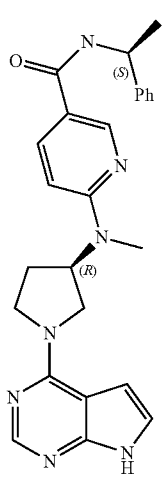 | 442 |
| 189 | | 491 ($^{35}$Cl) 493 ($^{37}$Cl) |
| 190 | | 382 |
| 191 | | 432 |

-continued

| Compound | Structure | MS (m/z) (M + H)+ |
|---|---|---|
| 192 | 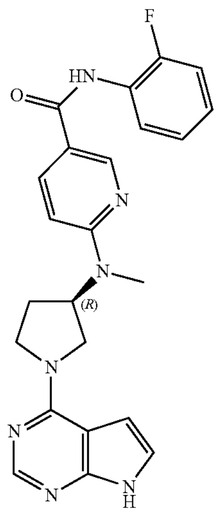 | 432 |
| 193 | 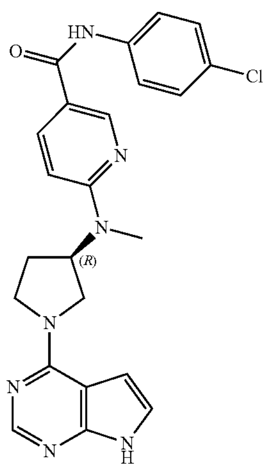 | 448 ($^{35}$Cl) 450 ($^{37}$Cl) |
| 194 | 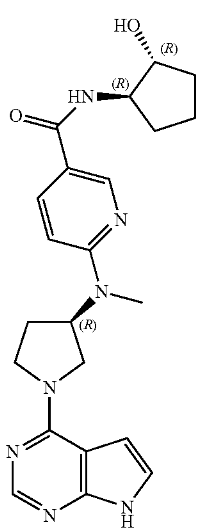 | 422 |

-continued

| Compound | Structure | MS (m/z) (M + H)+ |
|---|---|---|
| 195 | 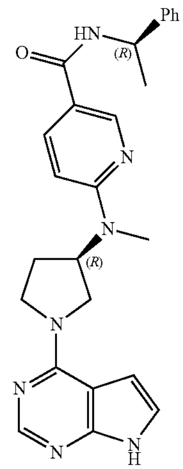 | 442 |
| 196 | 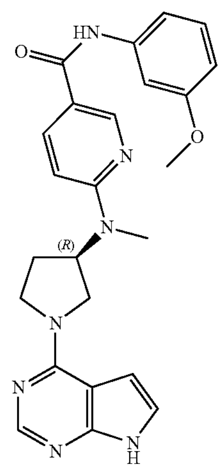 | 444 |
| 197 | 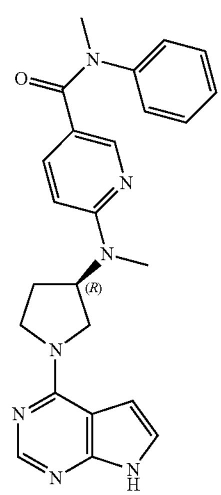 | 428 |

117
-continued
| Compound | Structure | MS (m/z) (M + H)+ |
|---|---|---|
| 198 | 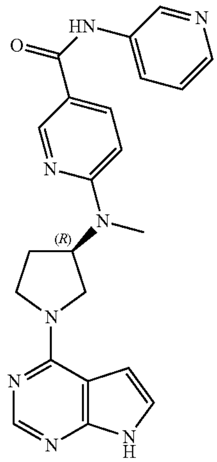 | 415 |
| 199 | 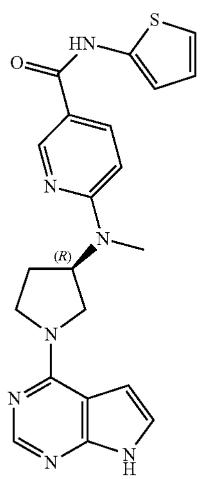 | 421 |
| 200 | 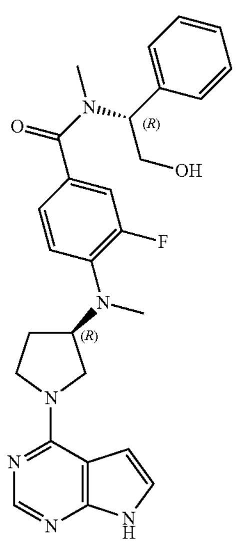 | 472 |
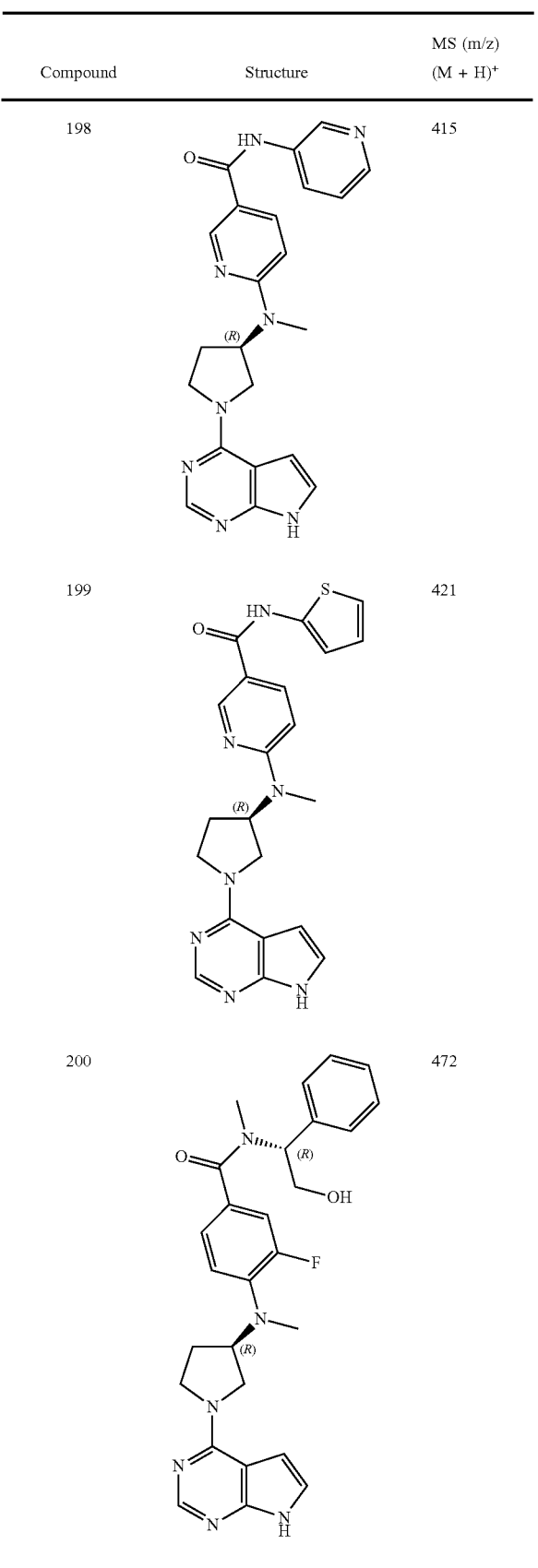
118
-continued
| Compound | Structure | MS (m/z) (M + H)+ |
|---|---|---|
| 201 | 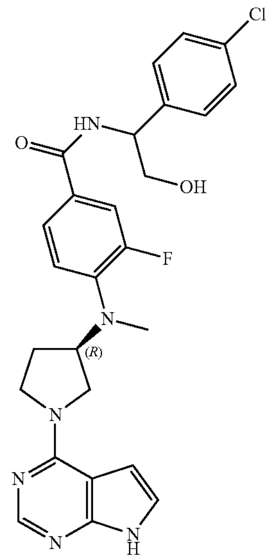 | 509 ($^{35}$Cl) 511 ($^{37}$Cl) |
| 202 | 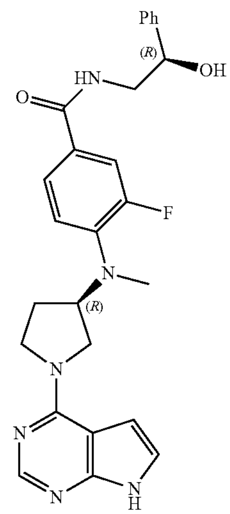 | 475 |
| 203 | 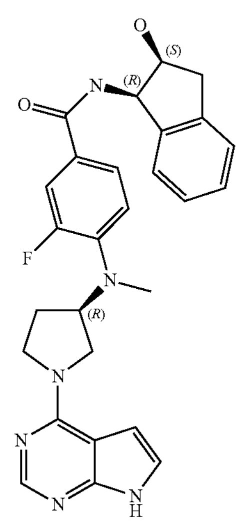 | 487 |
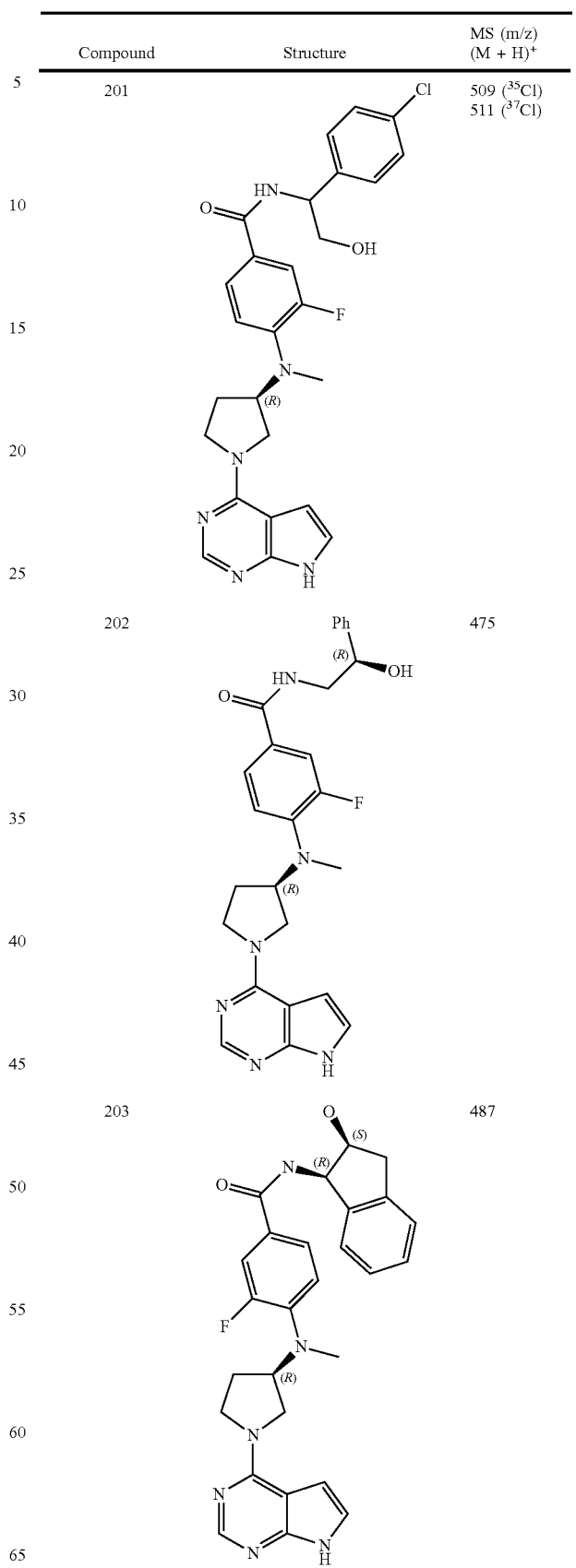

119
-continued

| Compound | Structure | MS (m/z) (M + H)+ |
|---|---|---|
| 204 | 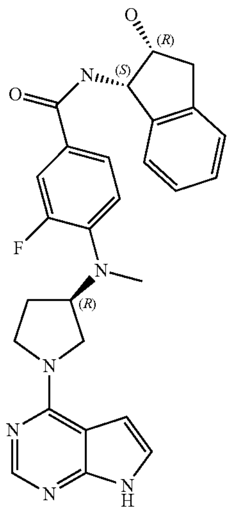 | 487 |
| 205 | 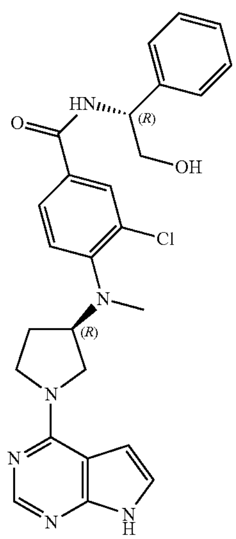 | 491 ($^{35}$Cl) 493 ($^{37}$Cl) |
| 206 | 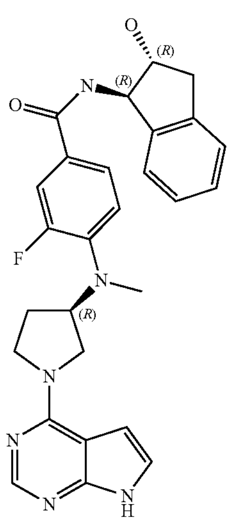 | 487 |

120
-continued

| Compound | Structure | MS (m/z) (M + H)+ |
|---|---|---|
| 207 | 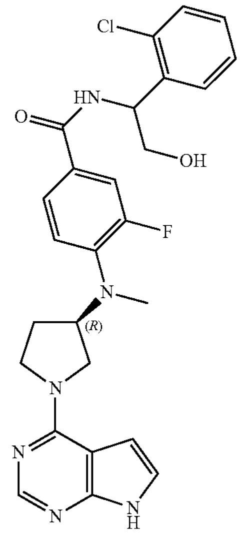 | 509 ($^{35}$Cl) 511 ($^{37}$Cl) |
| 208 | 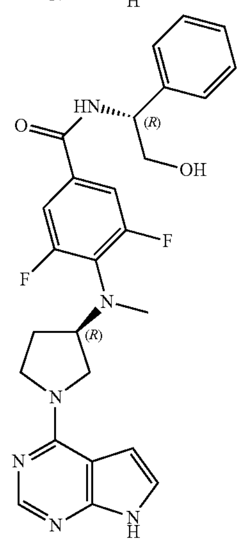 | 493 |
| 209 | 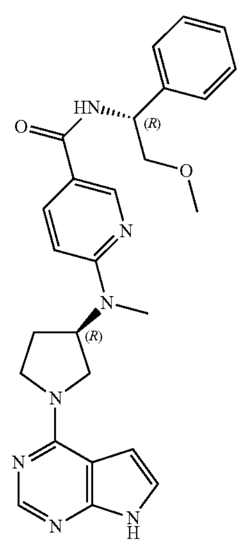 | 472 |

121

Compound 210

(R)—N-6-((1(7H-pyrrolo[2,3-d]pyrimidin-4-yl)pyrrolidin-3-yl)(methyl)(amino)pyridin-3-yl)ethanesulfonamfide

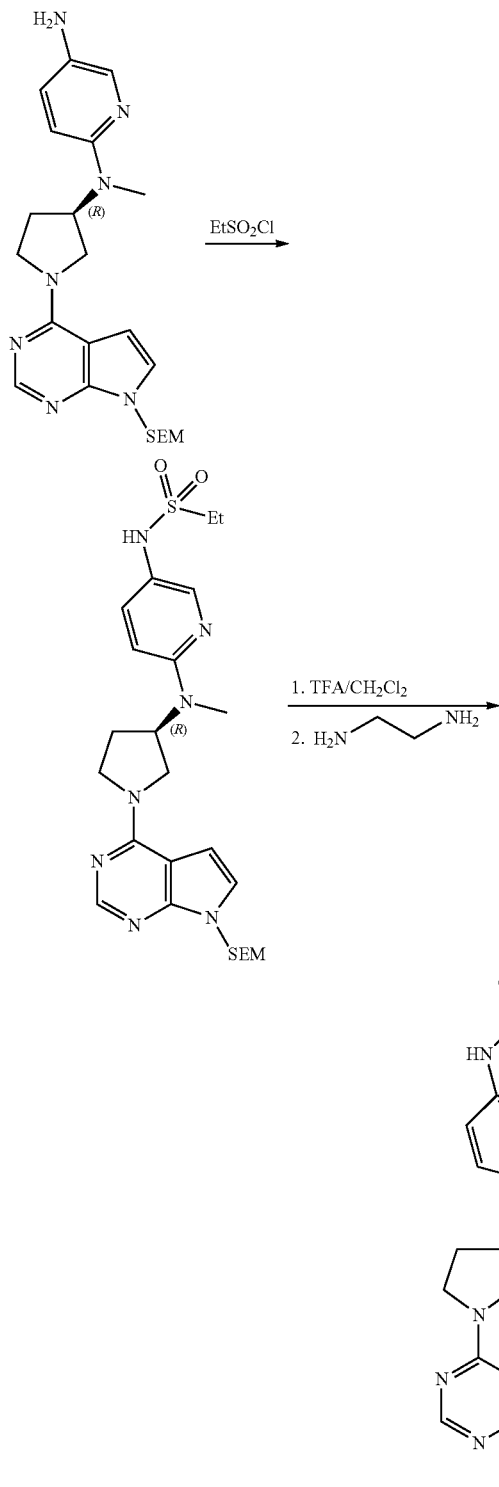

122

(A) (R)-Ethanesulfonic acid [6-(methyl-{1-[7-(2-trimethylsilanyl-ethoxymethyl)-7H-pyrrolo[2,3-d]pyrimidin-4-yl]-pyrrolidin-3-yl}-amino)-pyridin-3-yl]-amide To a solution of (R)—N²-methyl-N²-{1-[7-(2-trimethylsilanyl-ethoxymethyl)-7H-pyrrolo[2,3-d]pyrimidin-4-yl]-pyrrolidin-3-yl}-pyridine-2,5-diamine (0.25 mmol) in DCM (5 mL) were subsequently added ethanesulfonyl chloride (0.3 mmol) and Et₃N (0.3 mmol). The solution was stirred at the ambient temperature for 18 hours and then concentrated. The crude product was purified by preparative TLC to give the title compound in 42% yield.

(B) (R)—N-(6-((1-(7H-pyrrolo[2,3-d]pyrimidin-4-yl)pyrrolidin-3-yl)(methyl)amino)-pyridin-3-yl)ethanesulfonamide The tile compounds was prepared according to the procedure of Compound 23 (B) using (R)-ethanesulfonic acid [6-(methyl-({-[7-(2-trimethylsilanyl-ethoxymethyl)-7H-pyrrolo[2,3-d]pyrimidin-4-yl]-pyrrolidin-3-yl}-amino)-pyridin-3-yl]-amide. MS (m/z): 402 (M+H)⁺.

The following compounds were prepared according to the procedures of Compound 210 using the corresponding intermediates and reagents under appropriate conditions that could be recognized by one skilled in the art.

| Compound | Structure | MS (m/z) (M + H)⁺ |
|---|---|---|
| 211 | 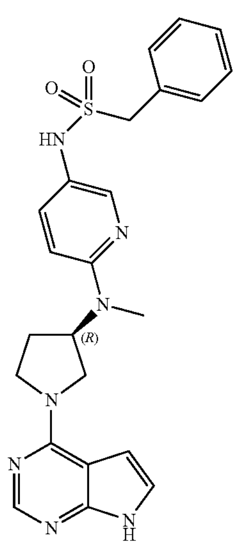 | 464 |

-continued

| Compound | Structure | MS (m/z) (M + H)+ |
|---|---|---|
| 212 | (4-fluorophenylsulfonamide on pyridine with (R)-N-methylpyrrolidinyl-pyrrolopyrimidine) | 468 |
| 213 | (2,5-difluorophenylsulfonamide analog) | 486 |
| 214 | (thiophene-2-sulfonamide analog) | 456 |

-continued

| Compound | Structure | MS (m/z) (M + H)+ |
|---|---|---|
| 215 | (pyridine-3-sulfonamide analog) | 451 |
| 216 | (cyclopropanesulfonamide analog) | 414 |
| 217 | (methanesulfonamide analog) | 388 |

TABLE-continued

| Compound | Structure | MS (m/z) (M + H)+ |
|---|---|---|
| 218 | 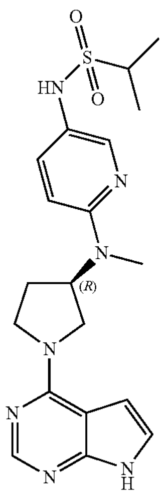 | 416 |
| 219 | 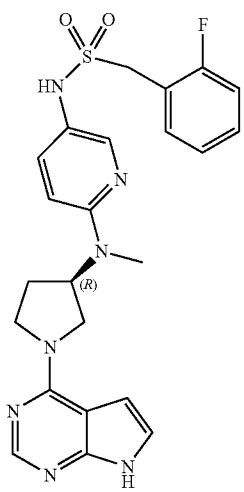 | 482 |
| 220 | 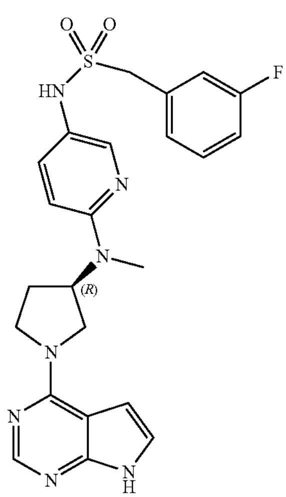 | 482 |
| 221 | | 482 |
| 222 | | 478 |
| 223 | | 498 |

| Compound | Structure | MS (m/z) (M + H)+ |
|---|---|---|
| 224 | 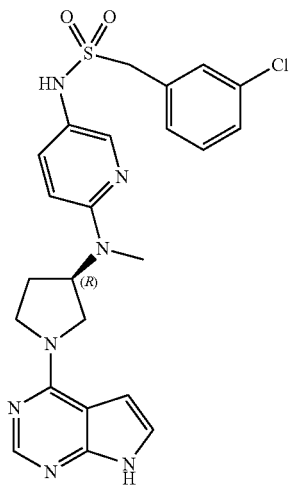 | 498 |
| 225 | | 498 |
| 226 | 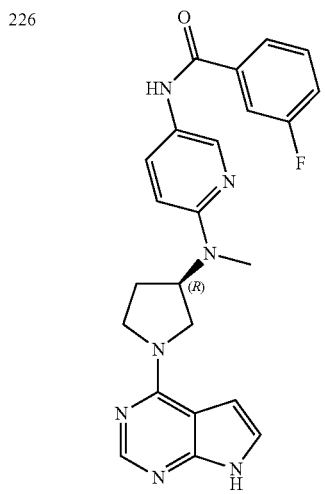 | 432 |
| Compound | Structure | MS (m/z) (M + H)+ |
|---|---|---|
| 227 | 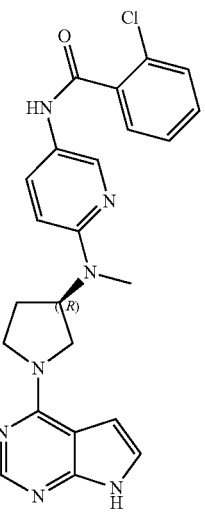 | 448 |
| 228 | 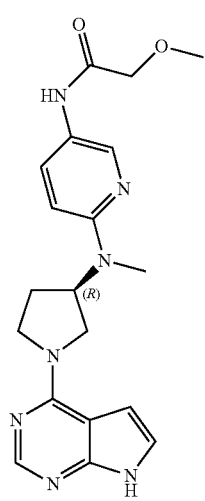 | 382 |
| 229 | 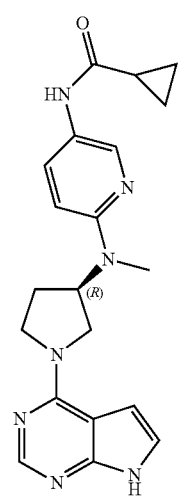 | 378 |

Compound 230

(R)—N⁵-(4-fluorobenzyl)-N²-(1-(7H-pyrrolo[2,3-d]pyrimidin-4-yl)pyrrolidin-3-yl)-N²-methylpyridine-2,5-diamine

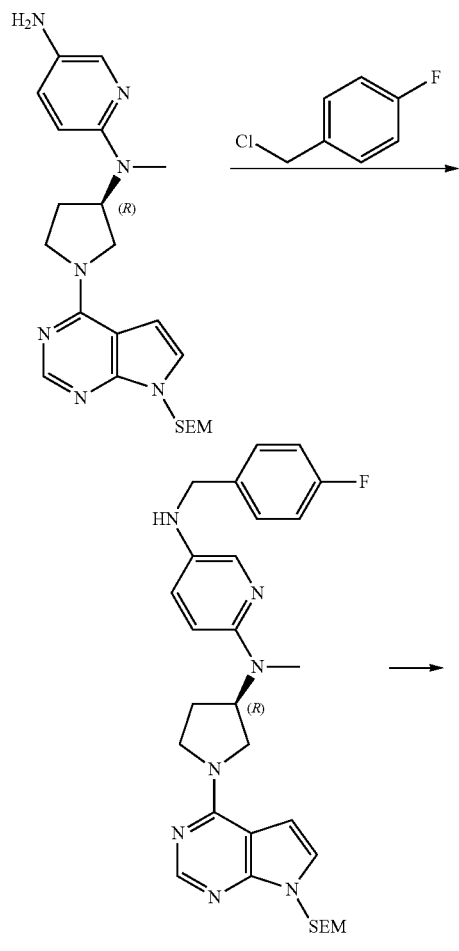

(A) (R)—N⁵-(4-fluorobenzyl)-N²-methyl-N²-(1-(7-((2-(trimethylsilyl)ethoxy)methyl)-7H-pyrrolo[2,3-d]pyrimidin-4-yl)pyrrolidin-3-yl)pyridine-2,5-diamine To a solution of (R)—N²-methyl-N²-(1-(7-((2-(trimethylsilyl)ethoxy)methyl)-7H-pyrrolo[2,3-d]pyrimidin-4-yl)pyrrolidin-3-yl)pyridine-2,5-diamine (0.20 mmol) in DMF (5 mL) were added K₂CO₃ (0.24 mmol) and 1-Chloromethyl-4-fluoro-benzene (0.24 mmol) at room temperature. The mixture was stirred at 80° C. for 18 hours, poured into water and extracted with EtOAc. The organic layer was washed with water and brine sequentially, then concentrated. The residue was purified by preparative TLC to give the title compound in 30% yield.

(B) (R)—N⁵-(4-fluorobenzyl)-N²-(1-(7H-pyrrolo[2,3-d]pyrimidin-4-yl)pyrrolidin-3-yl)-N²-methylpyridine-2,5-diamine The tile compounds was prepared according to the procedure of Compound 23 (B) using (R)—N⁵-(4-fluorobenzyl)-N²-methyl-N²-(1-(7-((2-(trimethylsilyl)ethoxy)methyl)-7H-pyrrolo[2,3-d]pyrimidin-4-yl)pyrrolidin-3-yl)pyridine-2,5-diamine. MS (m/z): 418 (M+H)⁺.

Compound 231

(R)-6-((1-(7H-pyrrolo[2,3-d]pyrimidin-4-yl)pyrrolidin-3-yl)(methyl)amino)-N,N-dimethylpyridine-3-sulfonamide

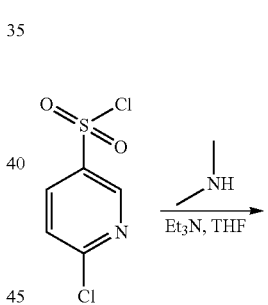

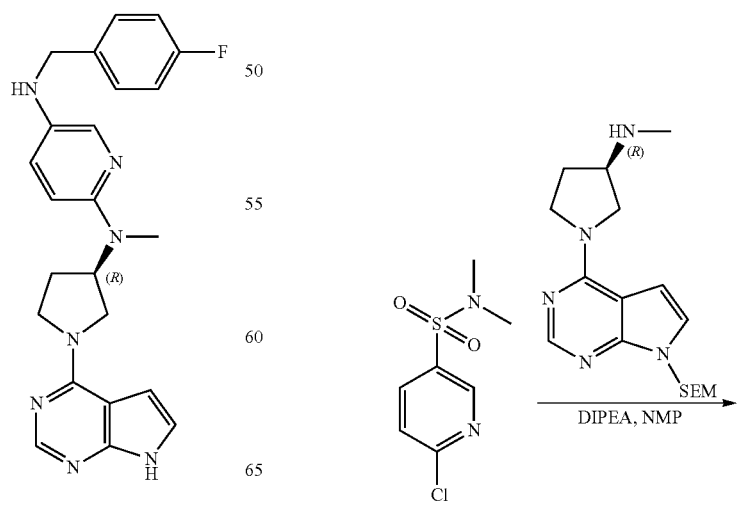

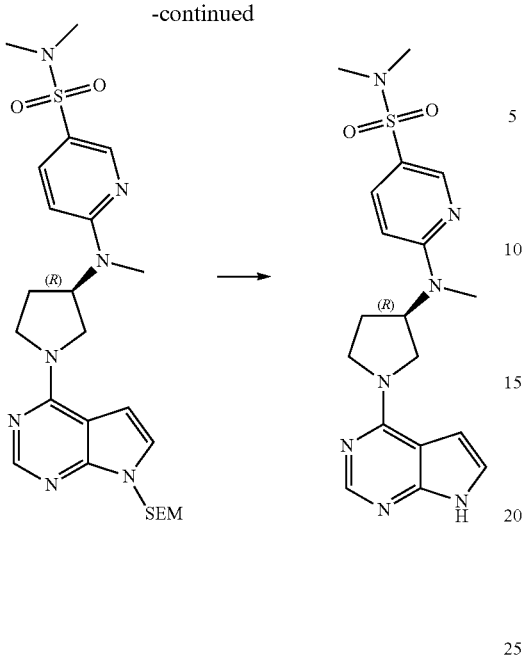

(A) 6-chloro-N,N-dimethylpyridine-3-sulfonamide

A solution of 6-chloropyridine-3-sulfonyl chloride (1 mmol), dimethylamine (2 mmol) and Et₃N (2 mmol) in THF (2 mL) was stirred at room temperature for 30 minutes. The mixture was diluted with EtOAc, washed with brine, dried, filtered, and concentrated to give the title compound in 95% yield.

(B) (R)—N,N-dimethyl-6-(methyl(1-(7-((2-(trimethylsilyl)ethoxy)methyl)-7H-pyrrolo[2,3-d]pyrimidin-4-yl)pyrrolidin-3-yl)amino)pyridine-3-sulfonamide To a solution of 6-chloro-N,N-dimethylpyridine-3-sulfonamide (1 mmol) and DIPEA (2.5 mmol) in NMP (2 mL) was added (R)—N-methyl-1-(7-((2-(trimethylsilyl) ethoxy) methyl)-7H-pyrrolo[2,3-d]pyrimidin-4-yl)pyrrolidin-3-amine (0.5 mmol). The reaction mixture was stirred at 200° C. for 60 minutes in microwave reactor. After cooling to room temperature, the mixture was diluted with EtOAc, washed with brine, dried, filtered, and concentrated. The residue was purified by chromatography with MeOH/H₂O to give the title compound in yellow in 8% yield.

(C) (R)-6-((1-(7H-pyrrolo[2,3-d]pyrimidin-4-yl) pyrrolidin-3-yl)(methyl)amino)-N,N-dimethylpyridine-3-sulfonamide The tile compounds was prepared according to the procedure of Compound 23 (B) using (R)—N,N-dimethyl-6-(methyl(1-(7-((2-(trimethylsilyl)ethoxy)methyl)-7H-pyrrolo[2,3-d]pyrimidin-4-yl)pyrrolidin-3-yl)amino)pyridine-3-sulfonamide. MS (m/z): 402 (M+H)⁺.

The following compounds were prepared according to the procedures of Compound 231 using the corresponding intermediates and reagents under appropriate conditions that could be recognized by one skilled in the art.

| Compound | Structure | MS (m/z) (M + H)⁺ |
|---|---|---|
| 232 | 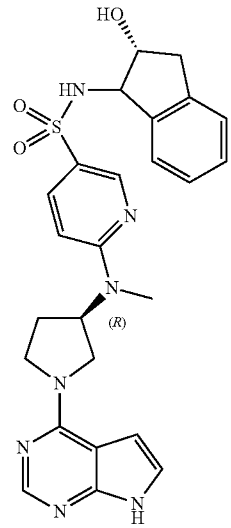 | 506 |
| 233 | 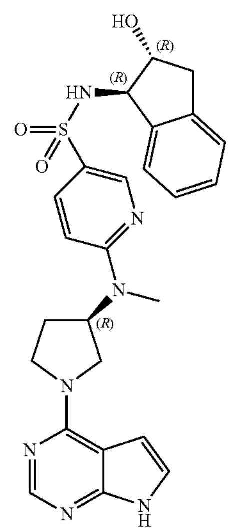 | 506 |
| 234 | 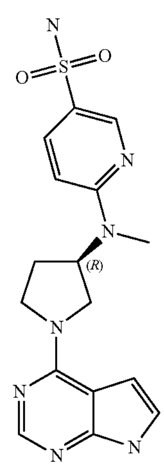 | 374 |

-continued

| Compound | Structure | MS (m/z) (M + H)+ |
|---|---|---|
| 235 | 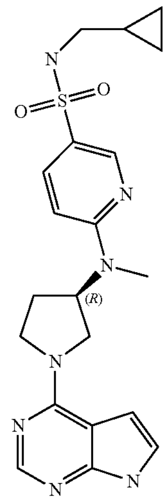 | 428 |
| 236 | 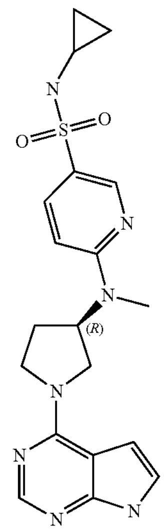 | 414 |
| 237 | 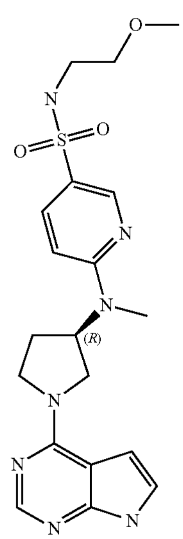 | 432 |

-continued

| Compound | Structure | MS (m/z) (M + H)+ |
|---|---|---|
| 238 | 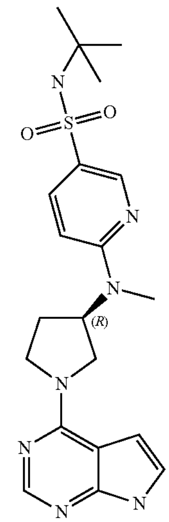 | 430 |
| 239 | 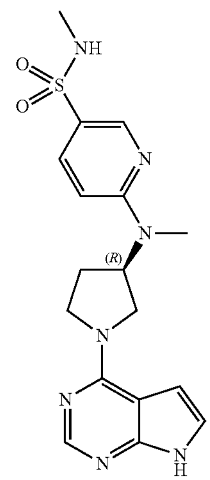 | 388 |
| 240 | 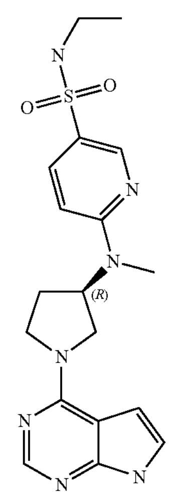 | 402 |

-continued
| Compound | Structure | MS (m/z) (M + H)+ |
|---|---|---|
| 241 | 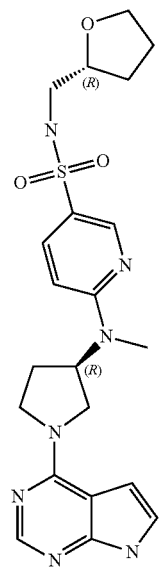 | 458 |
| 242 | 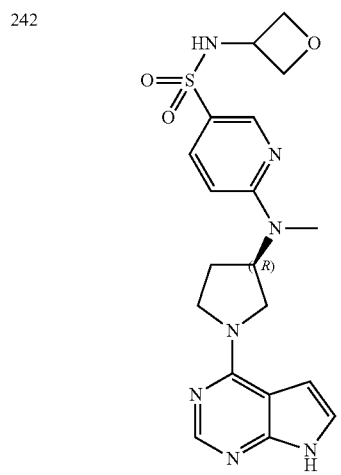 | 430 |
| 243 | 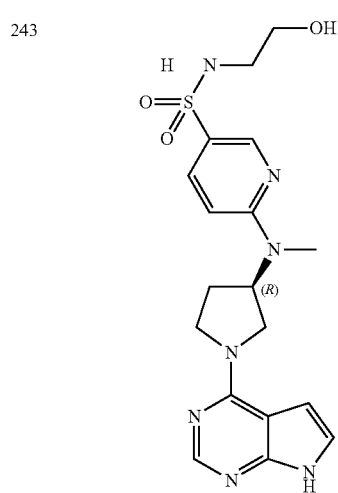 | 418 |
-continued
| Compound | Structure | MS (m/z) (M + H)+ |
|---|---|---|
| 244 | 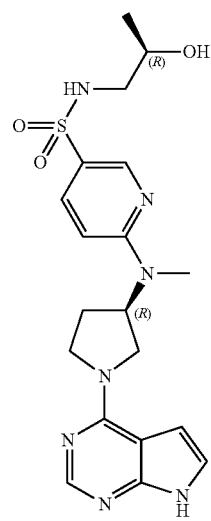 | 432 |
| 245 | 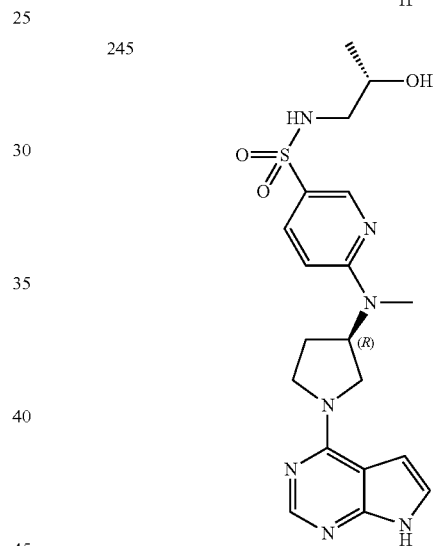 | 432 |
| 246 | 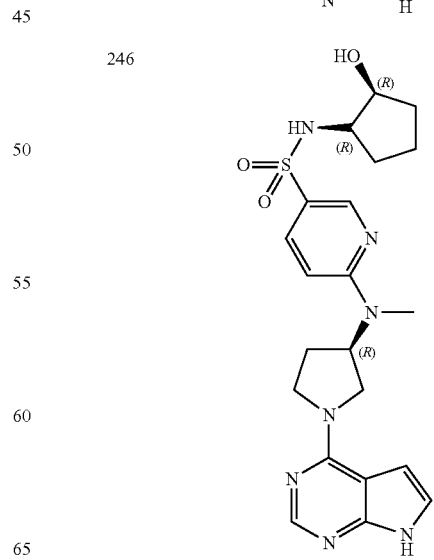 | 458 |

137
-continued
| Compound | Structure | MS (m/z) (M + H)+ |
|---|---|---|
| 247 | 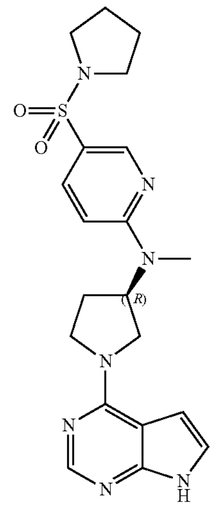 | 428 |
| 248 | 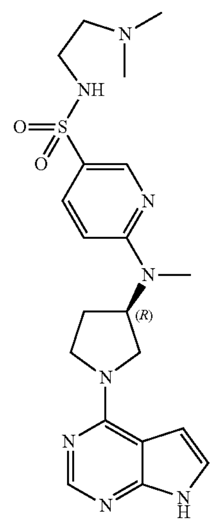 | 445 |
| 249 | 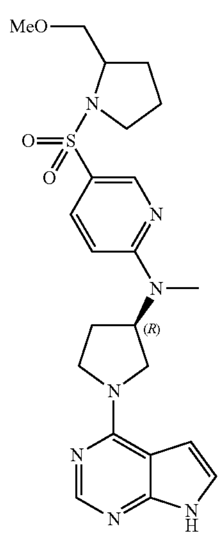 | 472 |
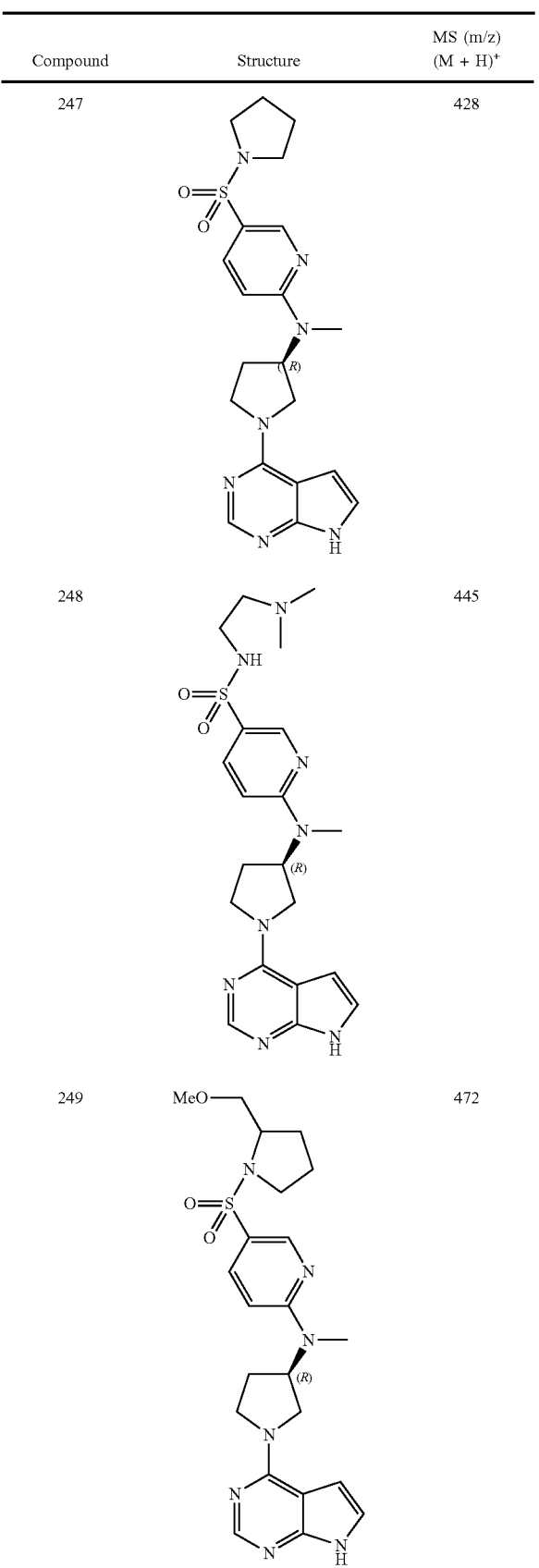
138
-continued
| Compound | Structure | MS (m/z) (M + H)+ |
|---|---|---|
| 250 | 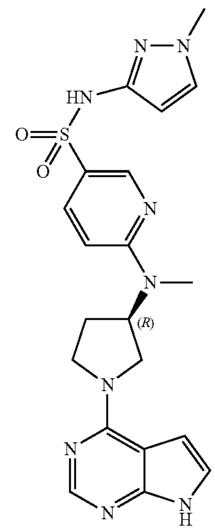 | 454 |
| 251 | 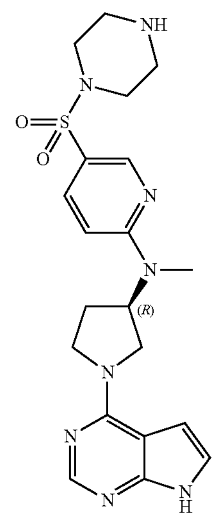 | 443 |
| 252 | 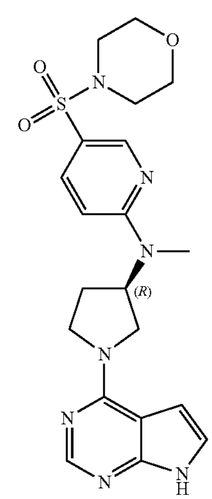 | 444 |
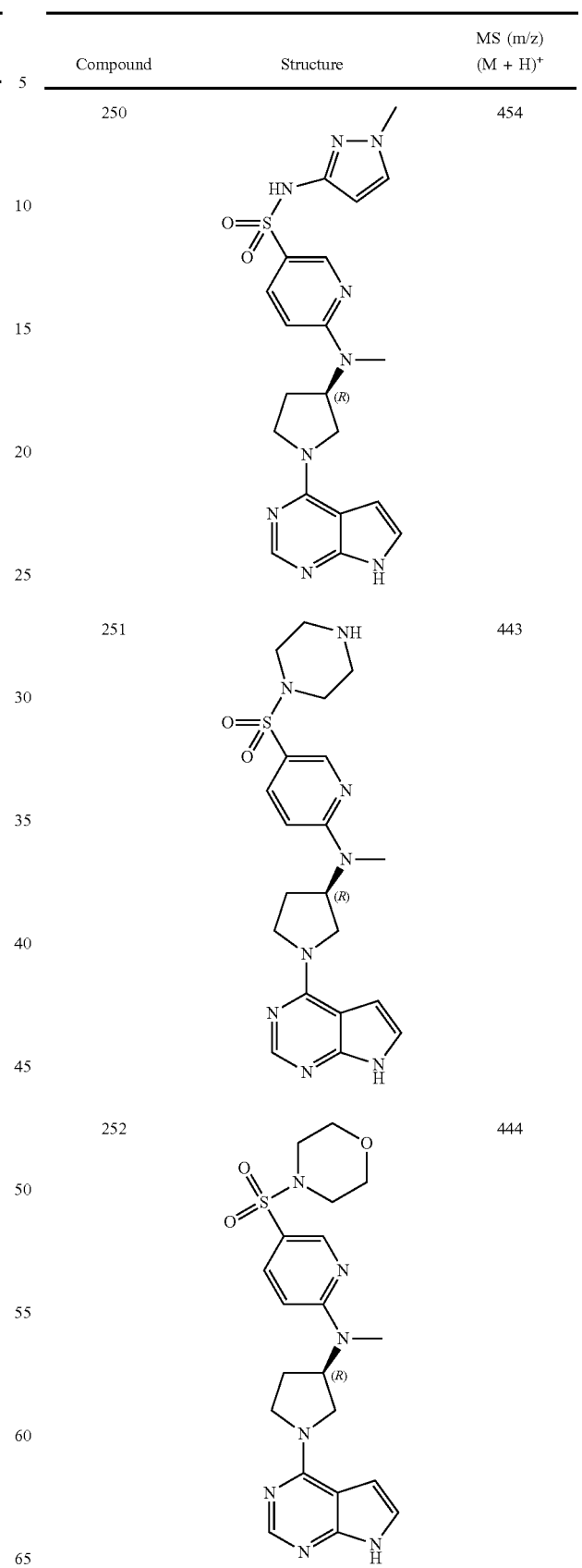

-continued

| Compound | Structure | MS (m/z) (M + H)+ |
|---|---|---|
| 253 | 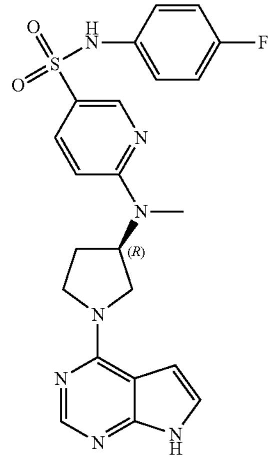 | 468 |
| 254 | 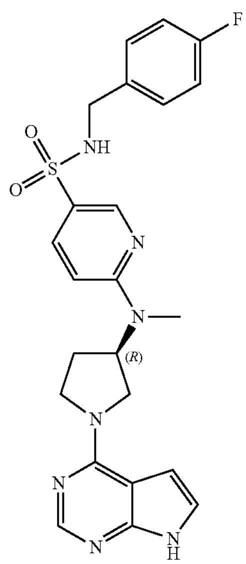 | 482 |
| 255 | 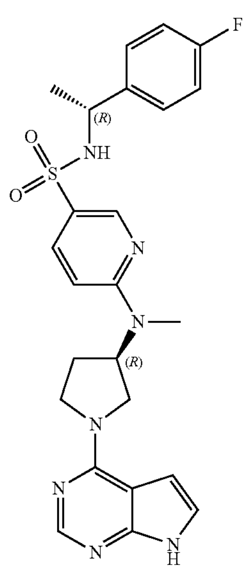 | 496 |
| 256 | | 496 |
| 257 | | 458 |
| 258 | | 440 |

-continued

| Compound | Structure | MS (m/z) (M + H)+ |
|---|---|---|
| 259 | 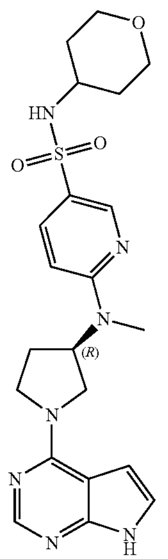 | 458 |

Compound 260

(R)-6-((1-7H-pyrrolo[2,3-d]pyrimidin-4-yl)pyrrolidin-3-yl)(methyl)amino)-2-hydroxynicotinonitrile

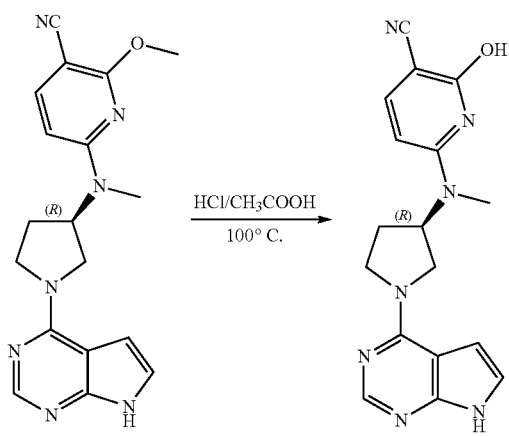

(R)-6-((1-(7H-pyrrolo[2,3-d]pyrimidin-4-yl)pyrrolidin-3-yl)(methyl)amino)-2-methoxynicotinonitrile (0.43 mmol) was dissolved in the mixture of HCl (concentrated, 0.4 mL) and TFA (2.0 mL). The mixture was then refluxed for 7 hours, concentrated under reduced pressure, and purified by preparative HPLC to give the title compound. MS (m/z): 336 (M+H)+.

Example 2

Enzymatic Assay

JAK1/2/3 kinase assay are performed in vitro using Kit-Tyr 6 Peptide (Invitrogen, Cat. No. PV4122). TYK2 kinase assay are performed in vitro using Z'-LYTE™ Kinase Assay Kit-Tyr 3 Peptide (Invitrogen, Cat. No. PV3192). Recombinant human JAK1/2/3 or TYK2 catalytic domains are from Invitrogen (Cat No. PV4774/PV4210/PV3855/PV4790); All reactions (20 μL) are started by adding 2.5 μL of the testing compound in 4% DMSO solution, 5 μL of Kinase/Peptide substrate Mixture (3.2, 0.04, 0.2 or 8 g/mL for Recombinant human JAK1/2/3 catalytic domains, 4 μM for Z-LYTE™ Tyr 6 peptide or Z-LYTE™ Tyr 3 peptide) or Phospho-Peptide solution (Invitrogen, Cat. No. PV3192, diluted with 1.33× Kinase Buffer), 2.5 μL ATP Solution (300/100/40/100 μM, JAK1/JAK2/JAK3/TYK2) or 1.33× Kinase Buffer (Invitrogen, Cat. No. PV3189, 5× diluted with distilled water). The 384-well assay plate (Corning, Cat. No. 3575) is mixed and incubated at room temperature for 1 hour. 5 μL of the Development Solution (Dilute Development Reagent A (Cat. No. PV3297) is diluted to 1/64 with Development Buffer (Cat. No. PV3127) for JAK1, JAK2 and JAK3 assay; Development Reagent A (Cat. No. PV3297) is diluted to 1/2048 with Development Buffer (Cat. No. PV3127) for TYK2 assay. The diluted Development Solution is then added to each well, mixed and incubated at room temperature for another 1 hour. The kinase reaction is then stopped by adding 5 μL of the Stop Reagent (Invitrogen, Cat. No. PV3094), and the plate is read with Wallac 1420 VICTOR$^3$ Multilabel Counter (PerkinElmer®) at 445 nm and 520 nm fluorescence. All compounds are initially tested at 8 different concentrations (1 μM down to 0.0003 μM) using a 1:3 serial dilution scheme.

Most of the compounds disclosed herein inhibited at least one kinase chosen from JAK1, JAK2, JAK3 and TYK2 with $IC_{50}$<1.0 uM.

Example 3

Cellular Assays

For the determination of IL-6-induced STAT3 phosphorylation, HepG2 cells (SIBS) are seeded in 96 well plates at 5.4×10 cells per well in Serum Free DMEM media overnight and incubated in the presence or absence of various concentrations of diluted compound for 30 min at 37° C., 5% CO2. Cells were stimulated by adding 10 ng/ml human recombinant IL-6 to each well for 15 minutes at 37° C., 5% CO2. Cells are then fixed in 2% paraformaldehyde for 45 minutes at room temperature and incubated in ice-cold methanol for 30 minutes. After washing in PBS, cells are incubated with rabbit anti-phospho-STAT3 (Y705) (Cell Signaling Technologies, 1:1000 in antibody dilution solution) primary antibody overnight at 4° C. Goat anti-rabbit IgG Alexa 488 (Invitrogen, 1:1,000 dilution in PBS) secondary antibody is added for 90 minutes prior to PBS washes. Cells are counted following incubation in a 7.5 uM propidium iodide, 100 μg/ml RNaseA, PBS solution for 60 minutes in the dark. Plates are read on an Acumen X3 instrument (TPP Labtech).

For the determination of IL-3-induced STAT5 phosphorylation, TF-1 cells (ATCC) are plated in 96 well plates at 1×10$^4$ cells per well in 10% FBS RPMI-1640 media at 37° C., 5% CO2 for 3 hours. Cells were incubated in the presence or absence of various concentrations of diluted compound for 30 min at 37° C., 5% CO2. Cells were stimulated by adding 10 ng/ml human recombinant IL-3 to each well for 30 minutes at 37° C., 5% CO2. Cells are then fixed in 2% paraformaldehyde for 45 minutes at room temperature and incubated in ice-cold methanol for 30 minutes. After washing in PBS, cells are incubated with rabbit anti-phospho-STAT5 (Y694) (Cell Signaling Technologies, 1:1000 in antibody dilution solution) primary antibody overnight at 4° C. Goat anti-rabbit IgG Alexa 488

(Invitrogen, 1:1,000 dilution in PBS) secondary antibody is added for 90 minutes prior to PBS washes. Cells are counted following incubation in a 7.5 uM propidium iodide, 100 g/ml RNaseA, PBS solution for 60 minutes in the dark. Plates are read on an Acumen X3 instrument (TPP Labtech).

For the determination of IL-4-induced STAT6 phosphorylation, Ramos cells (ATCC) are plated in 96 well plates at $1.0 \times 10^4$ cells per well 10% FBS RPMI-1640 and incubated at 37° C., 5% CO2 for 3 hours. Cells were incubated with compounds for 30 minutes prior to stimulation with interleukin-4 (10 ng/ml final) for an additional 30 minutes. Cells are then fixed in 2% paraformaldehyde for 45 minutes and incubated in ice-cold methanol for 30 minutes. After washing in PBS, cells are incubated with rabbit anti-phospho-STAT6 (Y641) (Cell Signaling Technologies, 1:1000 in antibody dilution solution) primary antibody overnight at 4° C. Goat anti-rabbit IgG Alexa 488 (Invitrogen, 1:1,000 dilution in PBS) secondary antibody is added for 90 minutes prior to PBS washes. Cells are counted following incubation in a 7.5 uM propidium iodide, 100 g/ml RNaseA, PBS solution for 60 minutes in the dark. Plates are read on an Acumen X3 instrument (TPP Labtech).

Percent inhibition is calculated using the following formula:

Inhibition (%)=100−((inhibitor treatment−cell)/(stimulator−cell))×100 where: Inhibitor treatment represents cell activation percentage of wells treated by both compound and stimulator (IL-6, IL-3 or IL-4); Cell represents the cell activation percentage of wells treated by neither compound nor stimulator (IL-6, IL-3 or IL-4). Stimulator represents the cell activation percentage of wells treated by stimulator (IL-6, IL-3 or IL-4) only.

Most of the compounds disclosed herein inhibited at least one kinase chosen from JAK1, JAK2, JAK3 and TYK2 in the cellular assays with $IC_{50}$<10.0 uM.

For example, in above JAK1 kinase assay, the present compounds have the following inhibition percentage at 0.3 uM concentration (IR %):

IR % values for compounds 1, 3, 6, 7, 10, 12, 14, 15, 16, 17, 20, 21, 24, 27, 28, 29, 30, 31, 33, 38, 40, 41, 42, 45, 46, 47, 48, 49, 52, 53, 55, 56, 59, 60, 61, 62, 63, 64, 67, 68, 70, 71, 72, 73, 74, 77, 79, 80, 81, 83, 84, 85, 86, 87, 89, 90, 91, 92, 93, 94, 95, 96, 97, 98, 99, 101, 102, 103, 104, 105, 106, 107, 108, 111, 112, 114, 115, 117, 119, 121, 122, 123, 124, 126, 127, 129, 131, 132, 133, 134, 136, 138, 144, 147, 150, 152, 153, 154, 155, 156, 157, 158, 159, 161, 162, 163, 164, 167, 168, 170, 171, 174, 176, 177, 178, 179, 180, 182, 183, 184, 185, 186, 187, 190, 191, 192, 195, 197, 199, 201, 202, 204, 205, 206, 207, 208, 209, 210, 212, 214, 218, 219, 220, 222, 223, 224, 225, 226, 227, 229, 230, 234, 235, 236, 237, 238, 239, 240, 242, 243, 244, 245, 246, 247, 248, 249, 251, 252, 253, 254, 255, 256, 259, 260, 261, 262, are in the range from 50% to less than 100%;

IR % values for compounds 4, 5, 8, 9, 11, 13, 19, 35, 43, 44, 39, 54, 57, 58, 65, 66, 75, 76, 78, 88, 100, 109, 110, 113, 116, 118, 120, 130, 135, 141, 142, 146, 148, 151, 160, 165, 166, 169, 172, 173, 175, 188, 189, 193, 194, 196, 198, 200, 203, 213, 221, 228, 232, 250, 257, are in the range from 20% to less than 50%.

In addition, in above JAK1 kinase assay, $IC_{50}$ values for compounds 1, 16, 21, 30, 33, 36, 37, 42, 67, 68, 77, 86, 104, 105, 106, 119, 121, 122, 123, 124, 125, 127, 128, 144, 154, 155, 161, 202, 214, 215, 217, 218, 219, 233, 234, 236, 237, 238, 239, 241, 242, 243, 245, 246, 247, 251, 252, 253, 254, 259, are in the range from 0.001 uM to less than 0.1 uM.

In above JAK2 kinase assay, $IC_{50}$ values for compounds 1, 40, 41, 42, 46, 47, 48, 60, 61, 62, 63, 64, 66, 67, 71, 73, 80, 81, 84, 86, 87, 91, 92, 93, 94, 98, 99, 102, 103, 104, 111, 114, 121, 122, 123, 124, 125, 126, 128, 129, 131, 134, 153, 155, 156, 157, 159, 161, 162, 163, 164, 168, 171, 174, 176, 179, 182, 184, 185, 187, 190, 192, 201, 202, 204, 208, 209, 210, 212, 236, 241, 242, are in the range from 0.001 uM to less than 0.1 uM;

$IC_{50}$ values for compounds 3, 6, 7, 10, 12, 16, 17, 30, 49, 52, 53, 55, 56, 57, 58, 68, 70, 72, 77, 79, 83, 85, 89, 90, 96, 97, 101, 107, 108, 115, 130, 136, 147, 154, 158, 160, 167, 170, 178, 195, 207, 217, 218, 239, 243, 252, 259, are in the range from 0.1 uM to less than 1 uM.

In above JAK3 kinase assay, $IC_{50}$ values of compounds 42, 63, 66, 67, 121, 126, 129, 134, 162, 182, 208, 209, 236, are in the range from 0.001 uM to less than 0.1 uM;

$IC_{50}$ values for compounds 1, 17, 25, 40, 41, 48, 60, 62, 64, 70, 71, 73, 77, 79, 80, 81, 84, 86, 87, 91, 92, 93, 94, 96, 97, 98, 99, 102, 103, 104, 107, 111, 114, 131, 153, 156, 159, 163, 164, 168, 171, 174, 179, 184, 187, 190, 201, 202, 210, are in the range from 0.1 uM to less than 1 uM.

The experimental data of some compounds tested in Examples 2 and 3 are set forth in the following table.

| Compound No. | JAK1 (enzyme, $IC_{50}$, μM) | JAK2 (enzyme, $IC_{50}$, μM) | JAK3 (enzyme, $IC_{50}$, μM) | pSTAT3 ($IC_{50}$, μM) | pSTAT5 ($IC_{50}$, μM) | pSTAT6 ($IC_{50}$, μM) |
|---|---|---|---|---|---|---|
| 47 | 0.119 | 0.098 | 0.157 | 0.824 | 1.486 | 1.149 |
| 105 | 0.0140 | 0.0487 | 0.3594 | 0.009 | 1.680 | NT |
| 142 | 0.0094 | 0.055 | 0.497 | 0.065 | 3.066 | 0.3364 |
| 199 | 0.014 | 0.075 | 0.522 | 0.050 | 7.549 | NT |
| 206 | 0.002 | 0.0005 | 0.047 | 0.0239 | 0.6928 | 0.180 |
| 234 | 0.0051 | 0.0411 | 0.0863 | 0.337 | 0.857 | 0.385 |

What is claimed is:

1. A compound of formula (1):

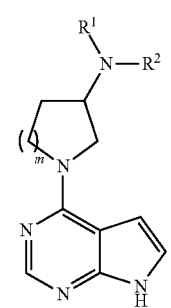

wherein

R¹ is chosen from hydrogen, alkyl, cycloalkyl and heterocycle, each of the said alkyl, cycloalkyl, and heterocycle, in R¹ is optionally substituted with one or more groups chosen from optionally substituted lower alkyl, optionally substituted aryl, optionally substituted alkenyl, optionally substituted alkynyl, optionally substituted cycloalkyl, —C(O)R$^a$, —C(O)OR$^b$, —CN, —C(O)NR$^c$R$^d$, halo, optionally substituted haloalkyl, optionally substituted heterocycle, optionally substituted heteroaryl, —NR$^c$R$^d$, —NR$^e$C(O)R$^a$, —NR$^e$C(O)OR$^b$, —NR$^e$C(O)NR$^c$R$^d$, —NR$^e$S(O)$_n$R$^f$, —NR$^e$S(O)$_n$NR$^c$R$^d$, —NO$_2$, —OR$^b$, —S(O)$_n$R$^f$, and —S(O)$^n$NR$^c$R$^d$;

R² is chosen from aryl, heterocycle, heteroaryl, —S(O)$_n$R$^f$, and —S(O)$_n$NR$^c$R$^d$, wherein said aryl or heteroaryl is selected from the group consisting of

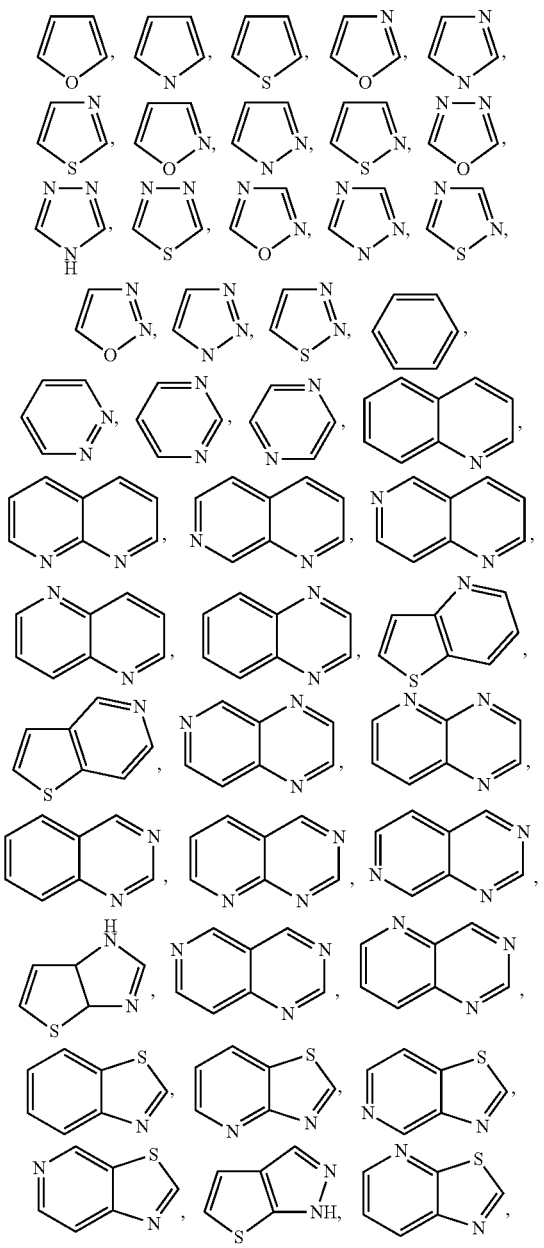

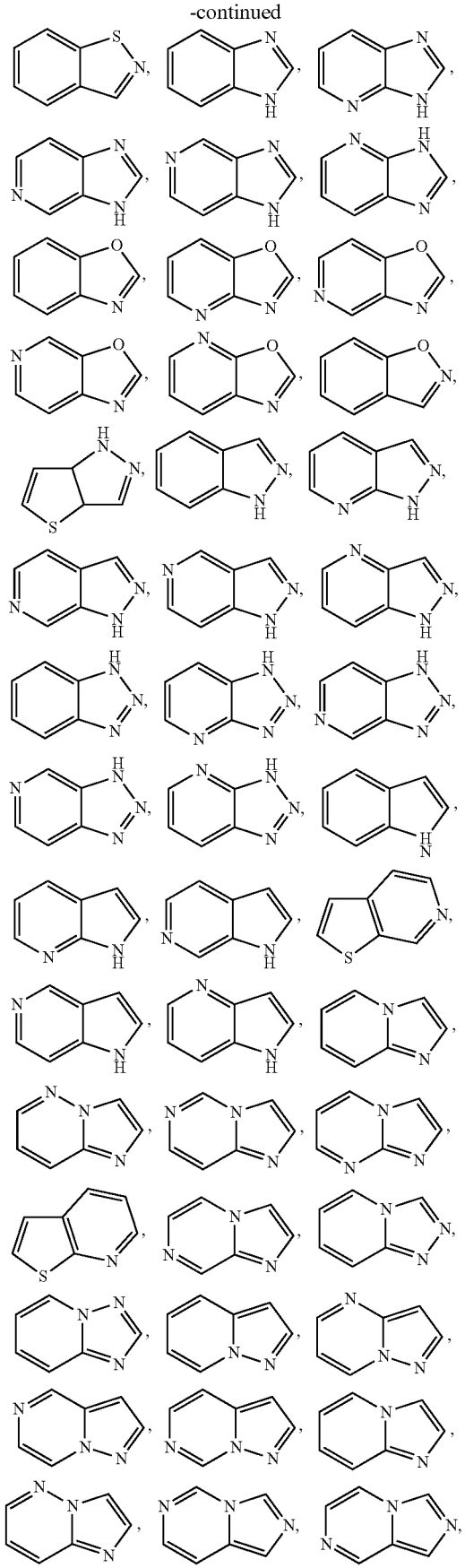

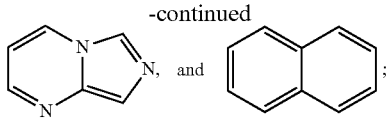

and each of the above said aryl, heterocycle, heteroaryl in $R^2$ is optionally substituted with one or more groups chosen from optionally substituted alkyl, optionally substituted aryl, optionally substituted alkenyl, optionally substituted alkynyl, optionally substituted cycloalkyl, C(O)$R^a$, —C(O)O$R^b$, —CN, —C(O)N$R^c R^d$, halo, optionally substituted haloalkyl, optionally substituted heterocycle, optionally substituted heteroaryl, —N$R^c R^d$, —N$R^e$C(O)$R^a$, —N$R^e$C(O)O$R^b$, —N$R^e$C(O)N$R^c R^d$, —N$R^e$S(O)$_n R^f$, —N$R^e$S(O)$_n$N$R^c R^d$, —NO$_2$, —O$R^b$, —S(O)$_n R^f$, and —S(O)$_n$N$R^c R^d$;

m is 1 and n is independently chosen from 0, 1, and 2;

for each occurrence, $R^a$, $R^b$, $R^c$, $R^d$, $R^e$ and $R^f$ are each independently chosen from hydrogen, optionally substituted alkyl, optionally substituted alkenyl, optionally substituted alkynyl, optionally substituted cycloalkyl, optionally substituted aryl, optionally substituted haloalkyl, optionally substituted heteroaryl and optionally substituted heterocycle, or $R^e$ and $R^d$, with the nitrogen to which they are attached, combine to form a heterocycle ring, which is optionally substituted with one or more groups chosen from halo, lower alkyl, hydroxy, and lower alkoxy, wherein the heterocycle ring further optionally comprises one or two additional heteroatoms chosen from N, O and S, wherein each optionally substituted group above can be unsubstituted or independently substituted with at least one substituent independently chosen from $C_1$-$C_4$ alkyl, cycloalkyl, aryl, heterocycle, heteroaryl, aryl-$C_1$-$C_4$ alkyl, heteroaryl-$C_1$-$C_4$ alkyl-, $C_1$-$C_4$ haloalkyl-, —O$C_1$-$C_4$ alkyl, —O$C_1$-$C_4$ alkylphenyl, —$C_1$-$C_4$ alkylOH, —$C_1$-$C_4$ alkyl-O—$C_1$-$C_4$ alkyl, —O$C_1$-$C_4$ haloalkyl, halo, —OH, —NH$_2$, —$C_1$-$C_4$ alkyl-NH$_2$, —N($C_1$-$C_4$ alkyl)($C_1$-$C_4$ alkyl), —NH ($C_1$-$C_4$ alkyl), —N($C_1$-$C_4$ alkyl)($C_1$-$C_4$ alkylphenyl), —NH ($C_1$-$C_4$ alkylphenyl), cyano, nitro, oxo, —CO$_2$H, —C(O) O$C_1$-$C_4$ alkyl, —CON($C_1$-$C_4$ alkyl)($C_1$-$C_4$ alkyl), —CONH ($C_1$-$C_4$ alkyl), —CONH$_2$, —NHC(O)($C_1$-$C_4$ alkyl), —NHC (O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ haloalkyl, —OC(O)($C_1$-$C_4$ alkyl), —SO$_2$($C_1$-$C_4$ alkyl), —SO$_2$NH$_2$, —SO$_2$(phenyl), —SO$_2$($C_1$-$C_4$ haloalkyl), —SO$_2$NH$_2$, —SO$_2$NH($C_1$-$C_4$ alkyl), —SO$_2$NH(phenyl), —NHSO$_2$($C_1$-$C_4$ alkyl), —NHSO$_2$(phenyl), and —NHSO$_2$($C_1$-$C_4$ haloalkyl), in which each of phenyl, aryl, heterocycle, and heteroaryl is optionally substituted by one or more groups chosen from halo, cycloalkyl, heterocycle, $C_1$-$C_4$ alkyl, $C_1$-$C_4$ haloalkyl-, —O$C_1$-$C_4$ alkyl, $C_1$-$C_4$ alkyl-OH, —$C_1$-$C_4$ alkyl-O—$C_1$-$C_4$ alkyl, —O$C_1$-$C_4$ haloalkyl, cyano, nitro, —NH$_2$, —CO$_2$H, —C(O)O$C_1$-$C_4$ alkyl, —CON($C_1$-$C_4$ alkyl)($C_1$-$C_4$ alkyl), —CONH($C_1$-$C_4$ alkyl), —CONH$_2$, —NHC(O)($C_1$-$C_4$ alkyl), —N($C_1$-$C_4$ alkyl)C(O)($C_1$-$C_4$ alkyl), —SO$_2$($C_1$-$C_4$ alkyl), —SO$_2$(phenyl), —SO$_2$($C_1$-$C_4$ haloalkyl), —SO$_2$NH$_2$, SO$_2$NH($C_1$-$C_4$ alkyl), —SO$_2$NH (phenyl), —NHSO$_2$($C_1$-$C_4$ alkyl), —NHSO$_2$(phenyl), and —NHSO$_2$($C_1$-$C_4$ haloalkyl);

or at least one pharmaceutically acceptable salt thereof.

2. The compound of claim 1, and/or at least one pharmaceutically acceptable salt thereof, wherein $R^1$ is chosen from alkyl and cycloalkyl, each of which is optionally substituted with one or more groups chosen from optionally substituted lower alkyl, optionally substituted aryl, optionally substituted alkenyl, optionally substituted alkynyl, optionally substituted cycloalkyl, —C(O)$R^a$, —C(O)O$R^b$, —CN, —C(O) N$R^c R^d$, halo, optionally substituted haloalkyl, optionally substituted heterocycle, optionally substituted heteroaryl, —N$R^c R^d$, —N$R^e$C(O)$R^a$, —N$R^e$C(O)O$R^b$, —N$R^e$C(O) N$R^c R^d$, —N$R^e$S(O)$_n R^f$, —N$R^e$S(O)$_n$N$R^c R^d$, —NO$_2$, —O$R^b$, —S(O)$_n R^f$, and —S(O)$_n$N$R^c R^d$.

3. The compound of claim 1, and/or at least one pharmaceutically acceptable salt thereof, wherein $R^1$ is alkyl optionally substituted by one or more groups chosen from alkenyl, alkynyl, and cycloalkyl.

4. The compound of claim 1, and/or at least one pharmaceutically acceptable salt thereof, wherein $R^1$ is cycloalkyl.

5. The compound of claim 1, and/or at least one pharmaceutically acceptable salt thereof, wherein $R^2$ is aryl or heteroaryl, each of which is optionally substituted with one or more groups chosen from optionally substituted lower alkyl, optionally substituted aryl, optionally substituted alkenyl, optionally substituted alkynyl, optionally substituted cycloalkyl, —C(O)$R^a$, —C(O)O$R^b$, —CN, —C(O)N$R^c R^d$, halo, optionally substituted haloalkyl, optionally substituted heterocycle, optionally substituted heteroaryl, —N$R^c R^d$, —N$R^e$C(O)$R^a$, —N$R^e$C(O)O$R^b$, —N$R^e$C(O)N$R^c R^d$, —N$R^e$S(O)$_n R^f$, —N$R^e$S(O)$_n$N$R^c R^d$, —NO$_2$, O$R^b$, —S(O)$_n R^f$, and —S(O)$_n$N$R^c R^d$.

6. The compound of claim 1, and/or at least one pharmaceutically acceptable salt thereof, wherein $R^2$ is —S(O)$_n$N$R^c R^d$, $R^a$, $R^c$, and $R^d$ are each independently chosen from hydrogen, optionally substituted alkyl, optionally substituted alkenyl, optionally substituted alkynyl, optionally substituted cycloalkyl, optionally substituted aryl, optionally substituted haloalkyl, optionally substituted heteroaryl and optionally substituted heterocycle, or $R^c$ and $R^d$, with the nitrogen to which they are attached, combine to form a heterocycle ring, which is optionally substituted with one or more groups chosen from halo, lower alkyl, hydroxyl, and lower alkoxy, wherein the heterocycle ring further optionally comprises one or two additional heteroatoms chosen from N, O and S.

7. The compound of claim 6, and/or at least one pharmaceutically acceptable salt thereof, wherein $R^2$ is —S(O)$_n$N$R^c R^d$, wherein n is 2, $R^c$ and $R^d$ are each independently chosen from H and alkyl, or $R^c$ and $R^d$, with the nitrogen to which they are attached, form a pyrrolidinyl.

8. The compound of claim 1, and/or at least one pharmaceutically acceptable salt thereof, wherein $R^2$ is —S(O)$_n R^f$, wherein n is 2, $R^f$ is alkyl; phenyl optionally substituted by one or more groups chosen from halo, —CN, —NO$_2$, and —O$R^b$, wherein $R^b$ is —H or alkyl; or cyclaoalkyl.

9. The compound of claim 1, and/or at least one pharmaceutically acceptable salt thereof, wherein $R^2$ is aryl or heteroaryl chosen from

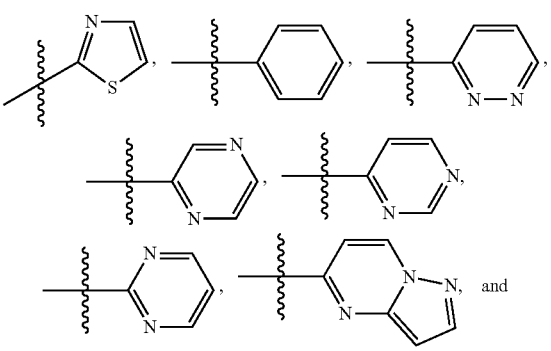

-continued

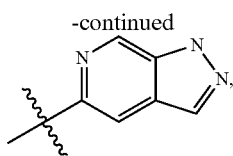

each of which is optionally substituted with one or more groups chosen from optionally substituted alkyl, optionally substituted alkenyl, optionally substituted alkynyl, optionally substituted aryl, optionally substituted cycloalkyl, optionally substituted haloalkyl, —C(O)R$^a$, —C(O)OR$^b$, —CN, —C(O)NR$^c$R$^d$, halo, optionally substituted heterocycle, optionally substituted heteroaryl, —NR$^c$R$^d$, —NR$^e$C(O)R$^a$, —NR$^e$C(O)OR$^b$, —NR$^e$C(O)NR$^c$R$^d$, —NR$^e$S(O)$_n$R$^f$, —NR$^e$S(O)$_n$NR$^c$R$^d$, —NO$_2$, —OR$^b$, —S(O)$_n$R$^f$, and —S(O)$_n$NR$^c$R$^d$.

10. The compound of claim 9, and/or at least one pharmaceutically acceptable salt thereof, wherein R$^2$ is

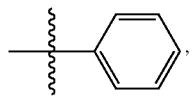 [SMILES: *c1ccccc1]

which is optionally substituted with one or more groups chosen from optionally substituted alkyl, optionally substituted alkenyl, optionally substituted alkynyl, optionally substituted aryl, optionally substituted cycloalkyl, optionally substituted haloalkyl, —C(O)R$^a$, —C(O)OR$^b$, —CN, —C(O)NR$^c$R$^d$, halo, optionally substituted heterocycle, optionally substituted heteroaryl, —NR$^c$R$^d$, —NR$^e$C(O)R$^a$, —NR$^e$C(O)OR$^b$, —NR$^e$C(O)NR$^c$R$^d$, —NR$^e$S(O)$_n$R$^f$, —NR$^e$S(O)$_n$NR$^c$R$^d$, —NO$_2$, OR$^b$, —S(O)$_n$R$^f$, and —S(O)$_n$NR$^c$R$^d$.

11. The compound of claim 10, and/or at least one pharmaceutically acceptable salt thereof, wherein R$^2$ is

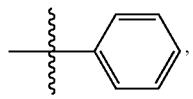

which is optionally substituted with one or more groups chosen from:
—CN;
halo;
haloalkyl;
—NO$_2$;
amino;
—S(O)$_n$R$^f$, wherein n is 2 and R$^f$ is alkyl or haloalkyl;
phenyl optionally substituted by one or more groups chosen from —CN, alkyoxy, and halo;
indanyl optionally substituted by —OH;
tetrazolyl; and
—C(O)NR$^c$R$^d$, wherein R$^c$ and R$^d$ are each independently chosen from —H; alkyl optionally substituted by —OH; alkoxy; phenyl optionally substituted by halo; and indanyl optionally substituted by —OH.

12. The compound of claim 10, and/or at least one pharmaceutically acceptable salt thereof, wherein R$^2$ is pyrazinyl optionally substituted with one or more groups chosen from: —CN, alkoxy, morpholino, pyrazolyl, imidazolyl, and —NR$^c$R$^d$, wherein R$^c$ and R$^d$ are each independently chosen from cycloalkyl and alkyl, each optionally substituted by —OH.

13. The compound of claim 9, and/or at least one pharmaceutically acceptable salt thereof, wherein R$^2$ is pyridazinyl optionally substituted with one or more groups chosen from —CN, halo, and haloalkyl.

14. The compound of claim 9, and/or at least one pharmaceutically acceptable salt thereof, wherein R$^2$ is pyrimidinyl optionally substituted with one or more groups chosen from —CN, halo, —NO$_2$, —OR$^b$, and —NR$^c$R$^d$, wherein R$^b$, R$^c$ and R$^d$, are each independently chosen from —H and alkyl.

15. The compound of claim 1, and/or at least one pharmaceutically acceptable salt thereof, wherein R$^1$ is chosen from C$_{1-3}$ alkyl, allyl, propargyl, and cyclopropyl, each of which is optionally substituted with one or more groups chosen from optionally substituted lower alkyl, optionally substituted cycloalkyl, —C(O)R$^a$, —C(O)OR$^b$, —CN, —C(O)NR$^c$R$^d$, halo, optionally substituted haloalkyl, optionally substituted heterocycle, optionally substituted heteroaryl, —NR$^c$R$^d$, —NR$^e$C(O)R$^a$, —NR$^e$C(O)OR$^b$, —NR$^e$C(O)NR$^c$R$^d$, —NR$^e$S(O)$_n$R$^f$, —NR$^e$S(O)$_n$NR$^c$R$^d$, NO$_2$, OR$^b$, —S(O)$_n$R$^f$, and —S(O)$_n$NR$^c$R$^d$.

16. The compound of claim 15, and/or at least one pharmaceutically acceptable salt thereof, wherein R$^1$ is methyl.

17. The compound of claim 1, and/or at least one pharmaceutically acceptable salt thereof, wherein the absolute stereocenter bearing the —N(R$^1$)(R$^2$) group is the R-isomer.

18. A compound according to claim 1 chosen from the compounds listed below:

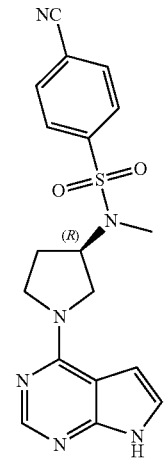

9

-continued
10 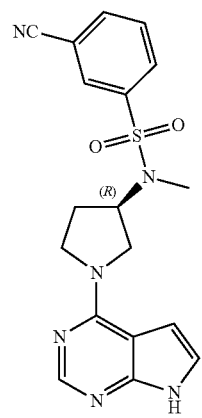
11 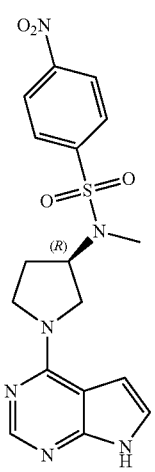
12 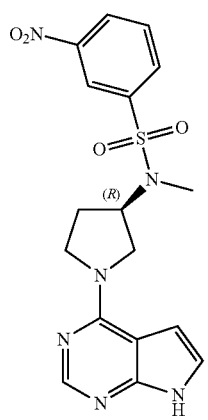
-continued
13 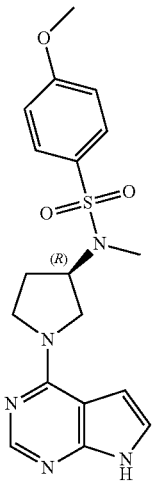
14 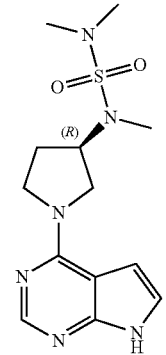
15 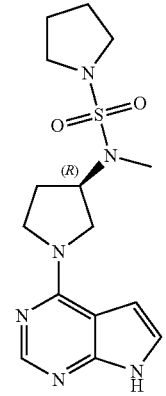
28 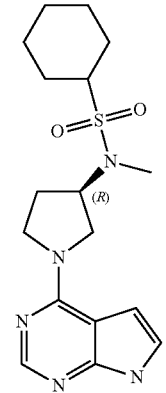

153
-continued
43
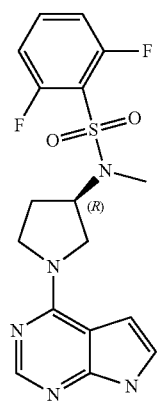
47
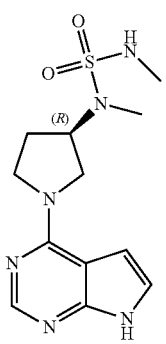
48
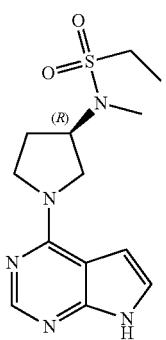
49
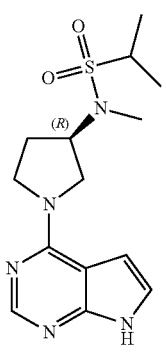
154
-continued
56
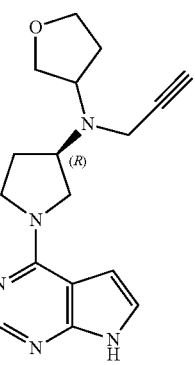
57
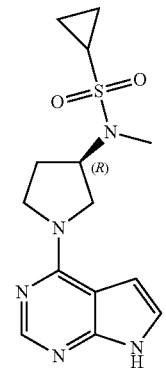
60
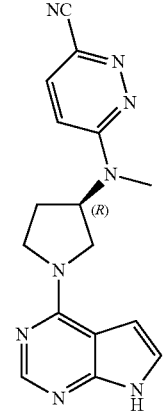
62
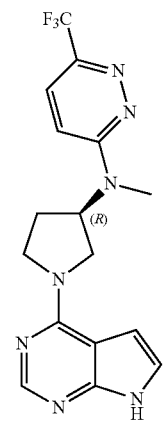

63
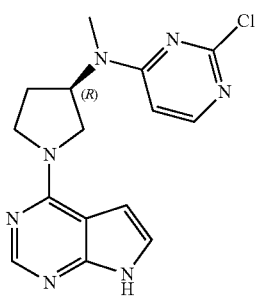
79
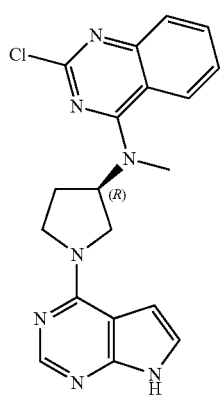
80
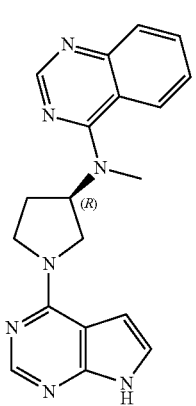
84
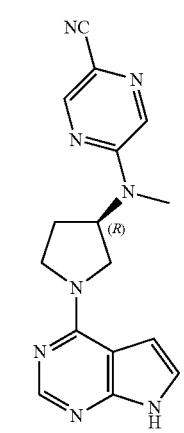
85
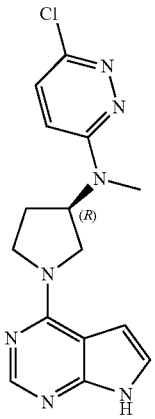
86
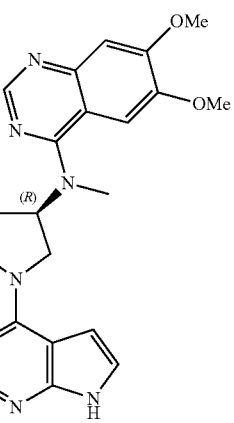
88
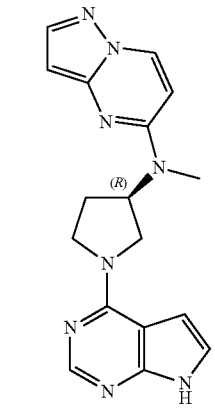
93
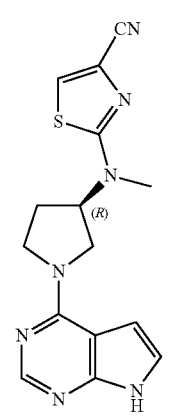

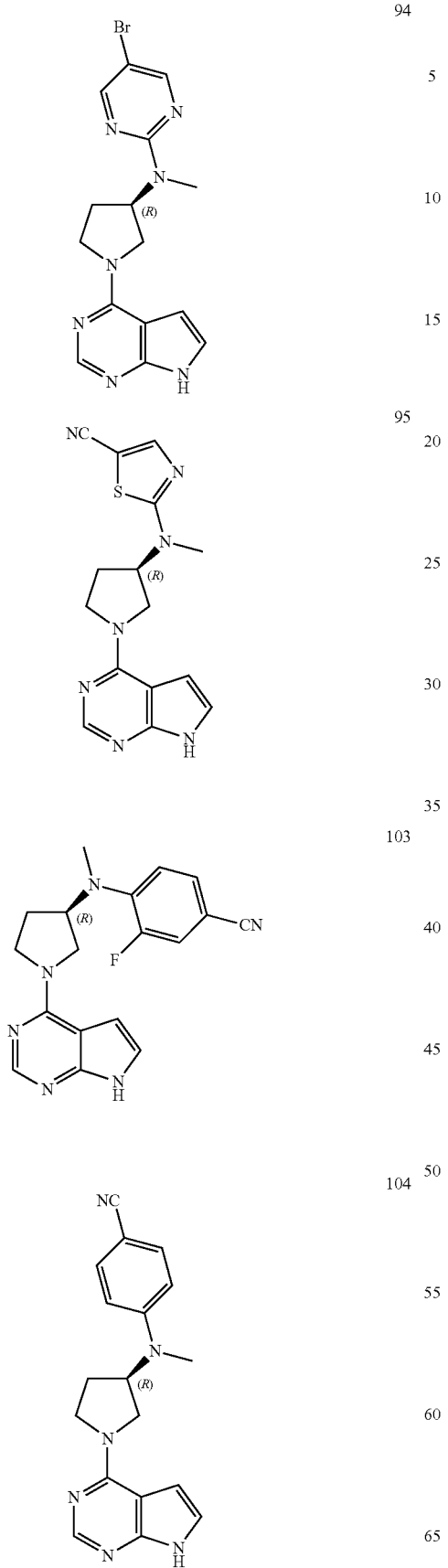

108 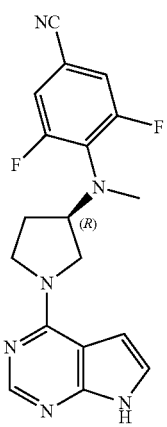
109 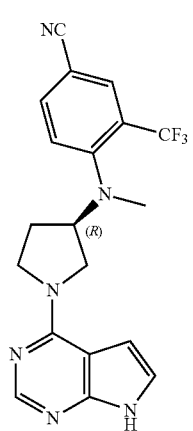
110 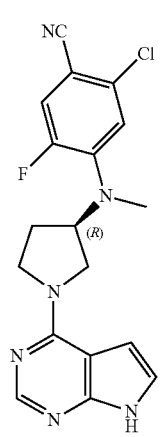
111 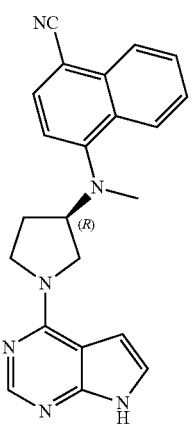
112 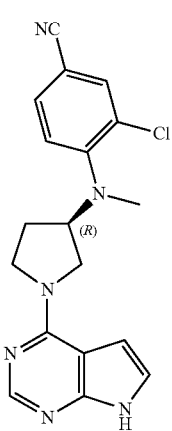
113 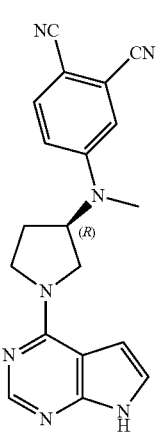

114 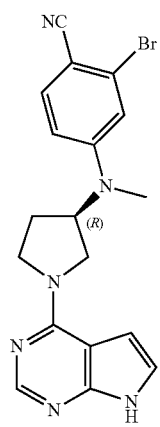
115 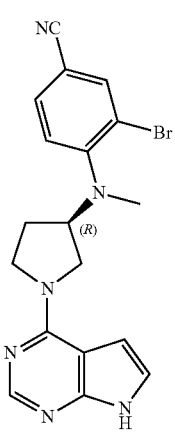
116 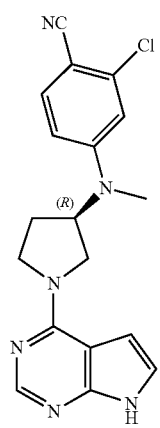
117 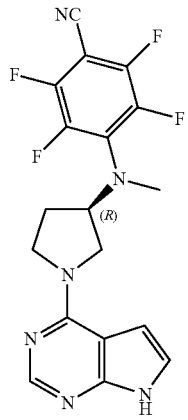
118 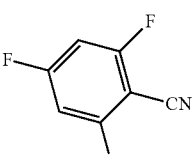
119 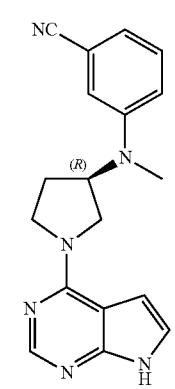
120 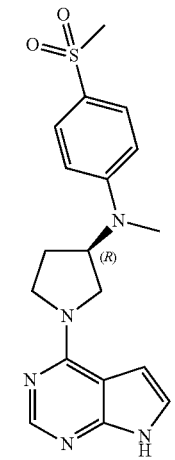

| 122 | 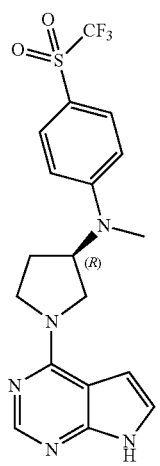 | 129 | 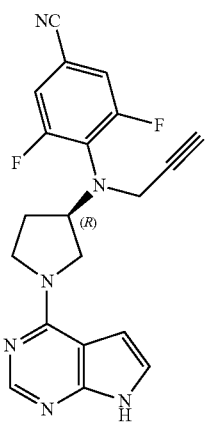 |
| 125 | 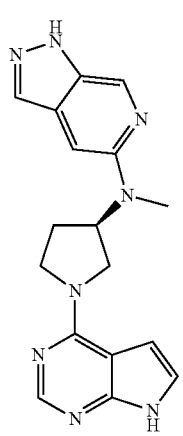 | 130 | 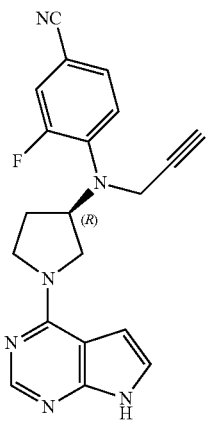 |
| 127 | 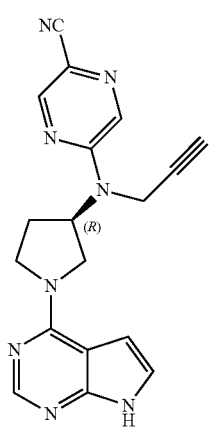 | 131 | 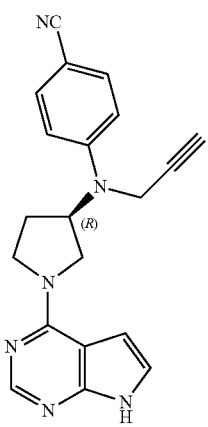 |

132
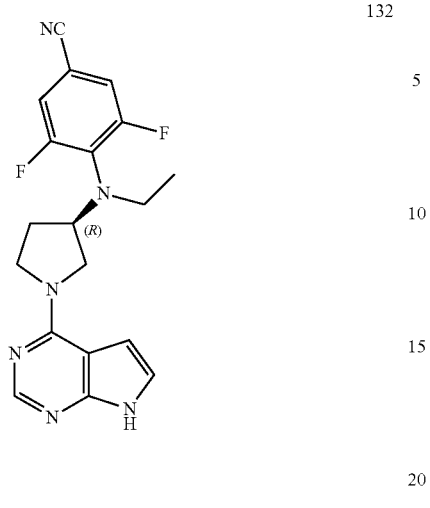
133
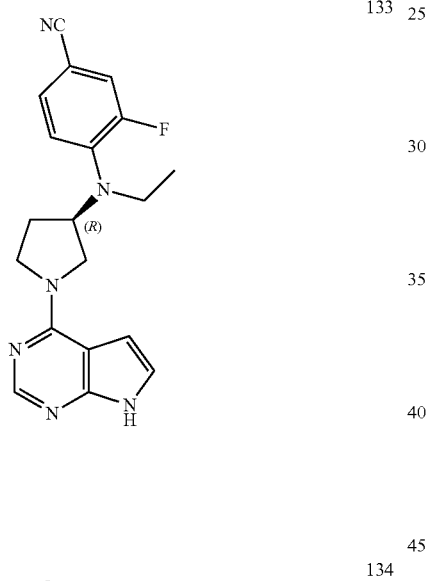
134
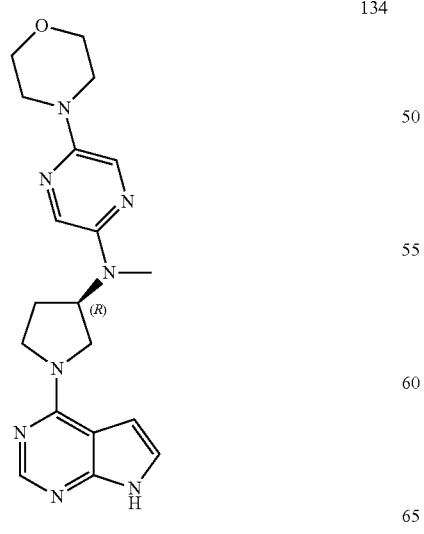
135
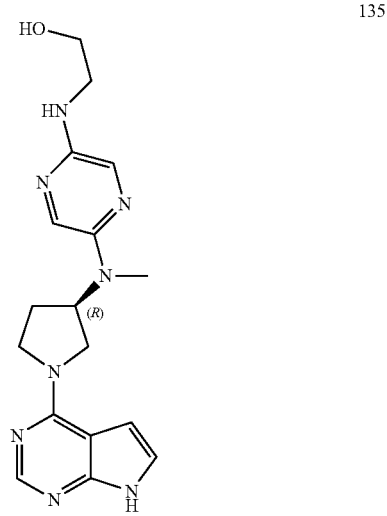
136
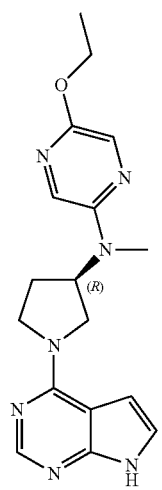
138
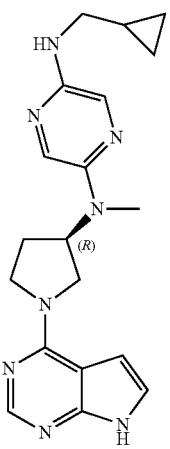

139
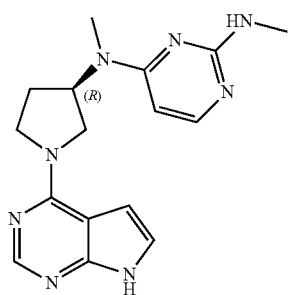
140
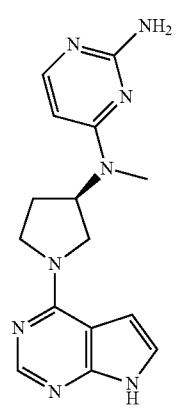
141
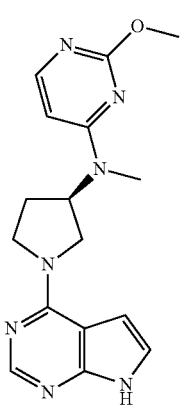
142
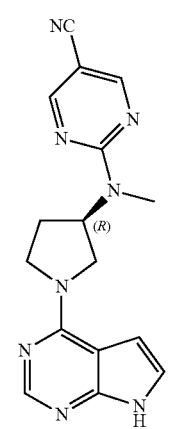
143
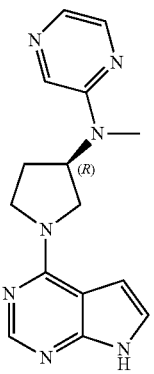
148
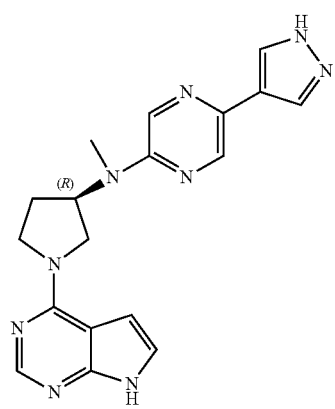
151
152
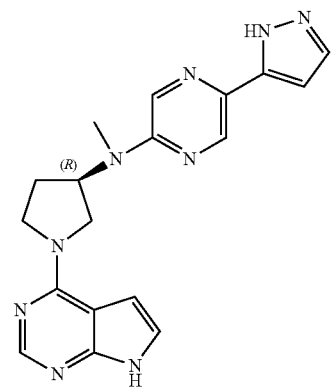

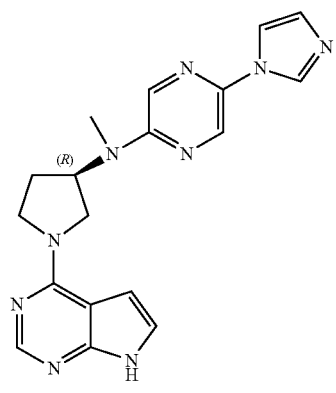
153
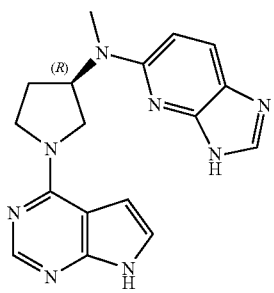
5
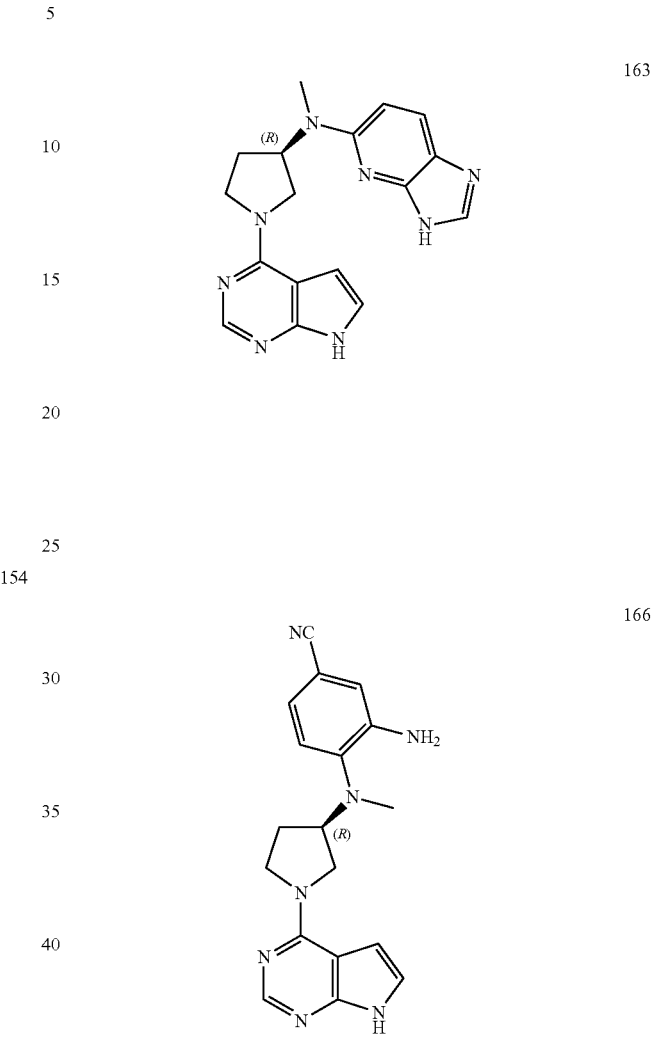
163
154
166
161
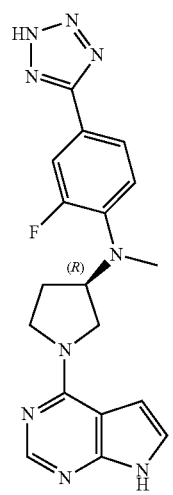
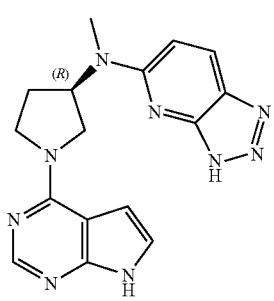
167

179
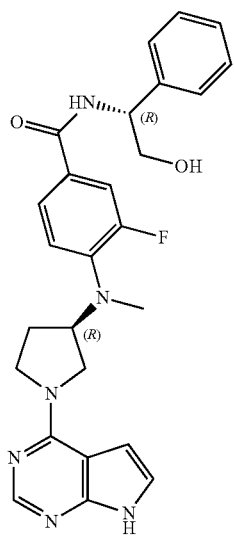
180
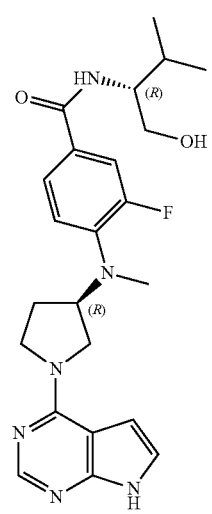
182
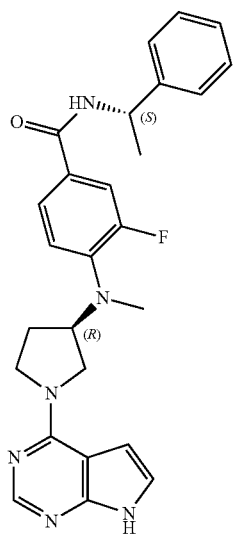
184
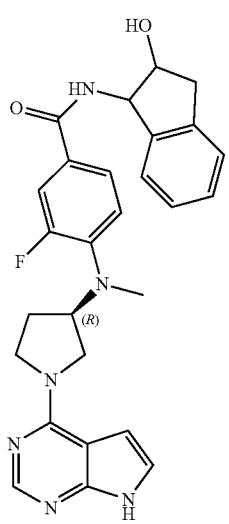
185
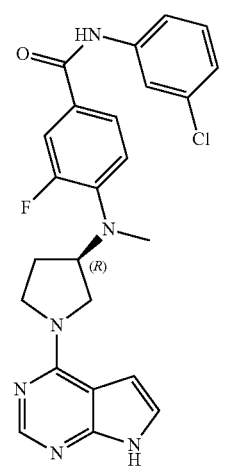
187
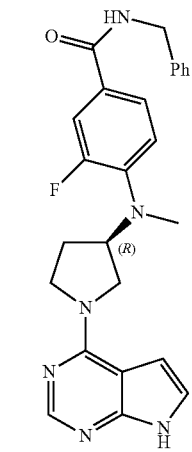

189
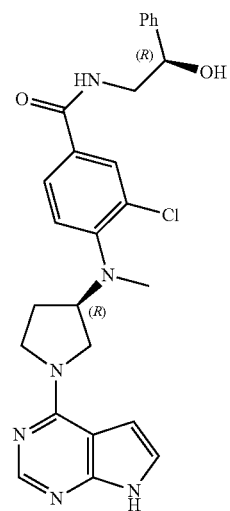
201
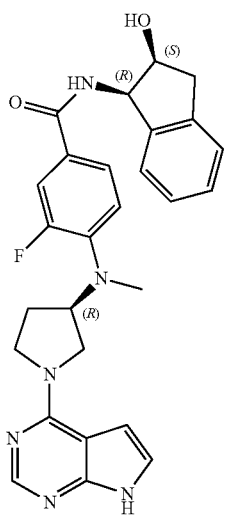
202
203
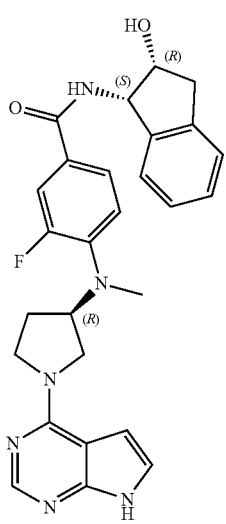
204
205
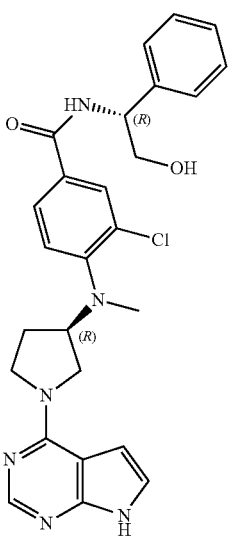

206

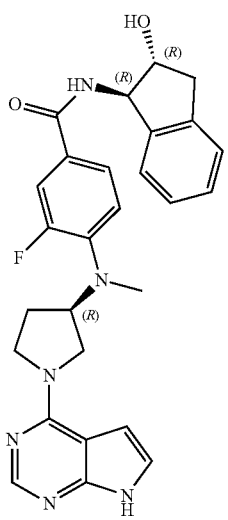

207

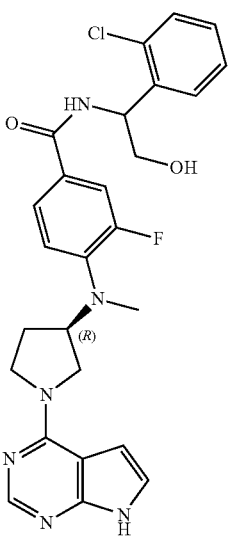

208

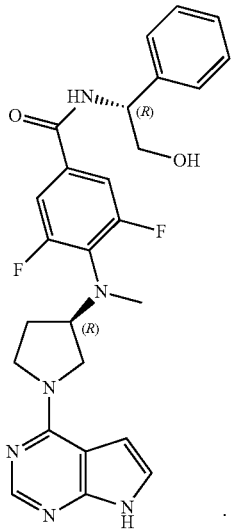

19. A composition comprising at least one compound of claim 1 and/or at least one pharmaceutically acceptable salt thereof, and at least one pharmaceutically acceptable carrier.

20. A method of inhibiting the activity of at least one kinase chosen from JAK1, JAK2, JAK3 and TYK2 comprising contacting the at least one kinase with an effective amount of a compound of claim 1 and/or at least one pharmaceutically acceptable salt thereof.

21. A method of treating in a subject an inflammatory disease responsive to inhibition of at least one kinase chosen from JAK1, JAK2, JAK3 and TYK2 comprising administering to said subject in need thereof an effective amount of a compound of claim 1 and/or at least one pharmaceutically acceptable salt thereof.

22. A method of treating in a subject a cancer responsive to inhibition of at least one kinase chosen from JAK1, JAK2, JAK3 and TYK2 comprising
  administering to said subject in need thereof an effective amount of a compound of claim 1 and/or at least one pharmaceutically acceptable salt thereof, and
  administering to the subject an amount of an anti-neoplastic agent, wherein said antineoplastic agent is different from said compound of claim 1, and/or at least one pharmaceutically acceptable salt thereof.

23. The compound of claim 1, wherein the compound is compound 60.

* * * * *